(12) United States Patent
Boyden et al.

(10) Patent No.: US 10,765,817 B2
(45) Date of Patent: Sep. 8, 2020

(54) METHODS, SYSTEMS, AND DEVICES RELATED TO DELIVERY OF ALCOHOL WITH AN INHALER

(71) Applicant: Elwha LLC, Bellevue, WA (US)

(72) Inventors: Edward S. Boyden, Chestnut Hill, MA (US); Roderick A. Hyde, Redmond, WA (US); Jordin T. Kare, San Jose, CA (US); Tony S. Pan, Bellevue, WA (US); Robert C. Petroski, Seattle, WA (US); Elizabeth A. Sweeney, Seattle, WA (US); Lowell L. Wood, Jr., Bellevue, WA (US)

(73) Assignee: Elwha, LLC, Bellevue, WA (US)

( * ) Notice: Subject to any disclaimer, the term of this patent is extended or adjusted under 35 U.S.C. 154(b) by 1028 days.

(21) Appl. No.: 14/620,586

(22) Filed: Feb. 12, 2015

(65) Prior Publication Data

US 2016/0045682 A1 Feb. 18, 2016

Related U.S. Application Data

(63) Continuation-in-part of application No. 14/549,398, filed on Nov. 20, 2014, which is a continuation-in-part of application No. 14/549,381, filed on Nov. 20, 2014, which is a continuation-in-part of application No. 14/485,460, filed on Sep. 12, 2014, (Continued)

(51) Int. Cl.
*A61M 15/00* (2006.01)
*A61M 16/00* (2006.01)
(Continued)

(52) U.S. Cl.
CPC ........ *A61M 15/0003* (2014.02); *A61M 11/02* (2013.01); *A61M 15/0068* (2014.02);
(Continued)

(58) Field of Classification Search
CPC .............. A61M 15/00; A61M 15/0001; A61M 15/0003; A61M 15/0011; A61M 15/0021;
(Continued)

(56) References Cited

U.S. PATENT DOCUMENTS 4,984,158 A 1/1991 Hillsman
5,333,106 A 7/1994 Lanpher et al.
(Continued)

FOREIGN PATENT DOCUMENTS

CN 1780655 A 5/2006
EP 1005916 A1 7/2000
(Continued)

OTHER PUBLICATIONS

"Evaluating Transdermal Alcohol Measuring Devices: Final Report"; U.S. Department of Transportation; Nov. 2007, pp. i-87; National Highway Traffic Safety Administration (NHTSA).
(Continued)

*Primary Examiner* — Tu A Vo

(57) ABSTRACT

Devices, systems, and methods that may be used to controllably deliver alcohol to a subject using an inhaler, wherein the inhaler may include a housing having a flow channel coupled to an ethanol-containing inhalant reservoir, an actuator configured to facilitate release of the inhalant, a constituent sensor, and a control unit. The control unit may accept parameters associated with the subject, create an inhalant delivery regime, and control operation of the actuator based at least partially on a sensed constituent level to facilitate release of an ethanol-containing inhalant from the reservoir into the flow channel in accordance with the regimen.

31 Claims, 31 Drawing Sheets

Related U.S. Application Data now Pat. No. 10,245,393, which is a continuation-in-part of application No. 14/459,075, filed on Aug. 13, 2014.

(51) Int. Cl.
*A61M 11/00* (2006.01)
*A61M 16/20* (2006.01)
*A61M 11/02* (2006.01)

(52) U.S. Cl.
CPC ..... *A61M 16/201* (2014.02); *A61M 2202/025* (2013.01); *A61M 2202/0208* (2013.01); *A61M 2202/0266* (2013.01); *A61M 2202/04* (2013.01); *A61M 2202/0484* (2013.01); *A61M 2205/3334* (2013.01); *A61M 2205/502* (2013.01); *A61M 2205/505* (2013.01); *A61M 2205/581* (2013.01); *A61M 2205/583* (2013.01)

(58) Field of Classification Search
CPC ............ A61M 16/201; A61M 15/0065; A61M 15/0068; A61M 15/0071; A61M 15/009; A61M 15/0091; A61M 15/06; A61M 15/08; A61M 11/00; A61M 11/02; A61M 11/04; A61M 11/06; A61M 11/08; A61M 2205/502; A61M 2202/04; A61M 2205/3334; A61M 2202/0484; A61M 2205/505; A61M 2205/581; A61M 2202/0266; A61M 2205/583; A61M 2202/025; A61M 2202/0208
See application file for complete search history.

(56) References Cited

U.S. PATENT DOCUMENTS

| | | | |
|---|---|---|---|
| 5,347,998 A * | 9/1994 | Hodson | A61M 15/0091 128/200.23 |
| 5,392,768 A * | 2/1995 | Johansson | A61M 15/00 128/200.14 |
| 5,404,871 A | 4/1995 | Goodman | |
| 5,419,315 A | 5/1995 | Rubsamen | |
| 5,497,764 A * | 3/1996 | Ritson | A61M 15/00 128/200.14 |
| 5,540,934 A | 7/1996 | Touitou | |
| 5,672,581 A * | 9/1997 | Rubsamen | A61K 9/007 424/43 |
| 6,142,146 A * | 11/2000 | Abrams | A61M 15/0085 128/203.15 |
| 6,196,219 B1 * | 3/2001 | Hess | A61M 15/0085 128/200.21 |
| 6,197,333 B1 | 3/2001 | Onyuksel et al. | |
| 6,221,385 B1 | 4/2001 | Camu et al. | |
| 6,269,810 B1 | 8/2001 | Brooker | |
| 6,316,024 B1 | 11/2001 | Allen et al. | |
| 6,335,267 B1 | 1/2002 | Iwamatsu et al. | |
| 6,354,516 B1 * | 3/2002 | Patel | A61M 15/0045 239/331 |
| 6,534,018 B1 | 3/2003 | Baker et al. | |
| 6,543,443 B1 * | 4/2003 | Klimowicz | A61M 15/0085 128/200.14 |
| 6,571,793 B1 | 6/2003 | Nilsson | |
| 6,623,671 B2 | 9/2003 | Coe et al. | |
| 6,684,880 B2 * | 2/2004 | Trueba | A61M 15/0085 128/200.16 |
| 6,739,333 B1 * | 5/2004 | Hoelz | A61M 15/009 128/200.23 |
| 6,759,057 B1 | 7/2004 | Weiner et al. | |
| 6,770,291 B2 | 8/2004 | Smyth-Templeton et al. | |
| 6,855,296 B1 | 2/2005 | Baker et al. | |
| 6,890,555 B1 | 5/2005 | Desair et al. | |
| 7,958,887 B2 | 6/2011 | Kelliher et al. | |
| 8,414,915 B2 | 4/2013 | Cipolla et al. | |
| 8,539,945 B2 | 9/2013 | Solomon et al. | |
| 8,662,381 B2 | 3/2014 | Kaar et al. | |
| 8,689,785 B2 | 4/2014 | Wright et al. | |
| 2002/0168322 A1 | 11/2002 | Clark et al. | |
| 2003/0101991 A1 | 6/2003 | Trueba | |
| 2003/0111088 A1 | 6/2003 | Fox | |
| 2004/0084044 A1 | 5/2004 | Childers et al. | |
| 2005/0066968 A1 | 3/2005 | Shofner et al. | |
| 2005/0081846 A1 | 4/2005 | Barney | |
| 2005/0133024 A1 | 6/2005 | Coifman | |
| 2005/0150488 A1 * | 7/2005 | Dave | A61J 7/0481 128/200.14 |
| 2005/0150489 A1 * | 7/2005 | Dunfield | A61M 15/0083 128/200.14 |
| 2005/0166913 A1 | 8/2005 | Sexton et al. | |
| 2005/0196345 A1 | 9/2005 | Diederichs et al. | |
| 2005/0247312 A1 | 11/2005 | Davies | |
| 2005/0251289 A1 * | 11/2005 | Bonney | A61M 15/00 700/244 |
| 2005/0274378 A1 | 12/2005 | Bonney et al. | |
| 2007/0051363 A1 * | 3/2007 | Andrus | A61M 15/0086 128/200.24 |
| 2007/0093786 A1 * | 4/2007 | Goldsmith | A61B 5/14532 604/890.1 |
| 2007/0157931 A1 | 7/2007 | Parker | |
| 2007/0240712 A1 * | 10/2007 | Fleming | A61M 15/0028 128/203.15 |
| 2008/0138397 A1 | 6/2008 | Schuster et al. | |
| 2008/0139910 A1 * | 6/2008 | Mastrototaro | G16H 40/63 600/365 |
| 2008/0308101 A1 * | 12/2008 | Spandorfer | A61M 15/009 128/203.14 |
| 2010/0121163 A1 * | 5/2010 | Vestel | A61B 5/1459 600/316 |
| 2011/0182831 A1 | 7/2011 | Gonda | |
| 2012/0136270 A1 * | 5/2012 | Leuthardt | G06F 19/00 600/532 |
| 2012/0183949 A1 * | 7/2012 | Hyde | A61B 5/082 435/5 |
| 2012/0282328 A1 | 11/2012 | Cipolla et al. | |
| 2012/0305011 A1 | 12/2012 | Gonda | |
| 2013/0104624 A1 | 5/2013 | Devine | |
| 2013/0112199 A1 | 5/2013 | Von Sckuckmann et al. | |
| 2013/0186398 A1 | 7/2013 | Baillet et al. | |
| 2013/0206141 A1 | 8/2013 | Thoemmes et al. | |
| 2014/0007873 A1 | 1/2014 | Smutney et al. | |
| 2014/0007874 A1 | 1/2014 | Ellwanger et al. | |
| 2014/0014105 A1 | 1/2014 | Berenshteyn et al. | |
| 2014/0053838 A1 | 2/2014 | Berenshteyn et al. | |
| 2014/0053839 A1 | 2/2014 | Nakamura et al. | |
| 2014/0083421 A1 | 3/2014 | Smutney et al. | |
| 2014/0190496 A1 | 7/2014 | Wensley et al. | |
| 2014/0243749 A1 * | 8/2014 | Edwards | G09B 9/00 604/187 |
| 2014/0251330 A1 * | 9/2014 | Collins | A61M 15/0086 128/203.14 |
| 2014/0365142 A1 * | 12/2014 | Baldwin | A61B 5/683 702/24 |
| 2015/0122257 A1 | 5/2015 | Winkler et al. | |
| 2015/0196060 A1 | 7/2015 | Wensley et al. | |
| 2015/0245661 A1 * | 9/2015 | Milin | A24F 47/008 131/329 |
| 2017/0106153 A1 | 4/2017 | Davidson et al. | |

FOREIGN PATENT DOCUMENTS

| | | | | |
|---|---|---|---|---|
| JP | 2005533583 A | 11/2005 | | |
| JP | 2009532189 A | 9/2009 | | |
| WO | WO 2014068504 A2 * | 5/2014 | ........ | A61M 15/0065 |

OTHER PUBLICATIONS

"Guidelines for Spray Nozzle Selection"; Spraying Systems Co.; www.spray.com; 2014, p. 1-4.
"Merck Index"; Merck and Co., 2001, 13th edition; Whitehouse Station, NJ, USA.

(56) References Cited

OTHER PUBLICATIONS

"Physicians' Desk Reference"; Thomson PDR, 2004. 58th edition; Montvale, NJ, USA.

Bhalaria, M.K.; Naik, Sachin; Misra, A.N.; "Ethosomes: A novel delivery system for antifungal drugs in the treatment of topical fungal diseases"; Indian Journal of Experimental Biology; May 2009, p. 368-375, vol. 47; India.

Coates, Matthew S.; Chan, Ham-Kin; Fletcher, David F.; Raper, Judy A.; "Effect of Design on the Performance of a Dry Powder Inhaler Using Computational Fluid Dynamics"; Journal of Pharmaceutical Sciences, Jun. 2006, p. 1382-1392, vol. 95, No. 6; USA.

Copley, Mark; "Assessing dry powder inhalers"; Copley Science; Jan. 2010; p. 1-8; USA.

Dave, Vivek; Kumar, Dhirendra; Lewis, Shaila; Paliwal, Sarvesh; "Ethosome for Enhanced Transdermal Drug Delivery of Aceclofenac"; International Journal of Drug Delivery; 2010, p. 81-92; http://www.arjounrals.org/ijdd.html.

Newman, Stephen P., PHD; "Principles of Metered-Dose Inhaler Design"; Respiratory Care, Sep. 2005, p. 1177-1190, vol. 50 No. 9; USA.

Nielsen, K.G.; Skov, M.; Klug, B.; Ifversen, M.; Bisgaard, H.; "Flow-dependent effect of formoterol dry-powder inhaled from the Aerolizer®"; European Respiratory Journal; 1997, p. 2105-2109, vol. 10; United Kingdom.

Sheth, Ketan K., MD., MBA.; George, Maureen R., MSN., RN., CS.; Kelly, H. William, PharMD; "Dry Powder Inhalers in the Treatment of Asthma: A continuing education monograph for physicians, nurses, pharmacists, physician assistants, and respiratory therapists."; Meniscus Limited; 2002; USA.

Terzano, C.; "Metered dose inhalers and spacer devices"; European Review for Medical and Pharmacological Sciences; 1999, p. 159-169, vol. 3; Department of Cardiovascular and Respiratory Sciences, "La Sapienza" University; Rome, Italy.

Troy, David B.; Beringer, Paul; "Remington: The Science and Practice of Pharmacy"; Lippincott, Williams & Wilkins; 2000, $20^{th}$ edition; Baltimore, MD, USA.

Webster, Gregory D.; Gabler, Hampton C.; "Feasibility of Transdermal Ethanol Sensing for the Detection of Intoxicated Drivers"; Center for Injury Biomechanics; Oct. 2007, pp. 449-464; Virginia Polytechnic and State University; Blackburg, VA, USA.

PCT International Search Report; International App. No. PCT/US2015/044773; dated Nov. 13, 2015; pp. 1-4.

European Patent Office, Extended European Search Report, Pursuant to Rule 62 EPC; App. No. EP15831963.2; dated Mar. 27, 2018; pp. 1-7.

Chinese State Intellectual Property Office, Notification of the First Office Action, App. No. 201580055212.2 (based on PCT App. No. PCT/US2015/044773); dated Jun. 28, 2019; pp. 1-6 (machine translation provided).

Chinese State Intellectual Property Office, Notification of the Second Office Action, App. No. 201580055212.2 (based on PCT App. No. PCT/US2015/044773); dated Mar. 19, 2020; pp. 1-7 (machine translation provided).

* cited by examiner

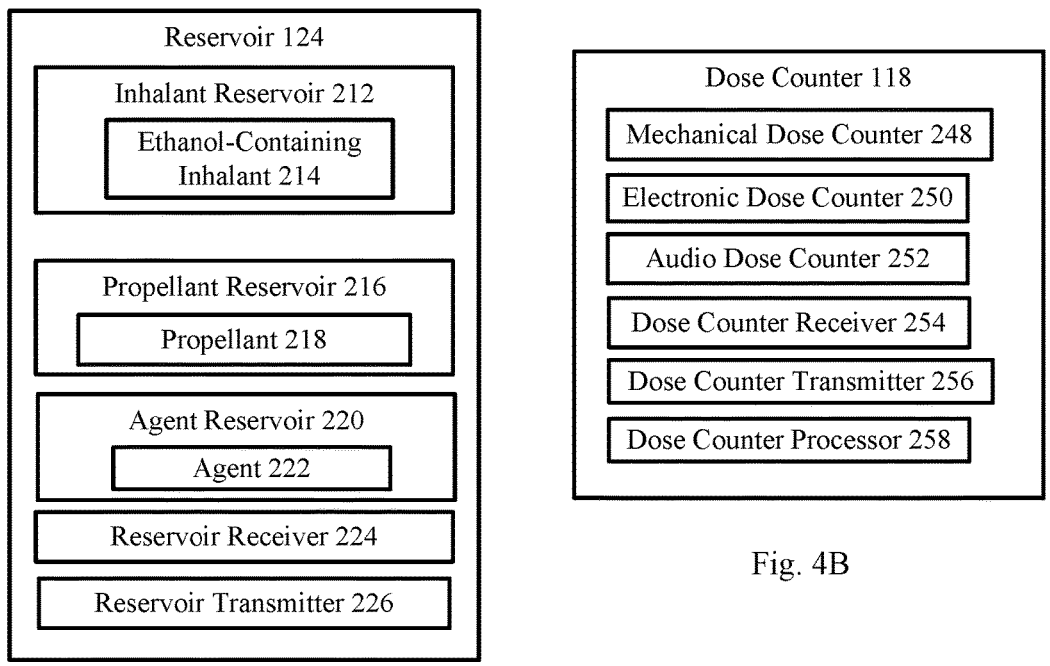
Fig. 4A
Fig. 4B
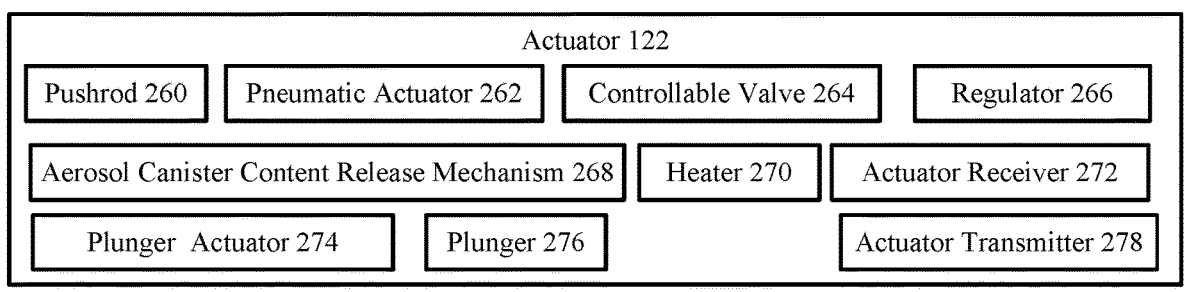
Fig. 4C

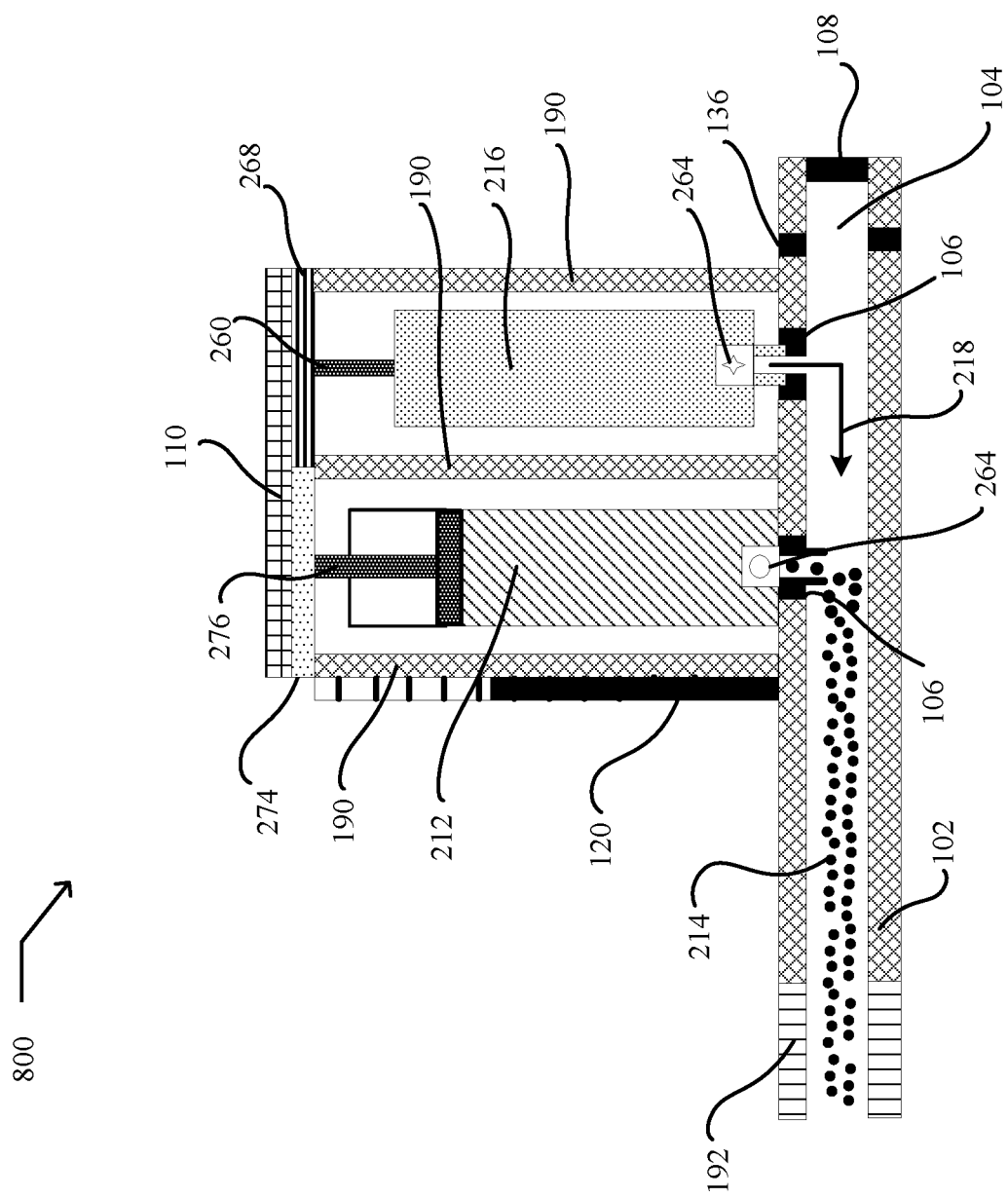

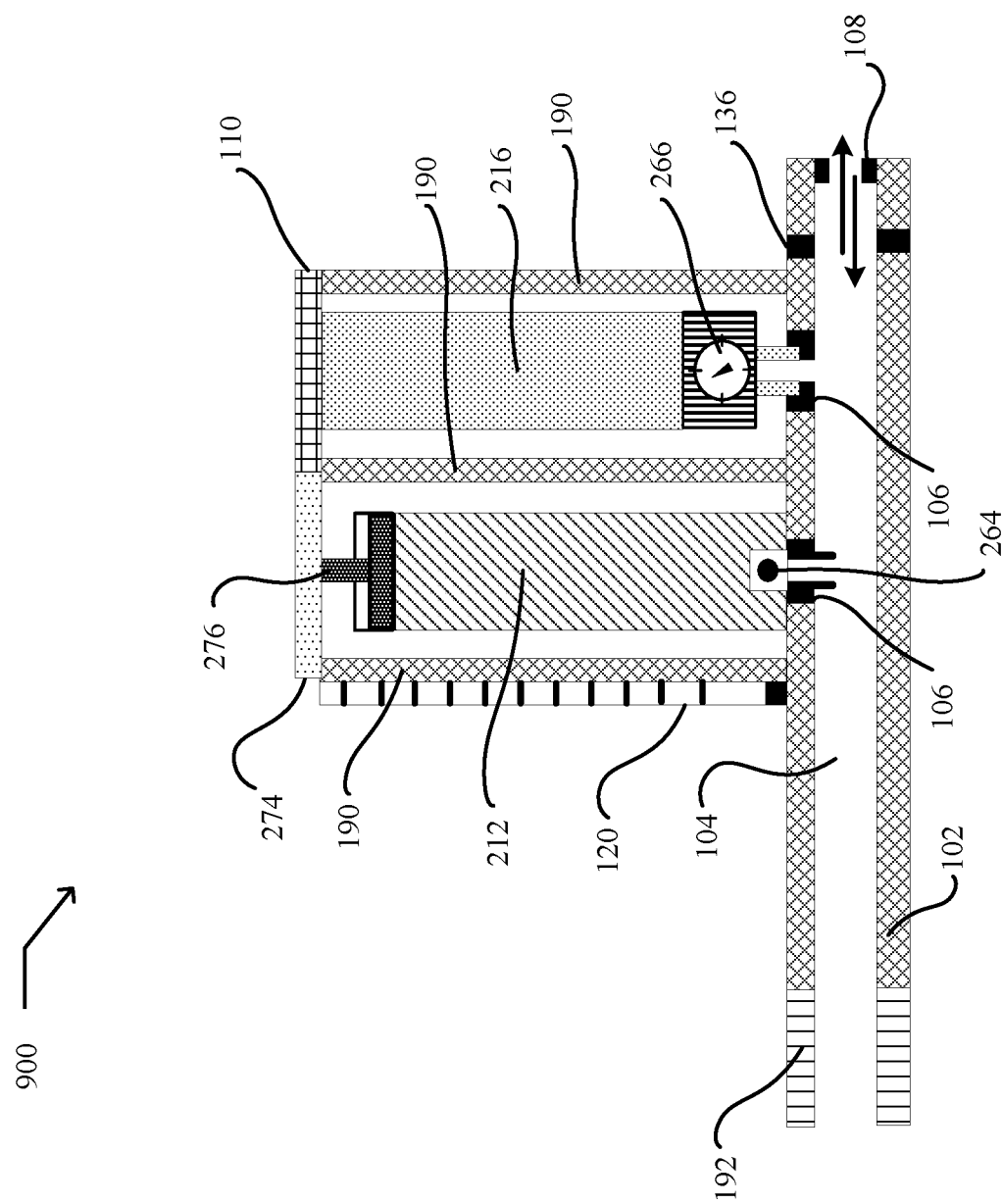

METHODS, SYSTEMS, AND DEVICES RELATED TO DELIVERY OF ALCOHOL WITH AN INHALER

If an Application Data Sheet (ADS) has been filed on the filing date of this application, it is incorporated by reference herein. Any applications claimed on the ADS for priority under 35 U.S.C. §§ 119, 120, 121, or 365(c), and any and all parent, grandparent, great-grandparent, etc. applications of such applications, are also incorporated by reference, including any priority claims made in those applications and any material incorporated by reference, to the extent such subject matter is not inconsistent herewith.

CROSS-REFERENCE TO RELATED APPLICATIONS

The present application claims the benefit of the earliest available effective filing date(s) from the following listed application(s) (the "Priority Applications"), if any, listed below (e.g., claims earliest available priority dates for other than provisional patent applications or claims benefits under 35 USC § 119(e) for provisional patent applications, for any and all parent, grandparent, great-grandparent, etc. applications of the Priority Application(s)). In addition, the present application is related to the "Related Applications," if any, listed below.

PRIORITY APPLICATIONS

For purposes of the USPTO extra-statutory requirements, the present application constitutes a continuation-in-part of U.S. patent application Ser. No. 14/459,075, entitled SYSTEMS, METHODS, AND DEVICES TO INCENTIVIZE INHALER USE, naming Jesse R. Cheatham, III, Roderick A. Hyde, Robert C. Petroski, Lowell L. Wood, Jr., and Victoria Y. H. Wood as inventors, filed 13 Aug. 2014, which is currently co-pending, or is an application of which a currently co-pending application is entitled to the benefit of the filing date;

For purposes of the USPTO extra-statutory requirements, the present application constitutes a continuation-in-part of U.S. patent application Ser. No. 14/549,381, entitled SYSTEMS, METHODS, AND DEVICES TO INCENTIVIZE INHALER USE, naming Jesse R. Cheatham, III, Roderick A. Hyde, Robert C. Petroski, Lowell L. Wood, Jr., and Victoria Y. H. Wood as inventors, filed 20 Nov. 2014, which is currently co-pending, or is an application of which a currently co-pending application is entitled to the benefit of the filing date;

For purposes of the USPTO extra-statutory requirements, the present application constitutes a continuation-in-part of U.S. patent application Ser. No. 14/549,398, entitled SYSTEMS, METHODS, AND DEVICES TO INCENTIVIZE INHALER USE, naming Jesse R. Cheatham, III, Roderick A. Hyde, Robert C. Petroski, Lowell L. Wood, Jr., and Victoria Y. H. Wood as inventors, filed 20 Nov. 2014, which is currently co-pending, or is an application of which a currently co-pending application is entitled to the benefit of the filing date; and For purposes of the USPTO extra-statutory requirements, the present application constitutes a continuation-in-part of U.S. patent application Ser. No. 14/485,460, entitled METHODS, SYSTEMS, AND DEVICES RELATED TO A SUPPLEMENTAL INHALER, naming Roderick A. Hyde and Leif T. Stordal as inventors, filed 12 Sep. 2014, which is currently co-pending, or is an application of which a currently co-pending application is entitled to the benefit of the filing date.

RELATED APPLICATIONS

None.

If the listings of applications provided above are inconsistent with the listings provided via an ADS, it is the intent of the Applicant to claim priority to each application that appears in the Priority Applications section of the ADS and to each application that appears in the Priority Applications section of this application.

All subject matter of the Priority Applications and the Related Applications and of any and all parent, grandparent, great-grandparent, etc. applications of the Priority Applications and the Related Applications, including any priority claims, is incorporated herein by reference to the extent such subject matter is not inconsistent herewith.

SUMMARY

In one aspect, an inhaler includes, but is not limited to, a housing having at least one flow channel disposed therein configured to be fluidly coupled to at least one ethanol-containing inhalant reservoir; at least one actuator configured to facilitate at least partial release of at least one ethanol-containing inhalant from at least one ethanol-containing inhalant reservoir into the at least one flow channel; and at least one control unit including at least one processing component configured to, accept one or more parameters associated with a subject, access or create an ethanol-containing inhalant delivery regimen associated with the subject in response to the one or more parameters, and control operation of the at least one actuator to facilitate at least partial release of the at least one ethanol-containing inhalant from the ethanol-containing inhalant reservoir into the at least one flow channel in response to the ethanol-containing inhalant delivery regimen associated with the subject. In some embodiments, an inhaler may optionally include at least one port disposed in the housing in fluid communication with the at least one flow channel. In some embodiments, an inhaler may optionally include at least one ethanol-containing inhalant reservoir including at least one aerosol canister having a canister body and a valve stem that extends from the canister body, and wherein the housing includes at least one reservoir support configured to support the at least one aerosol canister with the valve stem being received by the at least one port. In some embodiments, an inhaler may optionally include at least one ethanol-containing inhalant reservoir. In some embodiments, an inhaler may optionally include at least one ethanol sensor configured to detect at least one ethanol characteristic of the at least one ethanol-containing inhalant. In some embodiments, an inhaler may optionally include at least one dose counter. In some embodiments, an inhaler may optionally include at least one additional reservoir. In some embodiments, an inhaler may optionally include at least one output device. In addition to the foregoing, other inhaler aspects are described in the claims, drawings, and text forming a part of the present disclosure.

In one aspect, a method includes, but is not limited to, accepting one or more parameters associated with a subject; creating an ethanol delivery regimen associated with the subject in response to the one or more parameters; and controllably dispensing an ethanol-containing inhalant from an inhaler according to the ethanol delivery regimen associated with the subject, wherein at least one of the accepting one or more parameters, creating an ethanol delivery regimen, or controllably dispensing an ethanol-containing inhalant is at least partially implemented using one or more processing devices. In some embodiments, a method may optionally include selecting one or more agents and dispensing the one or more agents. In addition to the foregoing, other method aspects are described in the claims, drawings, and text forming a part of the present disclosure.

In one aspect, a system includes, but is not limited to, circuitry configured to accept one or more parameters associated with a subject; circuitry configured to at least one of access or create an ethanol delivery regimen in response to the one or more parameters; and circuitry configured to dispense an ethanol-containing inhalant from an inhaler according to the ethanol delivery regimen associated with the subject. In some embodiments, a system may optionally include circuitry configured to select one or more agents and circuitry configured to dispense the one or more agents. In addition to the foregoing, other system aspects are described in the claims, drawings, and text forming a part of the present disclosure.

In one aspect, a system includes, but is not limited to, means for accepting one or more parameters associated with a subject; means for creating an ethanol delivery regimen in response to the one or more parameters; and means for dispensing an ethanol-containing inhalant from an inhaler according to the ethanol delivery regimen associated with the subject. In some embodiments, a system may optionally include means for selecting one or more agents and means for dispensing the one or more agents. In addition to the foregoing, other system aspects are described in the claims, drawings, and text forming a part of the present disclosure.

In one aspect, a system includes, but is not limited to, a non-transitory signal-bearing medium bearing one or more instructions that, when executed by one or more processing components, direct performance of operations that include at least: accepting one or more parameters associated with a subject; creating an ethanol delivery regimen in response to the one or more parameters; and dispensing an ethanol-containing inhalant from an inhaler according to the ethanol delivery regimen associated with the subject. In some embodiments, a system may optionally include one or more instructions that direct performance of an operation that includes at least selecting one or more agents and one or more instructions that direct performance of an operation that includes at least dispensing the one or more agents. In some embodiments, a system may optionally include a non-transitory signal-bearing medium that includes at least a computer-readable medium. In some embodiments, a system may optionally include a non-transitory signal-bearing medium that includes at least a recordable medium. In some embodiments, a system may optionally include a non-transitory signal-bearing medium that includes at least a communications medium. In addition to the foregoing, other system aspects are described in the claims, drawings, and text forming a part of the present disclosure.

In one aspect, an inhaler includes, but is not limited to, a housing having at least one flow channel disposed therein configured to be fluidly coupled to at least one ethanol-containing inhalant reservoir; at least one sensor; at least one actuator configured to facilitate at least partial release of inhalant from at least one ethanol-containing inhalant reservoir into the at least one flow channel; and at least one control unit configured to direct operation of the at least one actuator at least partially in response to information received from the at least one sensor. In some embodiments, an inhaler may optionally include at least one port disposed in the housing in fluid communication with the at least one flow channel. In some embodiments, an inhaler may optionally include at least one reservoir. In some embodiments, an inhaler may optionally include at least one dose counter. In some embodiments, an inhaler may optionally include at least one flow valve operably coupled with the at least one flow channel. In addition to the foregoing, other inhaler aspects are described in the claims, drawings, and text forming a part of the present disclosure.

In one aspect, a method includes, but is not limited to, dispensing an ethanol-containing inhalant from an inhaler to a subject and assessing ethanol emitted from the subject with the inhaler. In some embodiments, a method may optionally include assessing an additional quantity of the ethanol-containing inhalant to dispense to the subject in response to assessing the ethanol. In some embodiments, a method may optionally include dispensing the additional quantity of the ethanol-containing inhalant to the subject. In some embodiments, a method may optionally include displaying one or more indicators associated with the one or more concentrations of the ethanol emitted from the subject. In some embodiments, a method may optionally include dispensing one or more additional agents to the subject. In addition to the foregoing, other method aspects are described in the claims, drawings, and text forming a part of the present disclosure.

In one aspect, a system includes, but is not limited to, circuitry configured to facilitate at least partial release of an ethanol-containing inhalant from at least one ethanol-containing inhalant reservoir that is operably coupled to an inhaler and circuitry configured to assess ethanol emitted from a subject associated with the inhaler. In some embodiments, a system may optionally include circuitry configured to determine an additional quantity of the ethanol-containing inhalant to release in response to assessing the ethanol emitted from the subject. In some embodiments, a system may optionally include circuitry configured to facilitate at least partial release of the additional quantity of the ethanol-containing inhalant. In some embodiments, a system may optionally include circuitry configured to display one or more indicators associated with assessing the ethanol emitted from the subject. In some embodiments, a system may optionally include circuitry configured to dispense one or more agents to the subject. In addition to the foregoing, other system aspects are described in the claims, drawings, and text forming a part of the present disclosure.

In one aspect, a system includes, but is not limited to, means for facilitating at least partial release of an ethanol-containing inhalant from at least one ethanol-containing inhalant reservoir that is operably coupled to an inhaler and means for assessing ethanol emitted from a subject associated with the inhaler. In some embodiments, a system may optionally include means for determining an additional quantity of the ethanol-containing inhalant to release in response to assessing the ethanol emitted from the subject. In some embodiments, a system may optionally include means for facilitating at least partial release of the additional quantity of the ethanol-containing inhalant. In some embodiments, a system may optionally include means for displaying one or more indicators associated with assessing the ethanol emitted from the subject. In some embodiments, a system may optionally include means for dispensing one or more agents to the subject. In addition to the foregoing, other system aspects are described in the claims, drawings, and text forming a part of the present disclosure.

In one aspect, a system includes, but is not limited to, a non-transitory signal-bearing medium bearing one or more instructions that, when executed by one or more processing components, direct performance of operations that include at least: facilitating at least partial release of an ethanol-containing inhalant from at least one ethanol-containing inhalant reservoir that is operably coupled to an inhaler and assessing ethanol emitted from a subject associated with the inhaler. In some embodiments, a system may optionally include one or more instructions that direct performance of an operation that includes at least determining an additional quantity of the ethanol-containing inhalant to release in response to assessing the ethanol emitted from the subject. In some embodiments, a system may optionally include one or more instructions that direct performance of an operation that includes at least facilitating at least partial release of the additional quantity of the ethanol-containing inhalant. In some embodiments, a system may optionally include one or more instructions that direct performance of an operation that includes at least displaying one or more indicators associated with assessing the ethanol emitted from the subject. In some embodiments, a system may optionally include one or more instructions that direct performance of an operation that includes at least dispensing one or more agents to the subject. In some embodiments, a system may optionally include a non-transitory signal-bearing medium that includes at least a computer-readable medium. In some embodiments, a system may optionally include a non-transitory signal-bearing medium that includes at least a recordable medium. In some embodiments, a system may optionally include a non-transitory signal-bearing medium that includes at least a communications medium. In addition to the foregoing, other system aspects are described in the claims, drawings, and text forming a part of the present disclosure.

In one or more various aspects, means include but are not limited to circuitry and/or programming for effecting the herein referenced functional aspects; the circuitry and/or programming can be numerous combinations of hardware, software, and/or firmware configured to effect the herein referenced functional aspects depending upon the design choices of the system designer. For example, in some embodiments, means may not include software. In addition to the foregoing, other system aspects means are described in the claims, drawings, and/or text forming a part of the present disclosure.

In one or more various aspects, related systems include but are not limited to circuitry and/or programming for effecting the herein-referenced method aspects; the circuitry and/or programming can be numerous combinations of hardware, software, and/or firmware configured to effect the herein referenced method aspects depending upon the design choices of the system designer. For example, in some embodiments, circuitry may not include software. In addition to the foregoing, other system aspects are described in the claims, drawings, and/or text forming a part of the present application.

The foregoing is a summary and thus may contain simplifications, generalizations, inclusions, and/or omissions of detail; consequently, those skilled in the art will appreciate that the summary is illustrative only and is NOT intended to be in any way limiting. Other aspects, features, and advantages of the devices and/or processes and/or other subject matter described herein will become apparent in the teachings set forth herein.

BRIEF DESCRIPTION OF THE FIGURES

FIGS. 4A through 4C illustrate example components of system 100 in which embodiments may be implemented.

FIG. 8A illustrates a cross-sectional partial side view of an example inhaler 800 (as viewed along view A-A of FIG. 5B) in which embodiments may be implemented.

FIG. 9 illustrates a cross-sectional partial side view of an example inhaler 900 (as viewed along view A-A of FIG. 5B) in which embodiments may be implemented.

DETAILED DESCRIPTION

Figure 1:
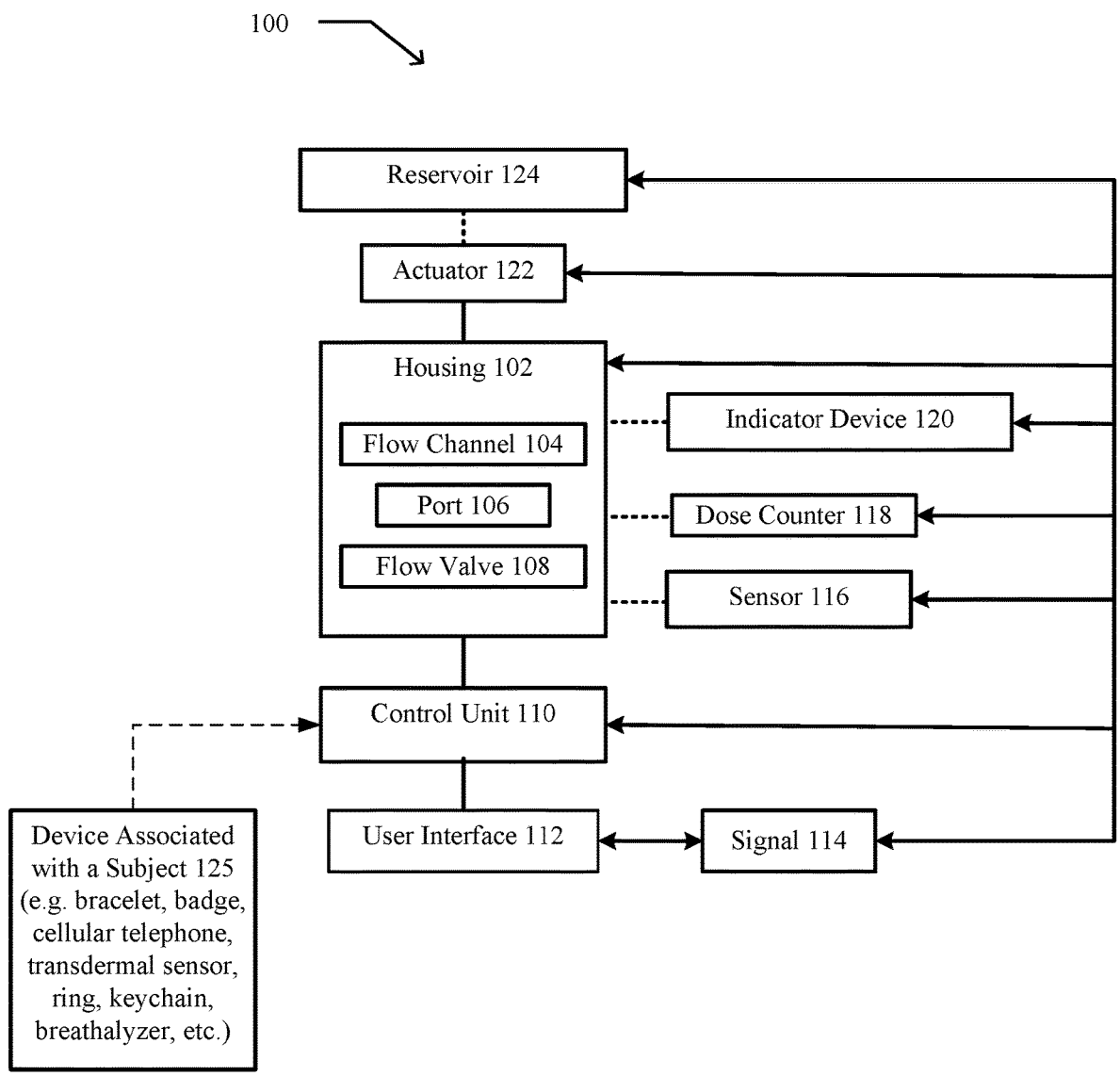
FIG. 1 illustrates an example system 100 in which embodiments may be implemented.
Figure 2A:
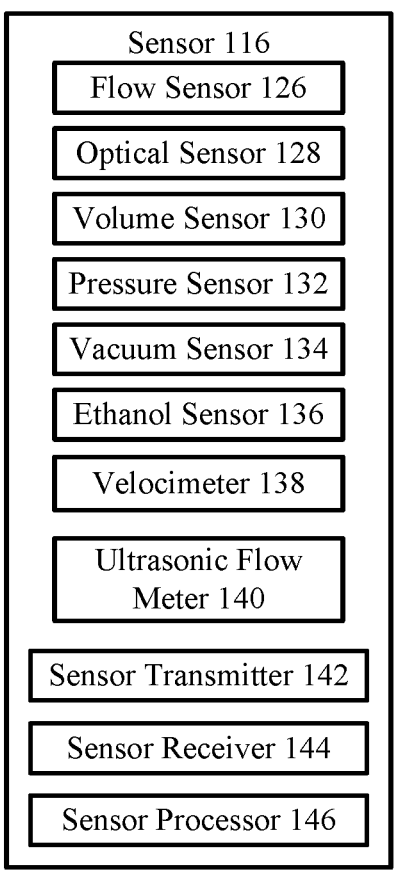
FIGS. 2A through 2D illustrate example components of system 100 in which embodiments may be implemented.
Figure 2B:
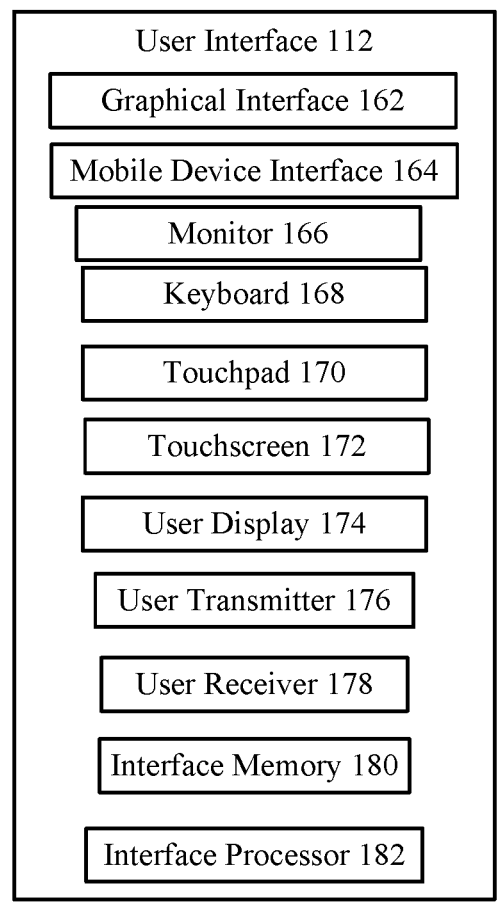
Figure 2C:
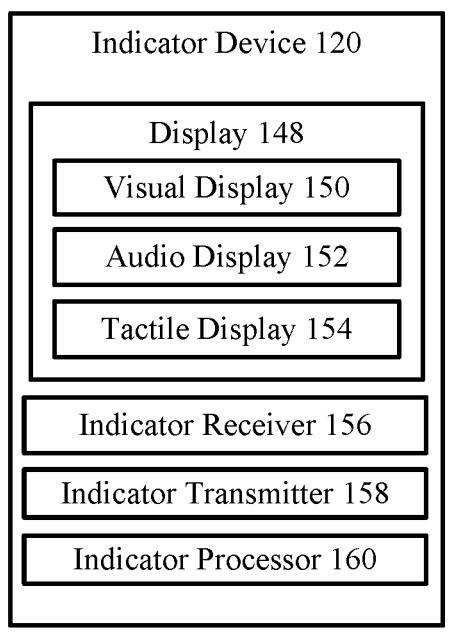
Figure 2D:
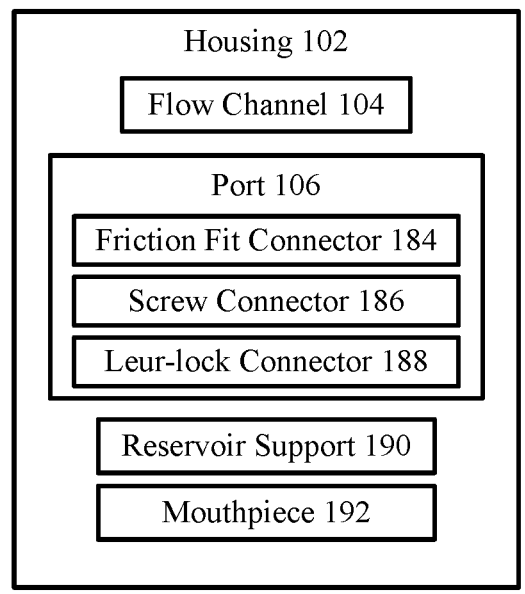

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

FIG. 1 illustrates an example system 100 in which numerous embodiments may be implemented. In some embodiments, system 100 may be implemented as an inhaler. In some embodiments, system 100 may include a housing 102 having at least one flow channel 104 disposed therein. In some embodiments, system 100 may include at least one port 106 disposed within the housing 102 and operably coupled to at least one flow channel 104 and configured to provide fluid communication between at least one reservoir 124 and at least one flow channel 104. In some embodiments, system 100 may include one or more actuators 122. In some embodiments, system 100 may include one or more reservoirs 124. In some embodiments, system 100 may include one or more dose counters 118. In some embodiments, system 100 may include one or more indicator devices 120. In some embodiments, system 100 may include one or more control units 110. In some embodiments, system 100 may include one or more sensors 116. In some embodiments, system 100 may include one or more user interfaces 112. In some embodiments, system 100 may include one or more signals 114.

FIGS. 2A through 2D illustrate example embodiments of components that may be included in system 100. The illustrated components include a sensor 116, an indicator device 120, a user interface 112, and a housing 102.

Figure 3A:
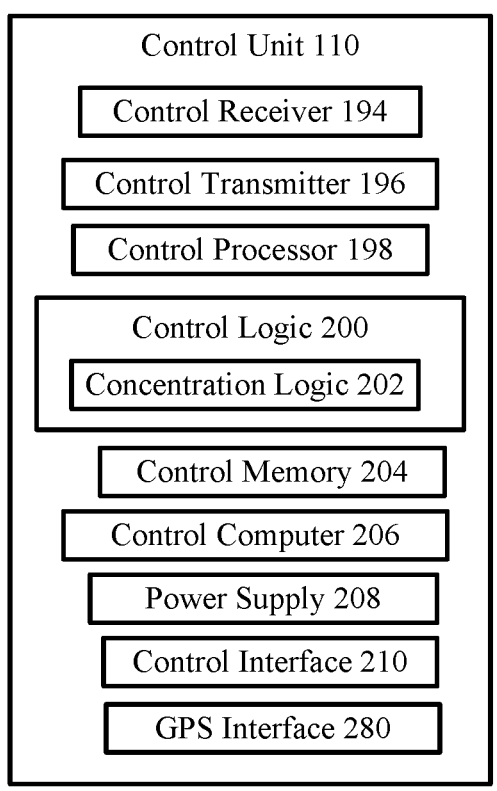
FIGS. 3A through 3B illustrate example components of system 100 in which embodiments may be implemented.
Figure 3B:
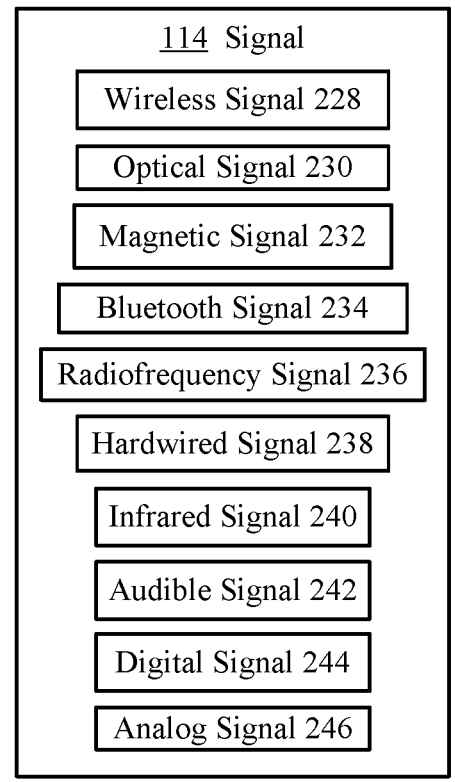

FIGS. 3A through 3B illustrate example embodiments of components that may be included in system 100. The illustrated components include a control unit 110 and a signal 114.

FIGS. 4A through 4C illustrate example embodiments of components that may be included in system 100. The illustrated components include a dose counter 118, an actuator 122, and a reservoir 124.

Housing

With reference to FIGS. 1-4C, in some embodiments, system 100 may include one or more housings 102. A housing 102 may be configured in numerous ways. In some embodiments, a housing 102 may be configured for inclusion within an inhaler. In some embodiments, a housing 102 may include one or more flow channels 104 disposed therein. In some embodiments, a housing 102 may include a single flow channel 104 disposed therein. In some embodiments, a housing 102 may include a plurality of flow channels 104 disposed therein. For example, in some embodiments, a housing 102 may include a first flow channel 104 disposed therein that is configured to be fluidly coupled to at least one inhalant reservoir 212 and direct an ethanol-containing inhalant 214 released from the inhalant reservoir 212 into the first flow channel 104. The housing 102 may also include a second flow channel 104 disposed therein that is configured to be fluidly coupled to at least one agent reservoir 220 and direct an agent 222 released from the agent reservoir 220 into the second flow channel 104. In some embodiments, a housing 102 may include a first flow channel 104 disposed therein that is configured to direct an ethanol-containing inhalant 214 into the first flow channel 104, and a second flow channel 104 disposed therein that is coupled with a sensor 116 configured to detect one or more characteristics associated with passage of material through the second flow channel 104. For example, in some embodiments, a sensor 116 may be configured to assess flow through a flow channel 104. Examples of such sensors 116 include, but are not limited to, a flow sensor 126, an optical sensor 128, a volume sensor 130, a pressure sensor 132, a vacuum sensor 134, and ethanol sensor 136, a velocimeter 138, an ultrasonic flow meter 140, and the like. In some embodiments, a sensor 116 may be configured to assess one or more characteristics of an ethanol-containing inhalant 214. For example, in some embodiments, a flow channel 104 may be coupled to an ethanol sensor 136 that is configured to assess ethanol concentration in material passing through the flow channel 104. In some embodiments, a flow channel 104 may be coupled to an ethanol sensor 136 that is configured to assess ethanol content in an ethanol-containing inhalant 214 that passes through the flow channel 104. In some embodiments, a housing may include a flow valve 108 that is operably coupled with a flow channel 104 and configured to control flow through the flow channel 104. For example, in some embodiments, a flow valve 108 may be held in an open position to allow flow through a flow channel 104. In some embodiments, a flow valve 108 may be held in a closed position to disallow flow through a flow channel 104.

In some embodiments, a housing 102 may include one or more ports 106 disposed therein. In some embodiments, a housing 102 may include at least one port 106 disposed within the housing 102 and operably coupled to at least one flow channel 104 and configured to provide fluid communication between at least one reservoir 124 and at least one flow channel 104. Accordingly, in some embodiments, a port 106 may be configured to operably couple with one or more reservoirs 124 and direct contents released from the one or more reservoirs 124 into one or more flow channels 104 disposed within a housing 102. In some embodiments, a port 106 may be configured to facilitate at least partial delivery of an ethanol-containing inhalant from an inhalant reservoir 212 into a flow channel 104. In some embodiments, a port 106 may be configured to facilitate at least partial delivery of propellant 218 from a propellant reservoir 216 into a flow channel 104. In some embodiments, a port 106 may be configured to facilitate delivery of one or more aerosolized formulations from a reservoir 124 into a flow channel 104. For example, in some embodiments, a port 106 may be configured to operably couple with an aerosol canister that includes a canister body and a valve stem that extends from the canister body and into a port 106 that is aligned with a flow channel 104. In some embodiments, a housing 102 may include at least one port 106 disposed in the housing 102 and operably coupled to at least one flow channel 104 and configured to receive one or more reservoirs 124. In some embodiments, a housing 102 may include two or more ports 106 disposed within the housing 102 that are each operably coupled to at least one flow channel 104 and are each configured to receive a reservoir 124. In some embodiments, a housing 102 may include one port 106 disposed in the housing 102 that is operably coupled to at least one flow channel 104 and configured to receive two or more reservoirs 124. A port 106 may include numerous types of connectors that allow one or more reservoirs 124 to be operably coupled to the port 106. Examples of such connectors include, but are not limited to, friction fit connectors 184, screw connectors 186, Leur-lock connectors 188, and the like.

In some embodiments, a port 106 may include an actuator 120 that is operable to facilitate at least partial release of contents from one or more operably coupled reservoirs 124. For example, in some embodiments, a port 106 may include a controllable valve 264 that may be opened and closed to facilitate at least partial release of contents from an operably coupled reservoir 124 into at least one flow channel 104. In some embodiments, such a controllable valve 264 may be operably coupled with a control unit 110 that is configured to control the operation of the controllable valve 264. In some embodiments, such a controllable valve 264 may be operably coupled with a sensor 116. In some embodiments, such a controllable valve 264 may be operably coupled with a sensor 116 that is configured to control the operation of the controllable valve 264. In some embodiments, such a controllable valve 264 may be operably coupled with a control unit 110 and a sensor 116 that are configured to control operation of the controllable valve 264. In some embodiments, a port 106 may include a controllable valve 264 that may be opened and closed to facilitate at least partial release of contents from an inhalant reservoir 214. In some embodiments, a port 106 may include a controllable valve 264 that may be opened and closed to facilitate at least partial release of contents from a propellant reservoir 216. In some embodiments, a port 106 may include a controllable valve 264 that may be opened and closed to facilitate at least partial release of contents from an agent reservoir 220.

In some embodiments, a port 106 may include a regulator 266 that may be configured to facilitate at least partial release of contents from an operably coupled reservoir 124. In some embodiments, a port 106 may include a regulator 266 that may be opened and closed to facilitate at least partial release of contents from a reservoir 124 into at least one flow channel 104. In some embodiments, a port 106 may include a regulator 266 that may be opened and closed to facilitate at least partial release of contents from an inhalant reservoir 212. In some embodiments, a port 106 may include a regulator 266 that may be opened and closed to facilitate at least partial release of contents from an agent reservoir 220. In some embodiments, a port 106 may include a regulator 266 that may be opened and closed to facilitate at least partial release of contents from a propellant reservoir 216. In some embodiments, such a regulator 266 may be operably coupled with a control unit 110 that is configured to control the operation of the regulator 266. In some embodiments, such a regulator 266 may be operably coupled with a sensor 116. In some embodiments, such a regulator 266 may be operably coupled with a sensor 116 that is configured to control the operation of the regulator 266. In some embodiments, such a regulator 266 may be operably coupled with a control unit 110 and a sensor 116 that are configured to control operation of the regulator 266. Accordingly, a port 106 may be configured in numerous ways.

In some embodiments, a housing 102 may include at least one reservoir support 190. For example, in some embodiments, a housing 102 may include at least one reservoir support 190 that is configured to support at least one aerosol canister that includes a canister body and a valve stem that extends from the canister body with the valve stem being in fluid communication with at least one flow channel 104 disposed within the housing 102. In some embodiments, a housing 102 may include at least one reservoir support 190 that is configured to support at least one propellant reservoir 216. For example, in some embodiments, a housing 102 may include at least one reservoir support 190 that is configured to support a propellant reservoir 216 that is configured as a compressed gas cylinder. Accordingly, a reservoir support 190 may be configured in numerous ways.

In some embodiments, a housing 102 may include at least one mouthpiece 192 that is operably coupled with one or more flow channels 104. In some embodiments, a mouthpiece 192 may be operably coupled with one or more sensors 116. A mouthpiece 192 may be operably coupled with numerous types of sensors 116. Examples of such sensors 116 include, but are not limited to, flow sensors 126, optical sensors 128, volume sensors 130, pressure sensors 132, vacuum sensors 134, ethanol sensors 136, velocimeters 138, ultrasonic flow meters 140, and the like.

Reservoir

With continued reference to FIGS. 1-4C, in some embodiments, system 100 may include one or more reservoirs 124. A reservoir 124 may be configured in numerous ways. In some embodiments, a reservoir 124 may include one or more reservoir receivers 224. In some embodiments, a reservoir 124 may include one or more reservoir transmitters 226. Accordingly, in some embodiments, a reservoir 124 may transmit one or more signals 114. In some embodiments, a reservoir 124 may receive one or more signals 114.

In some embodiments, a reservoir 124 may be operably coupled with a control unit 110. In some embodiments, a reservoir 124 may be operably coupled with a control unit 110 that controls operation of the reservoir 124. For example, in some embodiments, a control unit 110 may direct an inhalant reservoir 212 to at least partially release an ethanol-containing inhalant 214. In some embodiments, a reservoir 124 may be operably coupled with a sensor 116. In some embodiments, a reservoir 124 may be operably coupled with a sensor 116 that controls operation of the reservoir 124. For example, in some embodiments, an ethanol sensor 136 may detect a quantity of an ethanol-containing inhalant 214 released from an inhalant reservoir 212 and then direct the inhalant reservoir 212 to release an additional quantity of ethanol-containing inhalant 214. In some embodiments, an inhalant reservoir 122 may be operably coupled with a sensor 116 that detects a quantity of ethanol-containing inhalant 214 contained within the inhalant reservoir 212. In some embodiments, an inhalant reservoir 212 may be operably coupled with a sensor 116 that detects a quantity of an ethanol-containing inhalant 214 contained within the inhalant reservoir 212 and a dose counter 118 that displays the amount of ethanol-containing inhalant 214 contained within the inhalant reservoir 212. In some embodiments, a propellant reservoir 216 may be operably coupled with a sensor 116 that detects a quantity of propellant 218 contained within the propellant reservoir 216 and a dose counter 118 that displays the amount of propellant 218 contained within the propellant reservoir 216. In some embodiments, an agent reservoir 220 may be operably coupled with a sensor 116 that detects a quantity of agent 222 contained within the agent reservoir 220 and a dose counter 118 that displays the amount of agent 222 contained within the agent reservoir 220.

An inhalant reservoir 212 may contain numerous types of ethanol-containing inhalants 214. In some embodiments, an inhalant reservoir 212 may contain numerous types of ethanol-containing inhalants 214 and numerous types of agents 222. For example, an inhalant reservoir 212 may contain ethanol-containing inhalants 214 having a wide range of ethanol concentrations. For example, in some embodiments, an ethanol-containing inhalant 214 may contain at least 10 percent ethanol, at least 20 percent ethanol, at least 30 percent ethanol, at least 40 percent ethanol, at least 50 percent ethanol, at least 60 percent ethanol, at least 70 percent ethanol, at least 80 percent ethanol, at least 90 percent ethanol, or 100 percent ethanol. In some embodiments, an ethanol-containing inhalant 214 may contain less than 90 percent ethanol, less than 80 percent ethanol, less than 70 percent ethanol, less than 60 percent ethanol, less than 50 percent ethanol, less than 40 percent ethanol, less than 30 percent ethanol, less than 20 percent ethanol, or less than 10 percent ethanol. In some embodiments, an ethanol-containing inhalant 214 may contain between 10 percent ethanol and 100 percent ethanol, between 20 percent ethanol and 80 percent ethanol, between 30 percent ethanol and 70 percent ethanol, or between 50 percent ethanol and 80 percent ethanol. Accordingly, in some embodiments, an ethanol-containing inhalant 214 may contain numerous percentages of ethanol. Such percentages may be measured by mass or volume.

In some embodiments, an inhalant reservoir 212 may contain an ethanol-containing inhalant 214 and a carrier. For example, in some embodiments, various gasses may be used as a carrier. Examples, of such gasses include, but are not limited to, oxygen, nitrogen, neon, helium, and the like.

In some embodiments, an inhalant reservoir 212 may contain numerous types of ethanol-containing inhalant 214 formulations. Examples of such formulations include, but are not limited to, formulations that include liposomal components. For example, in some embodiments, an inhalant reservoir 212 may contain ethanol, lecithin, and water to form ethosomes. In some embodiments, a formulation may include ethosomes. In some embodiments, a formulation may include liposomes.

An inhalant reservoir 212 may also contain formulations having various release profiles. For example, in some embodiments, a formulation may have a substantially immediate ethanol release profile. In some embodiments, a formulation may have a substantially delayed ethanol release profile. In some embodiments, a formulation may have a sustained ethanol release profile. In some embodiments, a formulation may have numerous combinations of ethanol release profiles. For example, in some embodiments, a formulation may have a substantially immediate ethanol release profile and a sustained ethanol release profile. In some embodiments, a formulation may have an intermediate ethanol release profile and a sustained ethanol release profile. In some embodiments, a formulation may have a substantially immediate ethanol release profile and a substantially delayed ethanol release profile.

In some embodiments, an inhalant reservoir 212 may contain ethanol in numerous physical forms. For example, in some embodiments, an inhalant reservoir 212 may contain liquid ethanol. In some embodiments, an inhalant reservoir 212 may contain ethanol encapsulated within particles. In some embodiments, an inhalant reservoir 212 may contain ethanol vapor. In some embodiments, an inhalant reservoir 212 may contain ethanol in an aerosol form.

In some embodiments, an inhalant reservoir 212 may include ethanol-containing particles that may be of numerous sizes. For example, in some embodiments, such particles may be of a size that will deliver ethanol to the upper pulmonary tract of a subject. In some embodiments, such particles may be of a size that will deliver ethanol to the middle pulmonary tract of a subject. In some embodiments, such particles may be of a size that will deliver ethanol to the lower pulmonary tract of a subject. In some embodiments, an inhalant reservoir 212 may contain numerous combinations of particle sizes that will deliver ethanol to various positions with the pulmonary tract of a subject. For example, in some embodiments, an inhalant reservoir 212 may contain particles of a size that will deliver ethanol to the upper and lower pulmonary tract of a subject. In some embodiments, an inhalant reservoir 212 may contain ethanol-containing particles that are between about 0.5 micrometers and about 4 micrometers. In some embodiments, an inhalant reservoir 212 may contain ethanol-containing particles that are between about 1 micrometers and about 4 micrometers. In some embodiments, an inhalant reservoir 212 may contain ethanol-containing particles that are between about 4 micrometers and about 10 micrometers. In some embodiments, an inhalant reservoir 212 may contain ethanol-containing particles that are between about 10 micrometers and about 30 micrometers. Accordingly, an inhalant reservoir 212 may contain ethanol-containing particles that are numerous sizes and combinations of sizes.

In some embodiments, an inhalant reservoir 212 may contain one or more tracers. For example, in some embodiments, a tracer may be a fluorescent compound. In some embodiments, a tracer may be a marker protein. In some embodiments, a tracer may be a radionuclide.

In some embodiments, an inhalant reservoir 212 may contain one or more liquors. Examples of such liquors include, but are not limited to, vodka, gin, whiskey, bourbon, tequila, everclear, scotch, and the like.

An agent reservoir 220 may contain numerous types of agents 222. Examples of such agents 222 include, but are not limited to, surfactant lipids, steroids, anti-inflammatory drugs, bronchodilators, leukotriene modifiers, long-acting beta antagonists, 1,3-dimethylxanthine, short-acting beta agonists, [8-methyl-8-(1-methylethyl)-8-azoniabicyclo [3.2.1]oct-3-yl]3-hydroxy-2-phenyl-propanoate, antibodies, and the like (see e.g., *Remingtion: The Science and Practice of Pharmacy*, Lippincott, Williams & Wilkins, 20th edition, Baltimore, Md., USA (2000), *Physicians' Desk Reference*, Thomson PDR, 58th edition, Montvale, N.J. (2004); *Merck Index*, Merck and Co., 13th edition., Whitehouse Station, N.J. (2001); which are hereby incorporated by reference).

In some embodiments, an agent reservoir 220 may contain one or more flavorants. For example, in some embodiments, an agent reservoir 220 may contain an apple flavorant, an orange flavorant, a grape flavorant, a gin flavorant, a whiskey flavorant, a bourbon flavorant, and the like. For example, in some embodiments, an agent reservoir 220 may contain a flavorant that includes or mimics a congener found in a liquor, e.g., a flavorant that is a volatile organic compound. For example, in some embodiments, an agent reservoir 220 may contain as a flavorant a tastant or odorant. In some embodiments, an agent reservoir 220 may contain a flavorant that has been encapsulated or is formulated as a particle. For example, in some embodiments, one or more flavorant may be formulated with specific release kinetics. In some embodiments, an agent reservoir 220 may contain a flavorant that is a vapor or aerosol. In some embodiments, an agent reservoir 220 may contain a flavorant that is pleasant, for example one that will add to the experience of using the inhaler. In some embodiments, an agent reservoir 220 may contain a flavorant that is unpleasant, for example one that will discourage use of the inhaler, e.g., by a disapproved subject or at a disapproved time. In some embodiments, a flavorant may be selected by a subject using an inhaler. For example, in some embodiments, a subject may select one or more agent reservoirs 220 from which one or more flavorants are dispensed. In some embodiments, a flavorant may be selected by a control unit 110. For example, in some embodiments, a control unit 110 may select one or more agent reservoirs 220 from which one or more flavorants are dispensed.

In some embodiments, an agent reservoir 220 may contain caffeine. In some embodiments, an agent reservoir 220 may contain nicotine. In some embodiments, an agent reservoir 220 may contain tetrahydrocannabinol. In some embodiments, an agent reservoir 220 may contain a combination of agents. Accordingly, in some embodiments, an agent reservoir 220 may contain numerous types of agents 222.

A propellant reservoir 216 may contain numerous types of propellants 218. Examples of such propellants 218 include, but are not limited to, chlorofluorocarbons, hydrofluoroalkanes, compressed gases (e.g., air, nitrogen, oxygen), and the like. In some embodiments, a propellant reservoir 216 may include a combination of propellants 218.

Agents 222 may be included in numerous types of formulations. In some embodiments, a formulation may be a liquid formulation. Accordingly, in some embodiments, a formulation may include a carrier fluid. In some embodiments, a formulation may be an aerosolized formulation. In some embodiments, a formulation may be a powdered formulation. In some embodiments, a formulation may be a powdered inhalation formulation. Accordingly, in some embodiments, a formulation may include a carrier powder. In some embodiments, a formulation may include one agent 214. In some embodiments, a formulation may include more than one agent 214. Accordingly, in some embodiments, a formulation may include numerous combinations of agents 222.

In some embodiments, a reservoir 124 may be configured to contain a liquid formulation. For example, in some embodiments, an agent reservoir 220 may be configured as an aerosol canister that includes a canister body and a valve stem that extends from the canister body. In some embodiments, contents may be at least partially released from an aerosol canister by depressing the valve stem relative to the canister body. In some embodiments, a reservoir 124 may be configured to contain a powdered formulation.

Actuator

With continued reference to FIGS. 1-4C, in some embodiments, system 100 may include one or more actuators 122. System 100 may include numerous types of actuators 122 and combinations of actuators 122. In some embodiments, an actuator 122 may be configured to facilitate at least partial release of contents from one or more reservoirs 124. For example, in some embodiments, an actuator 122 may be configured to facilitate at least partial release of one or more ethanol-containing inhalants 214 from one or more inhalant reservoirs 212. In some embodiments, an actuator 122 may be configured to facilitate at least partial release of one or more agents 222 from one or more agent reservoirs 220. In some embodiments, an actuator 122 may be configured to facilitate at least partial release of propellant 218 from one or more propellant reservoirs 216.

Examples of actuators 122 include, but are not limited to, controllable valves 264, pushrod actuators 260, regulators 266, pneumatic actuators 262, aerosol canister content release mechanisms 268, heaters 270, plunger actuators 274, plungers 276, and the like. In some embodiments, an actuator 122 may be configured as an aerosol canister content release mechanism 268 that includes a pushrod actuator 260 that can depress an aerosol canister to open a controllable valve 264 and release contents of the aerosol canister.

In some embodiments, an actuator 122 may include one or more actuator receivers 272. In some embodiments, an actuator 122 may include one or more actuator transmitters 278. Accordingly, in some embodiments, an actuator 122 may transmit one or more signals 114. In some embodiments, an actuator 122 may receive one or more signals 114. In some embodiments, an actuator 122 may be operably coupled to one or more sensors 116. Accordingly, in some embodiments, an actuator 122 may be controlled in response to one or more parameters that are detected by one or more sensors 116. For example, in some embodiments, a sensor 116 may detect a quantity of an ethanol-containing inhalant 214 flowing through a flow channel 104 and control the operation of one or more operably coupled actuators 122 in response to the quantity of ethanol-containing inhalant 214 detected. In some embodiments, a sensor 116 may detect a quantity of an agent 222 flowing through a flow channel 104 and control the operation of one or more operably coupled actuators 122 in response to the quantity of agent 222 detected. In some embodiments, a sensor 116 may detect a quantity of propellant 218 flowing through a flow channel 104 and control the operation of one or more operably coupled actuators 122 in response to the quantity of propellant 218 detected. In some embodiments, a sensor 116 may detect when a subject using an inhaler is inhaling and activate one or more operably coupled actuators 122 to facilitate at least partial release from a reservoir 124 during the inhalation cycle. In some embodiments, a sensor 116 may detect when a subject using an inhaler is exhaling and deactivate one or more operably coupled actuators 122 to halt release from a reservoir 124 during the exhalation cycle. In some embodiments, a sensor 116 may detect when a subject using an inhaler is holding their breath and deactivate one or more operably coupled actuators 122 to halt release from a reservoir 124 during the breath holding cycle.

Dose Counter

As further shown in FIGS. 1-4C, in some embodiments, system 100 may include one or more dose counters 118. Dose counters 118 may be configured in numerous ways. In some embodiments, a dose counter 118 may include one or more dose counter receivers 254. In some embodiments, a dose counter 118 may include one or more dose counter transmitters 256. In some embodiments, a dose counter 118 may include one or more dose counter processors 258. Accordingly, in some embodiments, a dose counter 118 may transmit one or more signals 114. In some embodiments, a dose counter 118 may receive one or more signals 114. In some embodiments, a dose counter 118 may process one or more signals 114.

In some embodiments, a dose counter 118 may be a mechanical dose counter 248. For example, in some embodiments, a mechanical dose 248 counter may include a ratchet mechanism that advances a numerical indicator every time that an inhaler is activated to dispense an ethanol-containing inhalant 214 (see e.g., Wright et al., Dispending apparatus, U.S. Pat. No. 8,689,785 and Kaar et al., Dose counter for a metered-dose inhaler, U.S. Pat. No. 8,662,381; herein incorporated by reference). In some embodiments, a mechanical dose 248 counter may include a ratchet mechanism that advances a numerical indicator every time that an inhaler is activated to release an agent 222. In some embodiments, a mechanical dose 248 counter may include a ratchet mechanism that advances a numerical indicator every time that an inhaler is activated to release propellant 218. In some embodiments, a dose counter 118 may be an electronic dose counter 250 that includes an electronic display that displays the number of times that an inhaler is activated to dispense an ethanol-containing inhalant 214, an agent 222, and/or release propellant 218 (e.g., Solomon et al., Dose counter and recording method, U.S. Pat. No. 8,539,945; herein incorporated by reference). In some embodiments, a dose counter 118 may be an audio dose counter 252 that includes an audio display. In some embodiments, an audio display may be configured to indicate the number of times that an inhaler is activated to dispense an ethanol-containing inhalant 214, an agent 222, and/or propellant 218. For example, in some embodiments, an audio dose counter 252 may receive information associated with the number of times that an inhaler has been activated to release an ethanol-containing inhalant 214, an agent 222, and/or propellant 218 and provide an audio display in the form of a human voice to report the information.

In some embodiments, a dose counter 118 may be operably coupled with and receive information from one or more sensors 116. In some embodiments, a dose counter 118 may be operably coupled with and receive information from one or more control units 110. In some embodiments, a dose counter 118 may receive information associated with the quantity of an ethanol-containing inhalant 214, an agent 222, and/or propellant 218 that is contained within an inhalant reservoir 212, an agent reservoir 220, and/or a propellant reservoir 216 and then display the information. In some embodiments, a dose counter 118 may receive information associated with the quantity of an ethanol-containing inhalant 214, an agent 222, and/or propellant 218 that is released through one or more flow channels 104 and then display the information.

Indicator Device

With continued reference to FIGS. 1-4C, in some embodiments, system 100 may include one or more indicator devices 120. Indicator devices 120 may be configured in numerous ways. In some embodiments, an indicator device 120 may include one or more indicator receivers 156. In some embodiments, an indicator device 120 may include one or more indicator transmitters 158. Accordingly, in some embodiments, an indicator device 120 may transmit one or more signals 114. In some embodiments, an indicator device 120 may receive one or more signals 114. In some embodiments, an indicator device 120 may include one or more indicator processors 160. Accordingly, in some embodiments, an indicator device 120 may process information.

In some embodiments, an indicator device 120 may include a display 148. An indicator device 120 may include numerous types of displays 148. Examples of such displays 148 include, but are not limited to, visual displays 150, audio displays 152, tactile displays 154, and the like. Examples of visual displays 150 include, but are not limited to, electronic visual displays 150 such as active displays and passive displays. In some embodiments, a visual display 150 may be contained within a mobile device such as a cellular telephone, a personal digital assistant, a notepad computer, and the like. Accordingly, in some embodiments, a control unit 110 may be configured to transmit information that is received by and displayed on a mobile device. In some embodiments, a sensor 116 may be configured to transmit information that is received by and displayed on a mobile device. In some embodiments, information may be displayed on a head mounted display 148 such as an optical head-mounted display 148. In some embodiments, an indicator device 120 may include a tactile display 154 that is configured to vibrate. For example, in some embodiments, an indicator device 120 may vibrate with an intensity that is related to the amount of an ethanol-containing inhalant 214 flowing through one or more flow channels 104 disposed within an inhaler. In some embodiments, an indicator device 120 may include an audio display 152 that is configured to emit one or more sounds. For example, in some embodiments, an indicator device 120 may have a tone that is related to the amount of an ethanol-containing inhalant 214 flowing through one or more flow channels 104 disposed within an inhaler. An indicator device 120 may display information that is related to numerous parameters associated with an inhaler. For example, in some embodiments, an indicator device 120 may indicate one or more levels of flow of an ethanol-containing inhalant 214 through a flow channel 104. In some embodiments, an indicator device 120 may indicate one or more levels of a vacuum applied to a flow channel 104 by a subject using the inhaler. In some embodiments, an indicator device 120 may indicate a volume of gas flowing through a flow channel 104. In some embodiments, an indicator device 120 may indicate a velocity with which gas flows through a flow channel 104. Accordingly, an indicator device 120 may be configured to display information that is related to numerous parameters.

In some embodiments, an indicator device 120 may be operably coupled with one or more control units 110. In some embodiments, an indicator device 120 may be operably coupled with one or more sensors 116. In some embodiments, an indicator device 120 may be operably coupled with one or more control units 110 and one or more sensors 116. In some embodiments, an indicator device 120 may be configured to display processed information that is received from a control unit 110. For example, in some embodiments, an indicator device 120 may indicate a quantity of an ethanol-containing inhalant 214 that flows through a flow channel 104. In some embodiments, an indicator device 120 may indicate a quantity of an agent 222 that flows through a flow channel 104.

Sensor

As further shown in FIGS. 1-4C, in some embodiments, system 100 may include one or more sensors 116. System 100 may include numerous types of sensors 116. Examples of sensors 116 include, but are not limited to, flow sensors 126 such as gas flow sensors 126 and liquid flow sensors 126, volume sensors 130, optical sensors 128, pressure sensors 132, vacuum sensors 134, velocimeters 138, ultrasonic flow meters 140, and the like. In some embodiments, a sensor 126 may be configured as an ethanol sensor 136. Numerous types of ethanol sensors 136 may be utilized. Examples of such ethanol sensors 136 include, but are not limited to, transdermal ethanol sensors 136, fuel-cell ethanol sensors 136, electrochemical ethanol sensors 136, semiconductor ethanol sensors 136, and the like. In some embodiments, a sensor 126 may be configured to detect an ethanol metabolite. In some embodiments, a sensor 116 may be configured as a biometric sensor 116. For example, in some embodiments, a sensor may be a retinal scanner, a fingerprint scanner, a facial recognition device, and the like. Accordingly, in some embodiments, such sensors may be used to identify a subject using an inhaler. In some embodiments, such identification can be used to prevent release of an ethanol-containing inhalant 214 to a disapproved subject. In some embodiments, such identification can be used to facilitate release of an ethanol-containing inhalant 214 to an approved subject.

In some embodiments, a sensor 116 may include one or more sensor receivers 144. In some embodiments, a sensor 116 may include one or more sensor transmitters 142. In some embodiments, a sensor 116 may receive one or more signals 114. In some embodiments, a sensor 116 may transmit one or more signals 114. In some embodiments, a sensor 116 may include one or more sensor processors 146. Accordingly, in some embodiments, a sensor 116 may process information. In some embodiments, an ethanol sensor 136 may be remote from an inhaler. For example, in some embodiments, an ethanol sensor 136 may assess ethanol concentration and then transmit one or more signals that include the information. Such information may be received by one or more control units 110, one or more display devices 120, one or more actuators 122, and/or one or more user interfaces 112.

In some embodiments, one or more sensors 116 may be operably coupled with one or more flow channels 104 that are disposed within a housing 102. In some embodiments, a sensor 116 may be configured to measure the velocity with which gas flows through a flow channel 104. In some embodiments, a sensor 116 may be configured to measure the velocity with which liquid flows through a flow channel 104. In some embodiments, a volume sensor 130 may be used to measure a volume of gas flowing through a flow channel 104. In some embodiments, a volume sensor 130 may be used to measure a volume of liquid flowing through a flow channel 104. In some embodiments, a sensor 116 may be configured to measure a quantity of an ethanol-containing inhalant 214 that flows through a flow channel 104. In some embodiments, a sensor 116 may be configured to measure a quantity of an agent 222 that flows through a flow channel 104. In some embodiments, a vacuum sensor 134 may be used to measure an amount of vacuum pressure applied to a flow channel 104. In some embodiments, a pressure sensor 132 may be used to measure an amount of gas pressure applied to a flow channel 104. In some embodiments, a pressure sensor 132 may be operably coupled to a mouthpiece 192 of an inhaler and configured to assess the quality of physical contact between the mouth of a subject and the mouthpiece. Accordingly, in some embodiments, such a pressure sensor 132 may be configured to measure stress and/or strain on the mouthpiece 192.

In some embodiments, a sensor 116 may be operably coupled with one or more control units 110. Accordingly, in some embodiments, a control unit 110 may be configured to control the operation of one or more operably coupled sensors 116. In some embodiments, a sensor 116 may be operably coupled with one or more actuators 122 that are configured to facilitate at least partial release of contents from one or more reservoirs 124. For example, in some embodiments, a sensor 116 may be operably coupled to an actuator 122 and configured to facilitate at least partial release of an ethanol-containing inhalant 214 from an inhalant reservoir 212 in a manner that is dependent on the quantity of an ethanol-containing inhalant 214 detected flowing through a flow channel 104. In some embodiments, a sensor 116 may be coupled to a control unit 110 and to an actuator 122. Accordingly, in some embodiments, a control unit 110 may receive detected information from one or more sensors 116 and then control one or more actuators 122 in response to the information. Accordingly, in some embodiments, a feedback loop may be used to release one or more ethanol-containing inhalants 214, one or more agents 222, and/or combinations thereof into one or more flow channels 104.

In some embodiments, a sensor 116 may be configured to detect blood sugar levels. For example, in some embodiments, a sensor 116 may be configured as a transdermal sensor 116 that is able to detect the blood sugar level within a subject. Accordingly, in some embodiments, a control unit 110 may receive information associated with the blood sugar level detected within an subject and regulate the amount of an ethanol-containing inhalant 214 that is dispensed to the subject in response to the detected blood sugar level associated with the subject. In some embodiments, a control unit 110 may correlate the blood sugar level detected within a subject with an amount of food that was consumed by a subject. Accordingly, in some embodiments, a control unit 110 may be configured to regulate the amount of an ethanol-containing inhalant 214 that is dispensed to the subject in response to the determined amount of food consumed by the subject.

User Interface

With continued reference to FIGS. 1-4C, in some embodiments, system 100 may include one or more user interfaces 112. System 100 may include numerous types of user interfaces 112. Examples of user interfaces 112 include, but are not limited to, graphical interfaces 162, monitors 166, touchscreens 172, touchpads 170, keyboards 168, mobile device interfaces 164, user displays 174, and the like. In some embodiments, a user interface 112 may include one or more user transmitters 176. In some embodiments, a user interface 112 may include one or more user receivers 178. In some embodiments, a user interface 112 may include one or more interface processors 182. In some embodiments, a user interface 112 may include interface memory 180. Accordingly, in some embodiments, a user interface 112 may transmit one or more signals 114, receive one or more signals 114, and process one or more signals 114.

In some embodiments, a user interface 112 may transmit one or more signals 114 that are received by one or more control units 110. In some embodiments, a user interface 112 may transmit one or more signals 114 that are received by one or more sensors 116. In some embodiments, a user interface 112 may transmit one or more signals 114 that are received by one or more indicator devices 120. In some embodiments, a user interface 112 may transmit one or more signals 114 that are received by one or more dose counters 118. In some embodiments, a user interface 112 may transmit one or more signals 114 that are received by one or more actuators 122.

In some embodiments, a user interface 112 may receive one or more signals 114 that are transmitted by one or more control units 110. In some embodiments, a user interface 112 may receive one or more signals 114 that are transmitted by one or more sensors 116. In some embodiments, a user interface 112 may receive one or more signals 114 that are transmitted by one or more indicator devices 120. In some embodiments, a user interface 112 may receive one or more signals 114 that are transmitted by one or more dose counters 118.

In some embodiments, a subject may enter information into a user interface 112 that transmits one or more signals 114 that include the information that are received by one or more control units 110. Examples of such information include, but are not limited to, information related to one or more of a subject's physical parameters, location parameters, time parameters, respiration parameters, information related to drugs used by the subject, information related to food ingested by the subject, information related to the time since food was last ingested, information related to blood sugar levels, information associated with a selected blood alcohol concentration to be reached, location information, legal information, and the like. In some embodiments, a subject may enter information into a user interface 112 that is associated with a choice of flavorant and/or ethanol-containing inhalant 214 that will be dispensed in association with food. For example, in some embodiments, a subject may select red wine and/or a red wine flavorant to be dispensed from a reservoir 124 during a meal. In some embodiments, a subject may select whiskey to be dispensed from a reservoir 124 while the subject smokes a cigar. In some embodiments, a control unit 110 may regulate the amount of an ethanol-containing inhalant 214 that is dispense in a manner that is dependent upon an amount of food consumed by a subject.

Signal

Numerous types of signals 116 may be used within system 100. Examples of such signals 116 include, but are not limited to, wireless signals 228, optical signals 230, magnetic signals 232, radiofrequency signals 236, hardwired signals 238, infrared signals 240, audible signals 242, analog signals 246, digital signals 244, Bluetooth signals 234, and the like. Accordingly, system 100 may include receivers, transmitters, and processors that are configured to receive, transmit, and process numerous types of signals 116. A signal 116 may include numerous types of information. For example, in some embodiments, a signal 116 may include information associated with one or more respiration parameters. In some embodiments, a signal 116 may include information associated with release of an ethanol-containing inhalant 214 from an inhalant reservoir 212. In some embodiments, a signal 116 may include information associated with release of an agent 222 from an agent reservoir 220. In some embodiments, a signal 116 may include information associated with release of propellant 218 from a propellant reservoir 216.

Control Unit

As further depicted in FIGS. 1-4C, in some embodiments, system 100 may include one or more control units 110. In some embodiments, a control unit 110 may include one or more control computers 206. In some embodiments, a control unit 110 may include one or more control receivers 194. In some embodiments, a control unit 110 may include one or more control transmitters 196. In some embodiments, a control unit 110 may include one or more control processors 198. In some embodiments, a control unit 110 may include control memory 204. In some embodiments, a control unit 110 may include control logic 200. In some embodiments, a control unit 110 may include concentration logic 202. In some embodiments, a control unit 110 may include one or more power supplies 208. In some embodiments, a control unit 110 may include one or more control interfaces 210.

In some embodiments, a control unit 110 may receive one or more signals 114 that are transmitted by one or more user interfaces 112. In some embodiments, a control unit 110 may receive one or more signals 114 that are transmitted by one or more sensors 116. In some embodiments, a control unit 110 may receive one or more signals 114 that are transmitted by one or more indicator devices 120. In some embodiments, a control unit 110 may receive one or more signals 114 that are transmitted by one or more dose counters 118. In some embodiments, a control unit 110 may receive one or more signals 114 that are transmitted by one or more actuators 122.

In some embodiments, a control unit 110 may transmit one or more signals 114 that are received by one or more user interfaces 112. In some embodiments, a control unit 110 may transmit one or more signals 114 that are received by one or more sensors 116. In some embodiments, a control unit 110 may transmit one or more signals 114 that are received by one or more actuators 122. In some embodiments, a control unit 110 may transmit one or more signals 114 that are received by one or more indicator devices 120. In some embodiments, a control unit 110 may transmit one or more signals 114 that are received by one or more dose counters 118.

In some embodiments, a control unit 110 may transmit one or more signals 114 that direct the operation of one or more actuators 122. For example, in some embodiments, a control unit 110 may transmit one or more signals 114 that direct an actuator 122 to at least partially release contents from one or more reservoirs 124. In some embodiments, a control unit 110 may transmit one or more signals 114 that direct an actuator 122 not to release contents from one or more reservoirs 124. For example, in some embodiments, a control unit 110 may receive information from one or more sensors 116 that is related to location information. In some embodiments, a control unit 110 may receive location information from a global positioning system interface 280. The control unit 110 may direct an actuator 122 not to release contents from one or more reservoirs 124 if an inhaler is in an impermissible location. In some embodiments, the control unit 110 may direct an actuator 122 to release contents from one or more reservoirs 124 if an inhaler is in a permissible location. In some embodiments, the control unit 110 may direct an actuator 122 not to release contents from one or more reservoirs 124 if an inhaler is moving at or above a certain rate. For example, in some embodiments, the control unit 110 may direct an actuator 122 not to release contents from one or more reservoirs 124 if an inhaler is moving at a rate consistent with travelling in an automobile. In some embodiments, a control unit 110 may direct one or more actuators 122 to at least partially release contents from one or more reservoirs 124 during an inhalation cycle through an inhaler and then direct the one or more actuators 122 to not release contents from the one or more reservoirs 124 during an exhalation cycle through an inhaler. In some embodiments, a control unit 110 may direct the operation of more than one actuator 122. For example, in some embodiments, a control unit 110 may direct a first actuator 122 to at least partially release an ethanol-containing inhalant 214 from an inhalant reservoir 212 and then direct a second actuator 122 to at least partially release propellant 218 from a propellant reservoir 216. In some embodiments, a control unit 110 may direct a first actuator 122 to at least partially release an ethanol-containing inhalant 214 from an inhalant reservoir 212 and direct a second actuator 122 to at least partially release propellant 218 from a propellant reservoir 216 at substantially the same time.

In some embodiments, a control unit 110 may transmit one or more signals 114 that are received by one or more indicator devices 120. In some embodiments, a control unit 110 may receive one or more signals 114 from one or more sensors 116 that include information related to a quantity of an ethanol-containing inhalant 214 that flowed through a flow channel 104. In some embodiments, the control unit 110 may then transmit one or more signals 114 that are received by one or more indicator devices 120 that direct the one or more indicator devices 120 to indicate the quantity of the ethanol-containing inhalant 214 that flowed through a flow channel 104. In some embodiments, a control unit 110 may transmit one or more signals 114 that are received by one or more indicator devices 120 that direct the one or more indicator devices 120 to indicate a quantity of an ethanol-containing inhalant 214 that needs to be released from an inhalant reservoir 212 to reach a predetermined blood alcohol concentration.

In some embodiments, a control unit 110 may receive one or more signals 114 that are transmitted by one or more dose counters 118. For example, in some embodiments, a control unit 110 may receive one or more signals 114 that include information related to the quantity of an ethanol-containing inhalant 214 that has been released from an inhalant reservoir 212.

In some embodiments, a control unit 110 may compare one or more parameters to one or more threshold levels that are associated with the one or more parameters. For example, in some embodiments, a control unit 110 may receive one or more assessed values from one or more sensors 116 that are associated with the blood alcohol concentration of a subject using an inhaler. The control unit 110 may compare the one or more assessed values to one or more threshold values that are associated with the blood alcohol concentration to determine if the one or more assessed values are below, meet or exceed the one or more threshold values. In some embodiments, a control unit 110 may compare one or more assessed values that are related to one or more parameters to one or more ranges of levels associated with the one or more parameters. In some embodiments, a control unit 110 may compare one or more assessed values that are related to one or more parameters to one or more ranges of levels associated with the one or more parameters to determine in the one or more assessed values are within the one or more ranges of levels associated with the one or more parameters. For example, in some embodiments, a control unit 110 may receive one or more signals 114 transmitted by one or more sensors 116 that include one or more assessed values associated with the blood alcohol concentration of a subject using an inhaler. The control unit 110 may compare the one or more assessed values to one or more ranges of values that are associated with the blood alcohol concentration to determine if the one or more assessed values are within the one or more ranges of values.

Blood alcohol concentration is indicated as weight of alcohol per unit volume of blood. Exemplary ranges of the blood alcohol concentration include, but are not limited to, about 0 to about 0.02, about 0 to about 0.04, about 0 to about 0.06, about 0 to about 0.08, about 0 to about 0.10, about 0 to about 0.12, about 0 to about 0.14, about 0 to about 0.16, about 0 to about 0.18, about 0 to about 0.20, about 0 to about 0.22, about 0 to about 0.24, and about 0 to about 0.26.

In some embodiments, a control unit 110 may compare a threshold value to a determined value associated with the blood alcohol concentration of a subject using an inhaler and then calculate a quantity of ethanol-containing inhalant 214 to be released to achieve or exceed the threshold value. For example, in some embodiments, a control unit 110 may receive information associated with the weight and gender of a subject using an inhaler and use that information in combination with the assessed blood alcohol concentration of the subject to calculate an additional quantity of an ethanol-containing inhalant 214 to be released to reach a selected blood alcohol concentration in the subject. In some embodiments, a control unit 110 may be configured to determine a relationship associated with two or more concentrations of ethanol assessed at two or more times and direct operation of the at least one actuator 122 to release a quantity of an ethanol-containing inhalant 214 from an operably coupled ethanol-containing inhalant reservoir 212 based on the relationship.

In some embodiments, a control unit 110 may utilize parameters associated with a subject using an inhaler to calculate a quantity of ethanol-containing inhalant 214 to be released. Examples of such parameters include, but are not limited to, physical parameters associated with a subject (e.g., height, weight, gender), physiological parameters associated with a subject (e.g., alcohol metabolism), psychological parameters of a subject (e.g., depression), identity parameters of a subject, age parameters of a subject, occupancy parameters of a subject (e.g., the presence of absence of other parties in the vicinity of the subject), motion parameters associated with a subject (e.g., travelling in an automobile), ethanol use parameters associated with a subject, time parameters associated with a subject, location parameters associated with a subject, legal parameters associated with a subject (e.g., court orders), activity parameters associated with a subject, consumption parameters associated with a subject, flavoring parameters associated with a subject (e.g., flavor selected by a subject), and the like.

In some embodiments, a control unit 110 may receive information related to one or more parameters associated with a subject from a device associated with the subject 125 (see FIG. 1). Such devices may be configured in numerous ways. Examples of such configurations include, but are not limited to, bracelets, badges, cellular telephones, and the like. In some embodiments, a control unit 110 may receive information associated with the blood alcohol concentration of a subject from a transdermal ethanol sensor 136 that transmits one or more signals 114 that include the information and are received by a control unit 110. In some embodiments, a control unit 110 may receive information associated with the blood alcohol concentration of a subject from a breathalyzer that transmits one or more signals 114 that include the information and are received by a control unit 110. In some embodiments, a control unit 110 may receive information associated with one or more parameters associated with a subject from a database.

In some embodiments, a control unit 110 can create an ethanol delivery regimen associated with a subject. In some embodiments, a control unit 110 can create an ethanol delivery regimen associated with a subject in response to one or more parameters. For example, in some embodiments, a control unit 110 may determine one or more quantities of an ethanol-containing inhalant 214 to dispense. In some embodiments, a control unit 110 may determine one or more quantities of an ethanol-containing inhalant 214 to dispense at one or more times. In some embodiments, a control unit 110 may determine one or more rates to dispense an ethanol-containing inhalant 214. In some embodiments, a control unit 110 may determine one or more times to dispense an ethanol-containing inhalant 214. In some embodiments, a control unit 110 may determine one or more times not to dispense an ethanol-containing inhalant 214. In some embodiments, a control unit 110 may determine one or more particle sizes in which to deliver an ethanol-containing inhalant 214. In some embodiments, a control unit 110 may determine one or more particle sizes in which to deliver an ethanol-containing inhalant 214 to one or more portions of a subject's pulmonary tract. In some embodiments, a control unit 110 may determine one or more particle sizes in which to deliver an ethanol-containing inhalant 214 to a subject's upper pulmonary tract. In some embodiments, a control unit 110 may determine one or more particle sizes in which to deliver an ethanol-containing inhalant 214 to a subject's middle pulmonary tract. In some embodiments, a control unit 110 may determine one or more particle sizes in which to deliver an ethanol-containing inhalant 214 to a subject's lower pulmonary tract.

In some embodiments, a control unit 110 may select one or more ethanol-containing inhalant 214 formulations for delivery to a subject. In some embodiments, a control unit 110 may select one or more ethanol-containing inhalant 214 formulations for delivery to a subject having an immediate release profile. In some embodiments, a control unit 110 may select one or more ethanol-containing inhalant 214 formulations for delivery to a subject having a substantially immediate release profile. In some embodiments, a control unit 110 may select one or more ethanol-containing inhalant 214 formulations for delivery to a subject having a substantially delayed release profile. In some embodiments, a control unit 110 may select one or more ethanol-containing inhalant 214 formulations for delivery to a subject having a substantially sustained release profile. In some embodiments, a control unit 110 may select one or more ethanol-containing inhalant 214 formulations for delivery to a subject having a substantially immediate release profile and a substantially sustained release profile.

In some embodiments, a control unit 110 may select one or more preexisting ethanol-containing inhalant delivery regimens. In some embodiments, a control unit 110 may select one or more preexisting ethanol-containing inhalant delivery regimens from a table, a catalog, a database, a list, and the like. In some embodiments, a control unit 110 may select one or more preexisting ethanol-containing inhalant delivery regimens for a specific subject. In some embodiments, a control unit 110 may select one or more ethanol-containing inhalant delivery regimens in response to input received from a subject.

In some embodiments, a control unit 110 may be configured to controllably dispense an ethanol-containing inhalant 214 from an inhaler according to an ethanol delivery regimen. In some embodiments, a control unit 110 may control one or more actuators 122 to facilitate at least partial release of an ethanol-containing inhalant 214 from one or more inhalant reservoirs 212 according to an ethanol delivery regimen. In some embodiments, a control unit 110 may control one or more actuators 122 to facilitate at least partial release of an ethanol-containing inhalant 214 from one or more inhalant reservoirs 212 at one or more permissible times. In some embodiments, a control unit 110 may prevent one or more actuators 122 from releasing an ethanol-containing inhalant 214 from one or more inhalant reservoirs 212 at one or more impermissible times. In some embodiments, a control unit 110 may control one or more actuators 122 to facilitate at least partial release of an ethanol-containing inhalant 214 from one or more inhalant reservoirs 212 to one or more approved subjects. In some embodiments, a control unit 110 may control one or more actuators 122 to prevent release of an ethanol-containing inhalant 214 from one or more inhalant reservoirs 212 to one or more disapproved subjects. In some embodiments, a control unit 110 may control one or more actuators 122 to facilitate at least partial release of an ethanol-containing inhalant 214 from one or more inhalant reservoirs 212 at one or more determined times.

In some embodiments, a control unit 110 may control one or more actuators 122 to facilitate at least partial release of an ethanol-containing inhalant 214 from one or more inhalant reservoirs 212 that contain inhalant having one or more determined particle sizes. In some embodiments, a control unit 110 may control one or more actuators 122 to facilitate at least partial release of an ethanol-containing inhalant 214 from one or more inhalant reservoirs 212 through one or more screens to create one or more particle sizes. In some embodiments, a control unit 110 may control one or more actuators 122 to facilitate at least partial release of an ethanol-containing inhalant 214 from one or more inhalant reservoirs 212 through one or more ultrasonic nozzles to create one or more particle sizes. In some embodiments, a control unit 110 may control one or more ultrasonic nozzles to create ethanol-containing inhalant 214 particles having an approximate desired diameter. Examples of such particle sizes include, but are not limited to, diameters that are between about 0.5 micrometers and about 4 micrometers, between about 1 micrometer and about 4 micrometers, between about 4 micrometers and about 10 micrometers, between about 10 micrometers and about 30 micrometers, and the like.

In some embodiments, a control unit 110 may control one or more actuators 122 to facilitate at least partial release of an ethanol-containing inhalant 214 from one or more inhalant reservoirs 212 that contain ethosomes. In some embodiments, a control unit 110 may control one or more actuators 122 to facilitate at least partial release of an ethanol-containing inhalant 214 from one or more inhalant reservoirs 212 that contain liposomes.

In some embodiments, a control unit 110 may control one or more actuators 122 to facilitate at least partial release of an ethanol-containing inhalant 214 from one or more inhalant reservoirs 212 that contain inhalant formulations having a desired release profiles. For example, in some embodiments, a control unit 110 may select an inhalant reservoir 212 that contains an ethanol-containing inhalant formulation having a desired release profile and then control one or more actuators 122 to facilitate release from the selected inhalant reservoir 212.

In some embodiments, a control unit 110 may control one or more actuators 122 that are configured to facilitate at least partial release of ethanol-containing inhalant 214 from one or more inhalant reservoirs 212 to reach a selected blood alcohol concentration. For example, in some embodiments, the blood alcohol concentration of a subject using an inhaler may be determined to be below a value of 0.05. A control unit 110 may compare the determined blood alcohol concentration to a value and then calculate a quantity of ethanol-containing inhalant 214 for release that will increase the blood alcohol concentration of the subject to a selected level. In some embodiments, a control unit 110 may use parameters associated with the subject to make such a calculation. For example, in some embodiments, a control unit 110 may use the gender and weight of a subject in combination with available information that correlates gender, weight, and ethanol intake to blood alcohol concentration and use the correlation to determine an additional quantity of ethanol-containing inhalant 214 to dispense to the subject to reach a selected blood alcohol concentration. In some embodiments, a control unit 110 may correlate the quantity of ethanol-containing inhalant 214 that was administered to a subject to the blood alcohol concentration of the subject assessed at two or more times and use the correlation to determine an addition quantity of ethanol-containing inhalant 214 to dispense to the subject to reach a selected blood alcohol concentration in the subject. Accordingly, in some embodiments, the control unit 110 may control one or more actuators 122 to facilitate at least partial release of ethanol-containing inhalant 214 from one or more inhalant reservoirs 212 to meet a selected blood alcohol concentration value. In some embodiments, a control unit 110 may control one or more actuators 122 to prevent release of ethanol-containing inhalant 214 from one or more inhalant reservoirs 212 if the blood alcohol concentration of a subject using the inhaler meets or exceeds a threshold value.

In some embodiments, a control unit 110 may control one or more actuators 122 that are configured to facilitate at least partial release of an agent 222 from an agent reservoir 220. In some embodiments, a control unit 110 may control one or more actuators 122 that are configured to facilitate at least partial release of an agent 222 from one or more agent reservoirs 220 to deliver a selected quantity of agent 222 to a subject using an inhaler. In some embodiments, a control unit 110 may receive one or more signals 114 from one or more sensors 116 that include information related to a quantity of an agent 222 that flowed through a flow channel 104. The control unit 110 may then determine an additional quantity of agent 222 to be released from an agent reservoir 220. Accordingly, in some embodiments, a feedback loop may be used to dispense an agent 222 until a selected quantity of the agent 222 is dispensed.

In some embodiments, a control unit 110 may control one or more actuators 122 that are configured to facilitate at least partial release of propellant 218 from a propellant reservoir 220. In some embodiments, a control unit 110 may control one or more actuators 122 that are configured to facilitate at least partial release of propellant 218 from one or more propellant reservoirs 218 to release a predetermined quantity of propellant 218 into a flow channel 104. In some embodiments, a control unit 110 may receive one or more signals 114 from one or more sensors 116 that include information related to a quantity of propellant 218 flowing through a flow channel 104. The control unit 110 may then determine an additional quantity of propellant 218 to be released from a propellant reservoir 216. Accordingly, in some embodiments, a feedback loop may be used to release propellant 218 until a selected quantity of the propellant 218 is released.

In some embodiments, a control unit 110 may be configured to select one or more ethanol-containing inhalants 214 to dispense in response to information associated with food being consumed by a subject. For example, in some embodiments, a control unit 110 may receive one or more signals 114 from a user interface 112 indicating that a subject is having a steak dinner. Accordingly, in some embodiments, a control unit 110 may select a reservoir 124 that includes a red wine flavored ethanol-containing inhalant 214. In some embodiments, a control unit 110 may select an agent reservoir 220 that includes a red wine flavorant and facilitate release of the wine flavorant with an ethanol-containing inhalant 214. Accordingly, in some embodiments, a control unit 110 may be programmed to select one or more ethanol-containing inhalants 214 and/or one or more flavorants that are paired with food being consumed by a subject.

Figures 5, 5B:
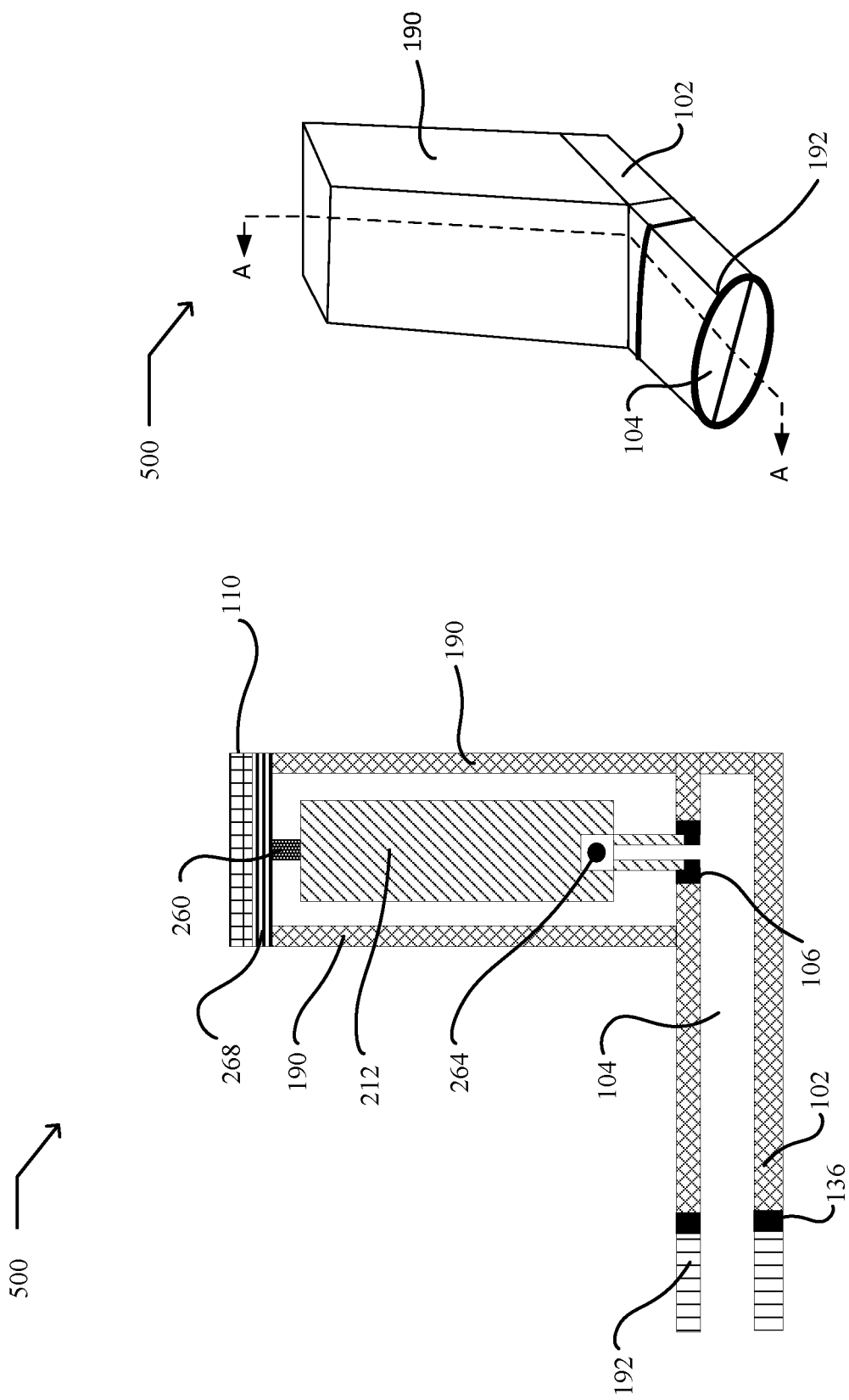
FIG. 5 illustrates a cross-sectional partial side view of an example inhaler 500 (as viewed along view A-A of FIG. 5B) in which embodiments may be implemented.
FIG. 5B illustrates a perspective partial front view of an example inhaler 500 in which embodiments may be implemented.

FIG. 5 illustrates a partial cross-sectional side view of system 500 that is configured as an embodiment of an inhaler. System 500 includes a housing 102 having a flow channel 104 disposed therein. The housing is illustrated as being operably coupled with a mouthpiece 192. Also illustrated is a port 106 disposed in the housing 102 in fluid communication with the flow channel 104. An ethanol-containing inhalant reservoir 212 is illustrated as being operably coupled to port 106. The ethanol-containing inhalant reservoir 212 is illustrated as being held within a reservoir support 190. The ethanol-containing inhalant reservoir 212 is configured as an aerosol canister that includes a canister body and a valve stem that extends from the canister body into port 106. The ethanol-containing inhalant reservoir 212 includes a controllable valve 264. The controllable valve 264 is illustrated as being closed as indicated by a closed circle. An ethanol sensor 136 is operably coupled to the flow channel 104 and configured to detect ethanol flowing through the flow channel 104. An aerosol canister content release mechanism 268 is illustrated with a pushrod actuator 260 operably coupled with the ethanol-containing inhalant reservoir 212. The aerosol canister content release mechanism 268 is operably coupled with a control unit 110. The control unit 110 is configured to direct operation of the aerosol canister content release mechanism 268 to control the pushrod actuator 260 to facilitate at least partial release from the ethanol-containing inhalant reservoir 212. The control unit 110 is operably coupled with the ethanol sensor 136. Accordingly, in some embodiments, ethanol sensor 136 may be configured to detect a quantity of ethanol-containing inhalant 214 flowing through the flow channel 104 during use of the inhaler by a subject. Accordingly, in some embodiments, such information may be transmitted to the control unit 110 that may use the information to calculate a quantity of ethanol-containing inhalant 214 that needs to be administered to the subject to reach a selected blood alcohol concentration. The control unit 110 may then control operation of the aerosol canister content release mechanism 268 to release an additional quantity of ethanol-containing inhalant 214 to reach the selected blood alcohol concentration.

Figure 5A:
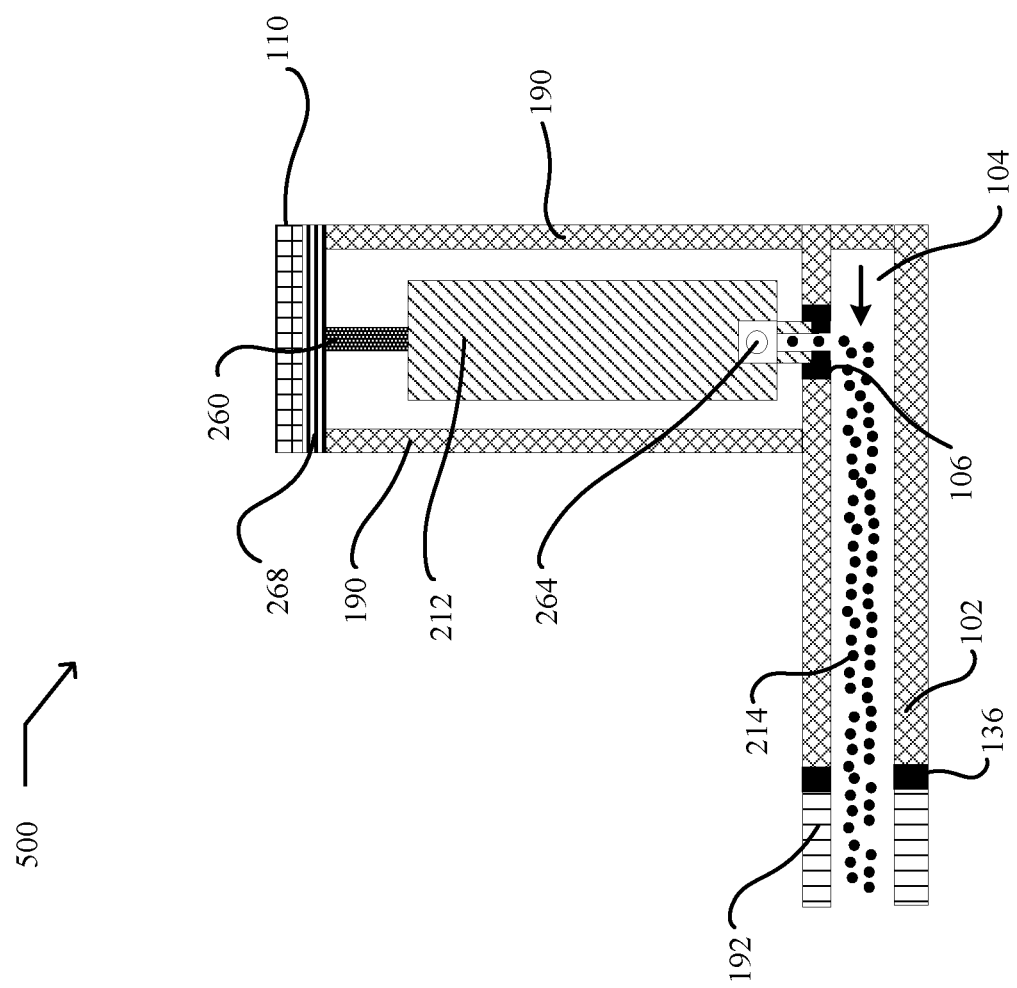
FIG. 5A illustrates a cross-sectional partial side view of an example inhaler 500 (as viewed along view A-A of FIG. 5B) in which embodiments may be implemented.

FIG. 5A illustrates a partial cross-sectional side view of system 500 in which the inhaler is illustrated as being activated to at least partially release ethanol-containing inhalant 214 from the inhalant reservoir 212. The controllable valve 264 that is operably coupled to the inhalant reservoir 212 is illustrated as being open as indicated by an open circle. Flow through the flow channel 104 is illustrated by an arrow indicating right to left flow of ethanol-containing inhalant 214 toward mouthpiece 192 through the flow channel 104. An aerosol canister content release mechanism 268 is illustrated with the pushrod actuator 260 being activated to facilitate at least partial release of ethanol-containing inhalant 214 from the inhalant reservoir 212. In the activated state, the pushrod actuator 256 compresses the canister body of the inhalant reservoir 212 toward the valve stem that extends from the canister body to facilitate at least partial release of ethanol-containing inhalant 214 from the inhalant reservoir 212 through port 106 and into the flow channel 104.

Figure 6:
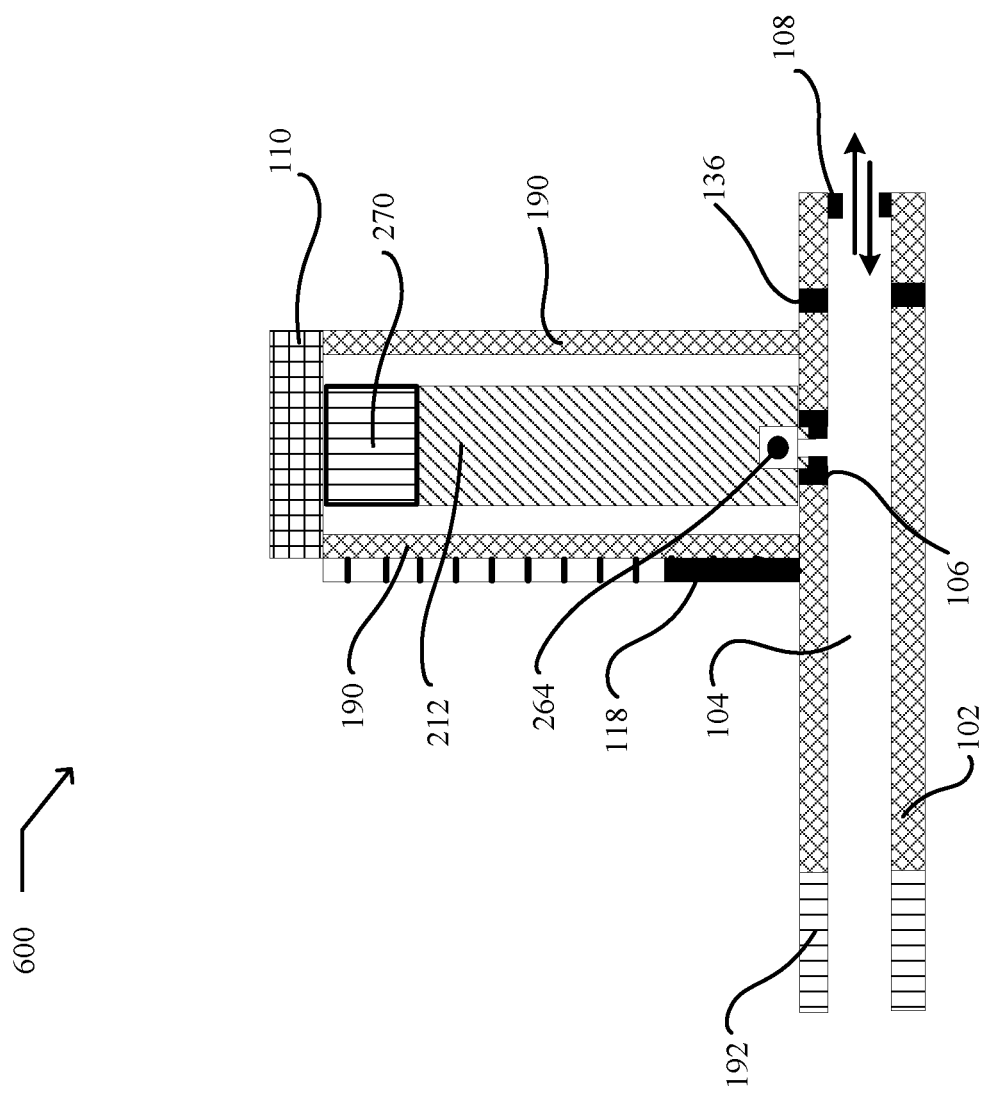
FIG. 6 illustrates a cross-sectional partial side view of an example inhaler 600 (as viewed along view A-A of FIG. 5B) in which embodiments may be implemented.

FIG. 6 illustrates a partial cross-sectional side view of system 600 that is configured as an embodiment of an inhaler that includes a housing 102 having a flow channel 104 disposed therein. The housing 102 is operably coupled to mouthpiece 192. Also illustrated is a port 106 disposed in the housing 102 in fluid communication with the flow channel 104. An inhalant reservoir 212 is illustrated as being operably coupled to the port 106. The inhalant reservoir 212 is illustrated as being held within a reservoir support 190. The inhalant reservoir 212 is operably coupled to heater 270. The inhalant reservoir 212 includes a controllable valve 264 that is illustrated as being closed as indicated by a closed circle. Flow through the flow channel 104 is illustrated by two arrows pointing in opposite directions indicating bidirectional flow through the flow channel 104. A flow valve 108 is operably coupled to the flow channel 104 and configured to control flow through the flow channel 104. The flow valve 108 is illustrated in the open position to allow bidirectional flow through the flow channel 104. The heater 270 is operably coupled with a control unit 110. The control unit 110 is configured to direct operation of the heater 270 and the controllable valve 264 to facilitate at least partial release from the inhalant reservoir 212. The control unit 110 is operably coupled with an ethanol sensor 136. Accordingly, in some embodiments, control unit 110 may be configured to control operation of the heater 270 and the controllable valve 264 to at least partially release ethanol-containing inhalant 214 from the inhalant reservoir 212 in response to information received from the ethanol sensor 136. A dose counter 118 is illustrated as showing the quantity of ethanol-containing inhalant 214 remaining in the inhalant reservoir 212.

Figure 6A:
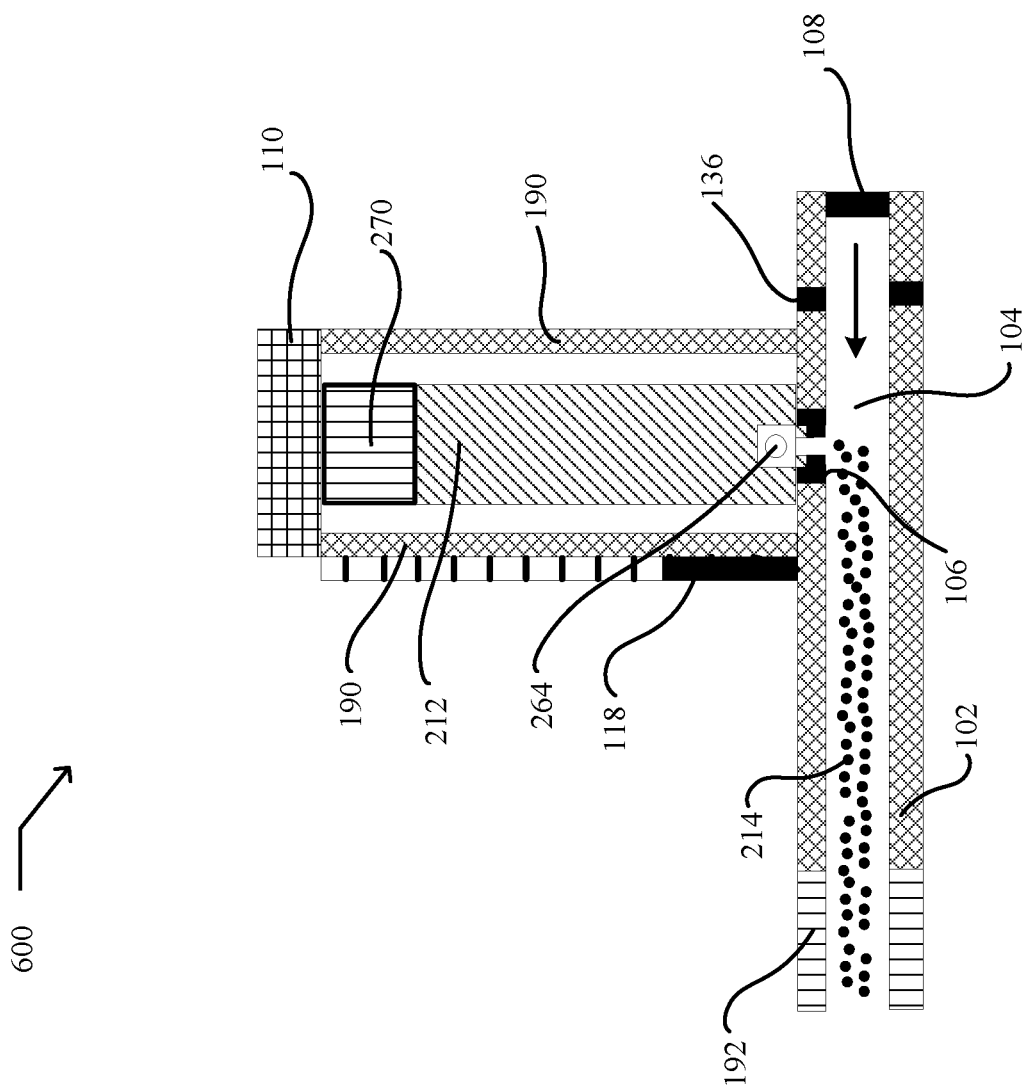
FIG. 6A illustrates a cross-sectional partial side view of an example inhaler 600 (as viewed along view A-A of FIG. 5B) in which embodiments may be implemented.

FIG. 6A illustrates a partial cross-sectional side view of system 600 in which the inhaler is illustrated as being activated to at least partially release ethanol-containing inhalant 214 from the inhalant reservoir 212. The controllable valve 264 that is operably coupled to the inhalant reservoir 212 is illustrated as being open as indicated by an open circle. Flow of ethanol-containing inhalant 214 through the flow channel 104 is illustrated by an arrow pointing from right to left through the flow channel 104 toward the mouthpiece 192. A flow valve 108 is illustrated as being in a closed state to direct the flow of ethanol-containing inhalant 214 through the flow channel 104 disposed within the inhaler toward the mouthpiece 192. In some embodiments, the flow valve 108 may be operably coupled with control unit 110. In some embodiments, the flow valve 108 may be operably coupled with sensor 116. In some embodiments, the flow valve 108 may be operably coupled with control unit 110 and a sensor 116.

Figure 7:
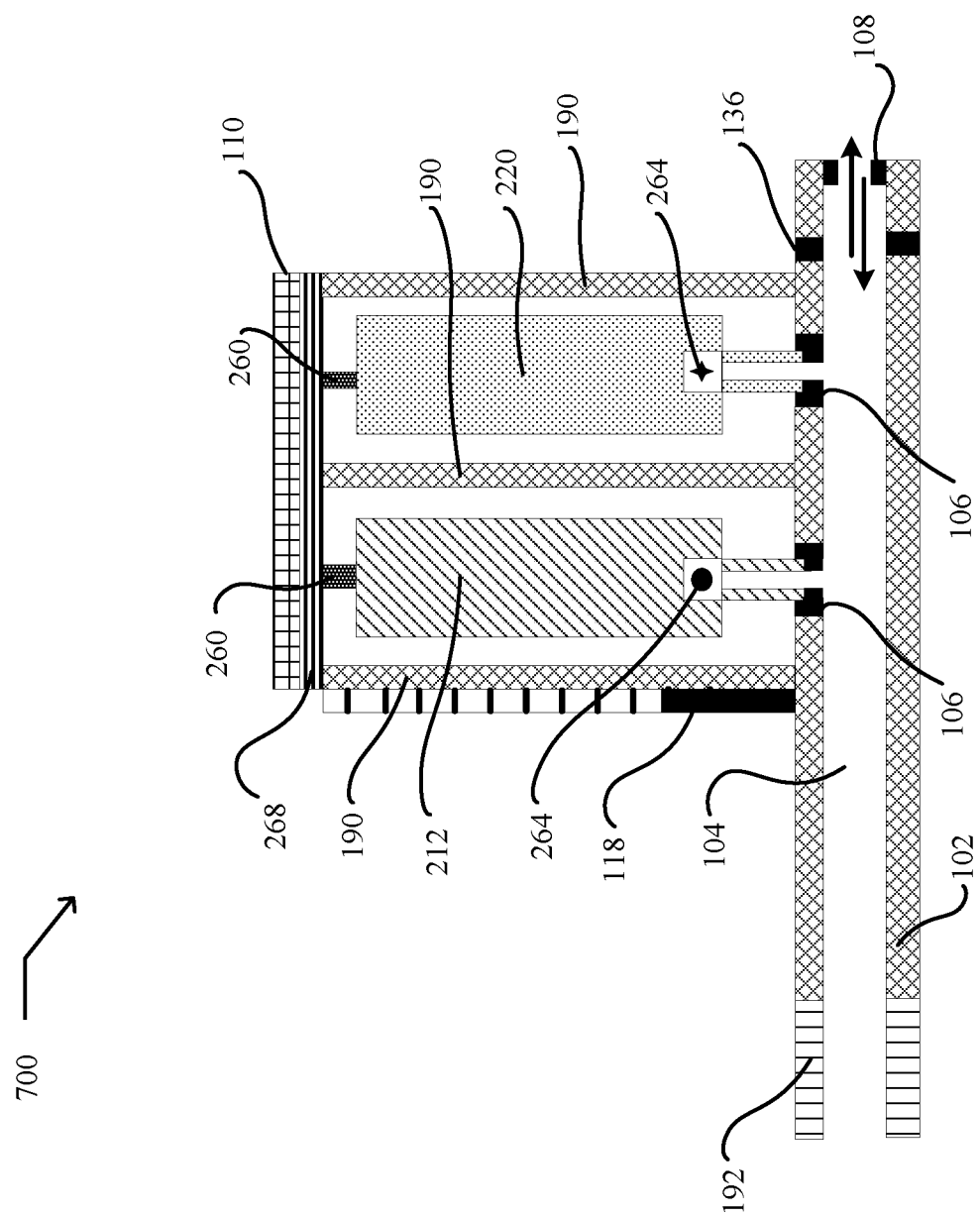
FIG. 7 illustrates a cross-sectional partial side view of an example inhaler 700 (as viewed along view A-A of FIG. 5B) in which embodiments may be implemented.

FIG. 7 illustrates a partial cross-sectional side view of system 700. System 700 is shown as an embodiment of an inhaler that includes a housing 102 having a flow channel 104 disposed therein. Also illustrated are two ports 106 disposed in the housing 102 in fluid communication with the flow channel 104. An inhalant reservoir 212 is illustrated as being operably coupled to one of the ports 106. An agent reservoir 220 is illustrated as being operably coupled to the other port 106. The inhalant reservoir 212 and the agent reservoir 220 are illustrated as being held within a reservoir support 190. The inhalant reservoir 212 and the agent reservoir 220 are configured as aerosol canisters that include a canister body and a valve stem that each extend from the canister body into each of the ports 106. The inhalant reservoir 212 and the agent reservoir 220 include controllable valves 264. The controllable valves 264 are illustrated as being closed as indicated by a closed circle and a closed star. Flow through the flow channel 104 is illustrated by two arrows pointing in opposite directions indicating bidirectional flow through the flow channel 104. A flow valve 108 is operably coupled to the flow channel 104 and configured to control flow through the flow channel 104. The flow valve 108 is illustrated in the open position to allow bidirectional flow through the flow channel 104. An aerosol canister content release mechanism 268 is illustrated with two pushrod actuators 260 that are operably coupled with each of the inhalant reservoir 212 and the agent reservoir 220. The aerosol canister content release mechanism 268 is operably coupled with a control unit 110. The control unit 110 is configured to direct operation of the aerosol canister content release mechanism 268 to control the pushrod actuators 260 to facilitate at least partial release from the inhalant reservoir 212 and the agent reservoir 220. The control unit 110 is operably coupled with an ethanol sensor 136. Accordingly, in some embodiments, the control unit 110 may be configured to facilitate at least partial release from one or both of the inhalant reservoir 212 and the agent reservoir 220 in response to information received from the ethanol sensor 136. In some embodiments, an ethanol sensor 136 may be configured to detect a concentration of ethanol in exhalant that flows through the flow channel 104 during use of the inhaler by a subject. Accordingly, in some embodiments, such concentration information may be transmitted to the control unit 110 that may use the information to calculate a quantity of ethanol-containing inhalant 214 to be released from an inhalant reservoir 212 to reach a selected blood alcohol concentration in a subject using the inhaler. The control unit 110 may then control operation of the aerosol canister content release mechanism 268 to facilitate release of a quantity of ethanol-containing inhalant 214 to reach the selected blood alcohol concentration. A dose indicator 118 is illustrated as showing a quantity of inhalant contained within the inhalant reservoir 212.

Figure 7A:
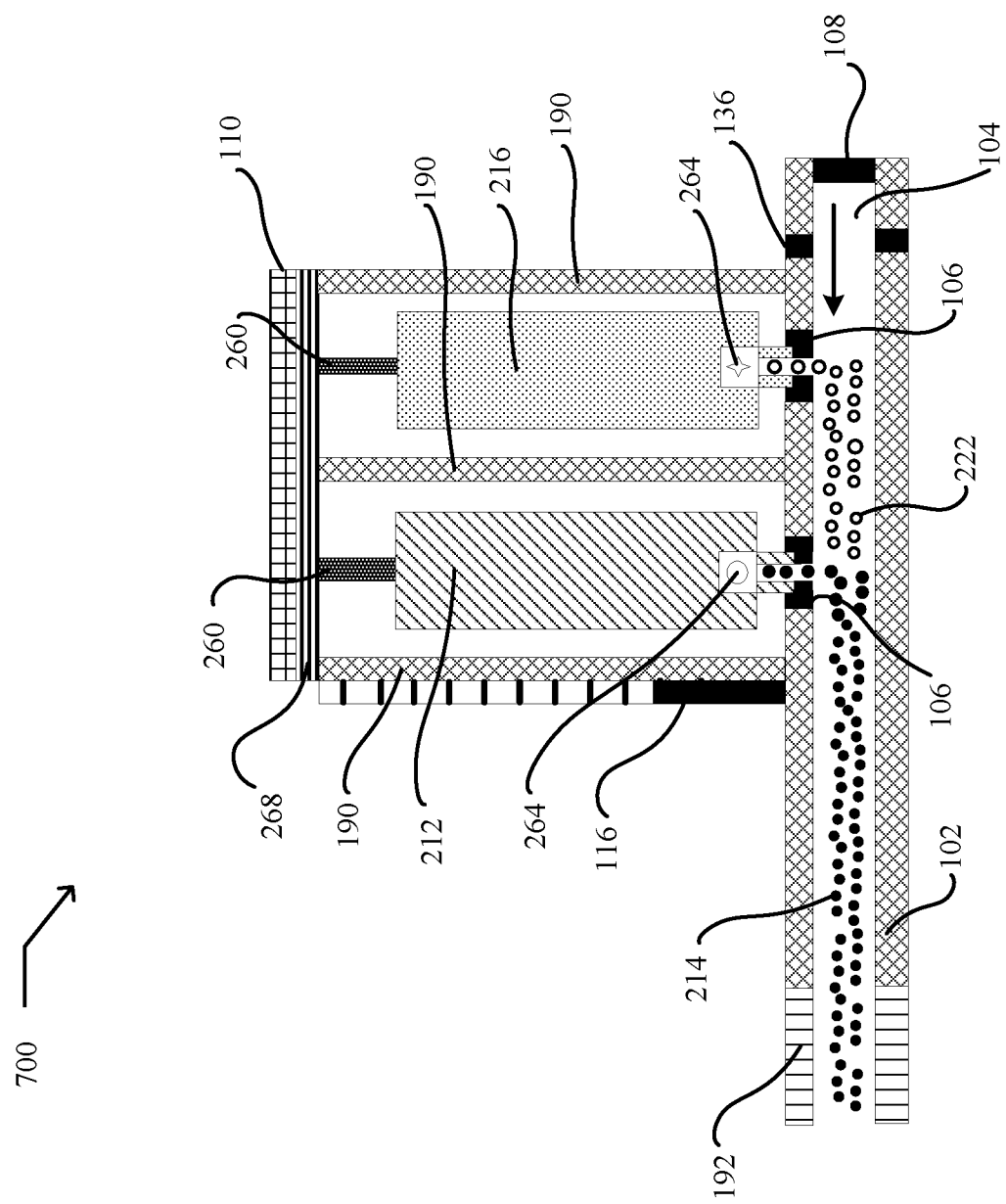
FIG. 7A illustrates a cross-sectional partial side view of an example inhaler 700 (as viewed along view A-A of FIG. 5B) in which embodiments may be implemented.

FIG. 7A illustrates a partial cross-sectional side view of system 700. System 700 is shown as an embodiment of an inhaler in an activated state to release ethanol-containing inhalant 214 and agent 222. The controllable valves 264 that are operably coupled with the inhalant reservoir 212 and the agent reservoir 216 are illustrated as being open as indicated by an open circle and an open star. The inhalant reservoir 212 and the agent reservoir 216 are illustrated as at least partially releasing ethanol-containing inhalant 214 and agent 222 that flow from right to left toward the mouthpiece 192 as indicated by the arrow. The pushrod actuators 260 are illustrated as depressing each of the aerosol canisters to at least partially release the ethanol-containing inhalant 212 and the agent 222. The flow valve 108 is illustrated as being in a closed state to direct the flow of ethanol-containing inhalant 214 and agent 222 through the flow channel 104 disposed within the inhaler toward the mouthpiece 192.

Figure 8:
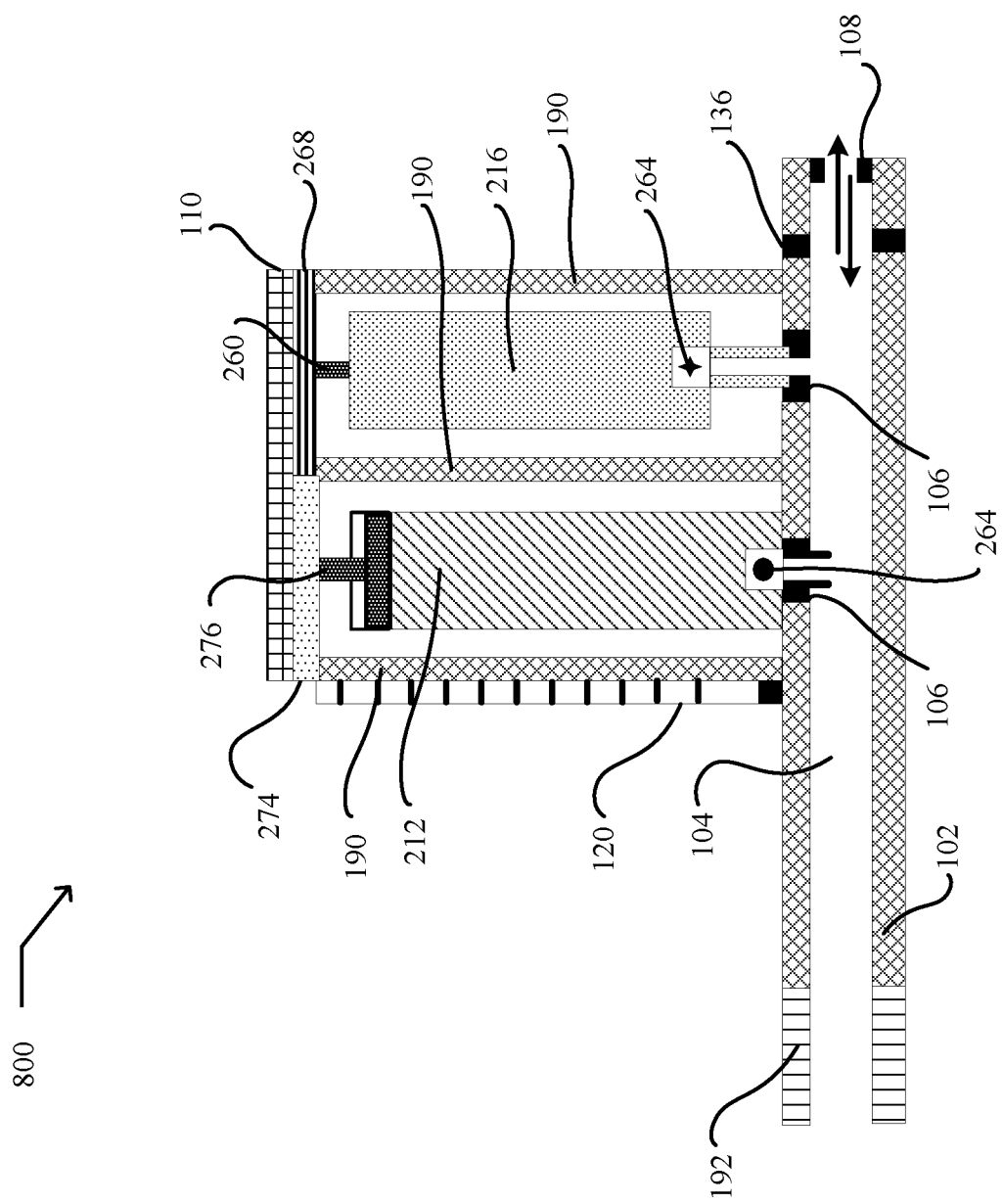
FIG. 8 illustrates a cross-sectional partial side view of an example inhaler 800 (as viewed along view A-A of FIG. 5B) in which embodiments may be implemented.

FIG. 8 illustrates a partial cross-sectional side view of system 800 that is configured as an embodiment of an inhaler that includes a housing 102 having a flow channel 104 disposed therein. A mouthpiece 192 is illustrated as being operably coupled with the housing 102. Also illustrated are two ports 106 disposed in the housing 102 in fluid communication with the flow channel 104. An inhalant reservoir 212 is illustrated as being operably coupled to one of the ports 106. A propellant reservoir 216 is illustrated as being operably coupled to the other port 106. The inhalant reservoir 212 and the propellant reservoir 216 are illustrated as being held within a reservoir support 190. The inhalant reservoir 212 is configured as a barrel that includes a plunger 276 that is operably coupled to a plunger actuator 274 that is configured to depress the plunger 276 to facilitate release of ethanol-containing inhalant 214 from the inhalant reservoir 212. The plunger actuator 274 is operably coupled to control unit 110 that is configured to control operation of the plunger actuator 274. The inhalant reservoir 212 includes a controllable valve 264. The controllable valve 264 is illustrated as being closed as indicated by a closed circle. The controllable valve 264 is operably coupled to control unit 110 that is configured to control operation of the controllable valve 264. The propellant reservoir 216 is configured as an aerosol canister with a canister body and a valve stem that extends from the canister body into port 106. An aerosol canister content release mechanism 268 is illustrated with a pushrod actuator 260 operably coupled with the propellant reservoir 216. The aerosol canister content release mechanism 268 is operably coupled with a control unit 110. The control unit 110 is configured to direct operation of the aerosol canister content release mechanism 268 to control the pushrod actuator 260 to facilitate at least partial release from the propellant reservoir 216. The control unit 110 is operably coupled with ethanol sensor 136. Flow through the flow channel 104 is illustrated by two arrows pointing in opposite directions indicating bidirectional flow through the flow channel 104. A flow valve 108 is operably coupled to the flow channel 104 and configured to control flow through the flow channel 104. The flow valve 108 is illustrated in the open position to allow bidirectional flow through the flow channel 104. The output device 120 is illustrated as indicating an assessed concentration of ethanol flowing through the flow channel 104.

FIG. 8A illustrates a partial cross-sectional side view of system 800 in an activated state to release ethanol-containing inhalant 214 and propellant 218 into the flow channel 104. The controllable valve 264 that is operably coupled to the inhalant reservoir 212 is illustrated as being open as indicated by an open circle. The plunger 276 is illustrated as being depressed into the barrel of the inhalant reservoir 212 to facilitate at least partial release of inhalant 214 into the flow channel 104. The controllable valve 264 that is operably coupled to the propellant reservoir 216 is illustrated as being open as indicated by an open star. The pushrod actuator 260 is illustrated as depressing the aerosol canister to at least partially release the propellant 218 into the flow channel 104. The flow valve 108 is illustrated as being in a closed state to direct the flow of ethanol-containing inhalant 214 and propellant 218 through the flow channel 104 disposed within the inhaler toward the mouthpiece 192.

FIG. 9 illustrates a partial cross-sectional side view of system 900 that is configured as an embodiment of an inhaler that includes a housing 102 having a flow channel 104 disposed therein. Also illustrated are two ports 106 disposed in the housing 102 in fluid communication with the flow channel 104. An inhalant reservoir 212 is illustrated as being operably coupled to one of the ports 106. A propellant reservoir 216 is illustrated as being operably coupled to the other port 106. The inhalant reservoir 212 and the propellant reservoir 216 are illustrated as being held within a reservoir support 190. The inhalant reservoir 212 is configured as a barrel that includes a plunger 276 that is operably coupled to a plunger actuator 274 that is configured to depress the plunger 276 to facilitate release of ethanol-containing inhalant 214 from the inhalant reservoir 212. The plunger actuator 274 is operably coupled to control unit 110 that is configured to control operation of the plunger actuator 274. The inhalant reservoir 212 includes a controllable valve 264. The controllable valve 264 is illustrated as being closed as indicated by a closed circle. The controllable valve 264 is operably coupled to control unit 110 that is configured to control operation of the controllable valve 264. The propellant reservoir 216 is configured as a compressed gas cylinder that is operably coupled to a regulator 266. The regulator 266 is operably coupled with a control unit 110 that is configured to control operation of the regulator 266 to facilitate at least partial release from the propellant reservoir 216. The control unit 110 is operably coupled with ethanol sensor 136. Flow through the flow channel 104 is illustrated by two arrows pointing in opposite directions indicating bidirectional flow through the flow channel 104. A flow valve 108 is operably coupled to the flow channel 104 and configured to control flow through the flow channel 104. The flow valve 108 is illustrated in the open position to allow bidirectional flow through the flow channel 104. The output device 120 is illustrated as indicating an assessed concentration of ethanol flowing through the flow channel 104.

Figure 9A:
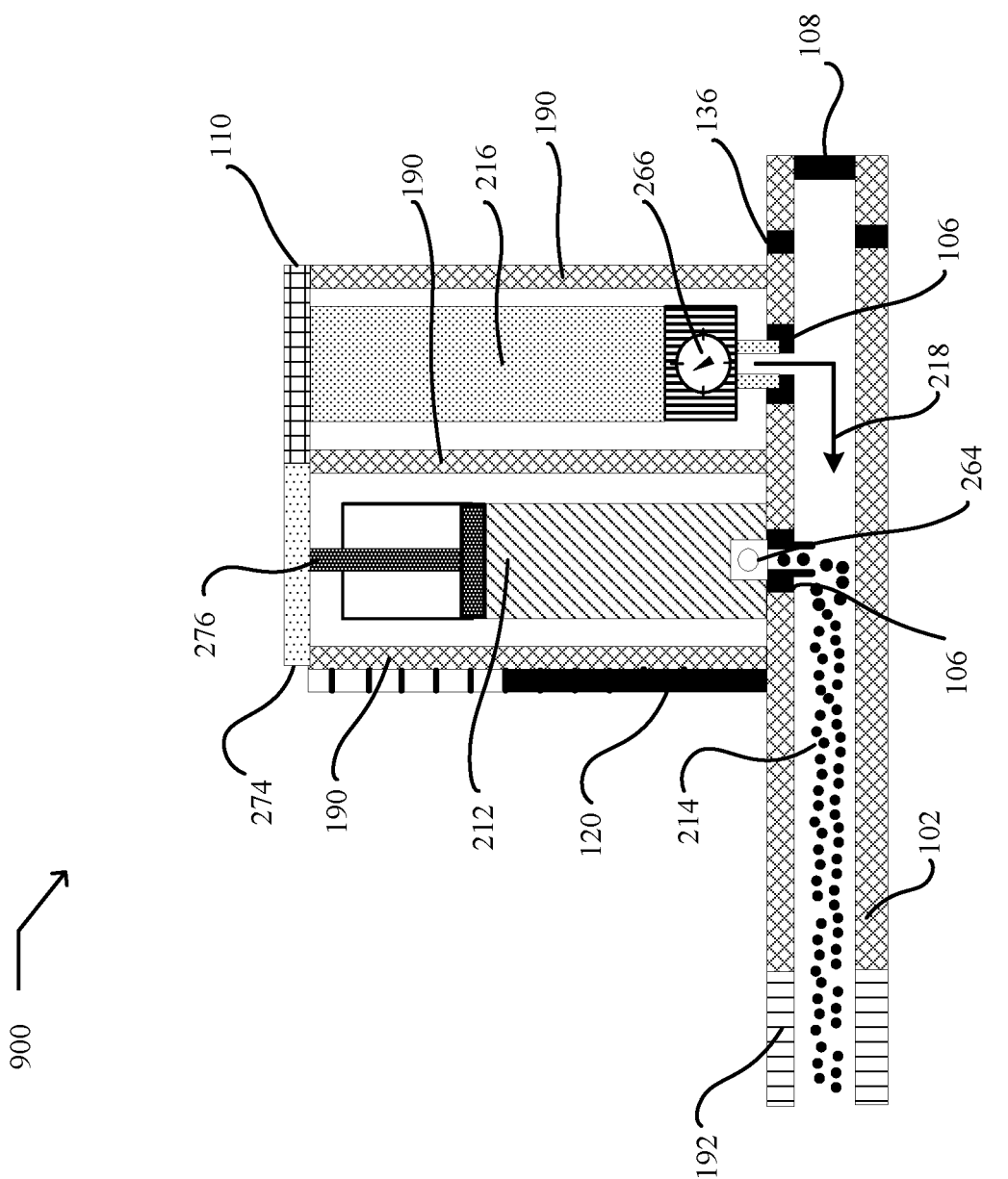
FIG. 9A illustrates a cross-sectional partial side view of an example inhaler 900 (as viewed along view A-A of FIG. 5B) in which embodiments may be implemented.

FIG. 9A illustrates a partial cross-sectional side view of system 900 in an activated state to release ethanol-containing inhalant 214 and propellant 218 into the flow channel 104. The controllable valve 264 that is operably coupled to the inhalant reservoir 212 is illustrated as being open as indicated by an open circle. The plunger 276 is illustrated as being depressed into the barrel of the inhalant reservoir 212 to facilitate at least partial release of inhalant 214 into the flow channel 104. The control unit 110 has directed the regulator 266 to at least partially release propellant 218 from the propellant reservoir 216. The flow valve 108 is illustrated as being in a closed state to direct the flow of ethanol-containing inhalant 214 and propellant 218 through the flow channel 104 disposed within the inhaler toward the mouthpiece 192.

Figure 10A:
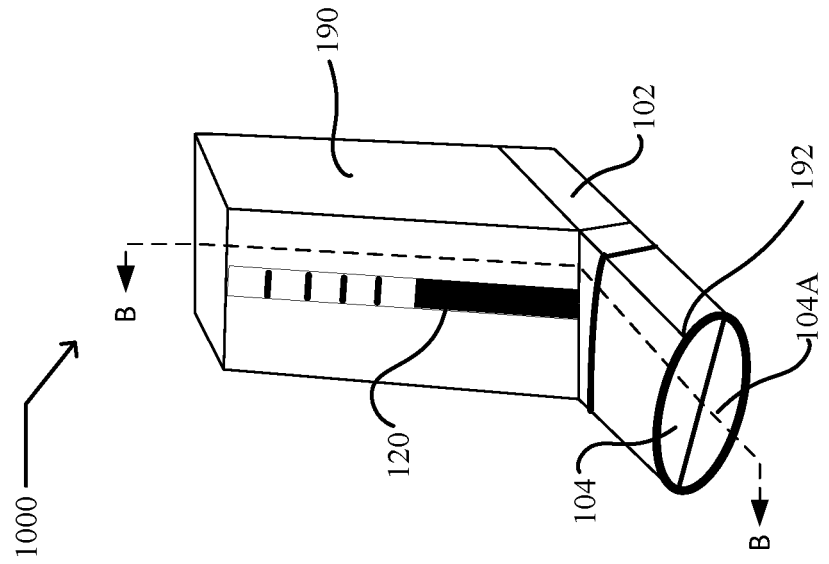
FIG. 10A illustrates a perspective partial front view of an example inhaler 1000 in which embodiments may be implemented.
Figure 10:
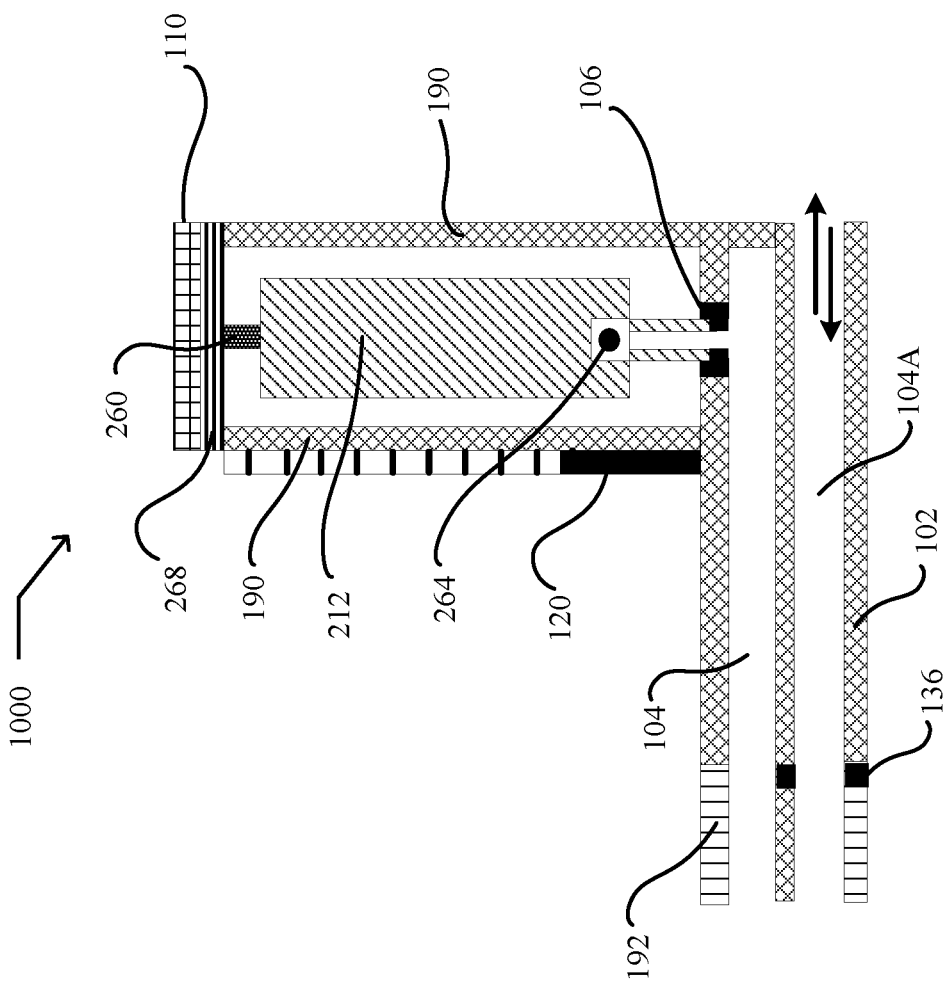
FIG. 10 illustrates a cross-sectional partial side view of an example inhaler 1000 (as viewed along view A-A of FIG. 5B) in which embodiments may be implemented.

FIG. 10 illustrates a partial cross-sectional side view of system 1000 that is configured as an embodiment of an inhaler. System 1000 includes a housing 102 having two flow channels 104 and 104A disposed therein. The housing 102 is illustrated as being operably coupled with a mouthpiece 192. Also illustrated is a port 106 disposed in the housing 102 in fluid communication with the flow channel 104. An ethanol-containing inhalant reservoir 212 is illustrated as being operably coupled to the port 106. The ethanol-containing inhalant reservoir 212 is illustrated as being held within a reservoir support 190. The ethanol-containing inhalant reservoir 212 is configured as an aerosol canister that includes a canister body and a valve stem that extends from the canister body into port 106. The ethanol-containing inhalant reservoir 212 includes a controllable valve 264. The controllable valve 264 is illustrated as being closed as indicated by a closed circle. An ethanol sensor 136 is operably coupled to flow channel 104A and configured to detect ethanol flowing through flow channel 104A. An aerosol canister content release mechanism 268 is illustrated with a pushrod actuator 260 operably coupled with the ethanol-containing inhalant reservoir 212. The aerosol canister content release mechanism 268 is operably coupled with a control unit 110. The control unit 110 is configured to direct operation of the aerosol canister content release mechanism 268 to control the pushrod actuator 260 to facilitate at least partial release from the ethanol-containing inhalant reservoir 212. The control unit 110 is operably coupled with the ethanol sensor 136. Ethanol sensor 136 may be configured to detect a concentration of ethanol flowing through flow channel 104A during use of the inhaler by a subject. Accordingly, in some embodiments, such information may be transmitted to the control unit 110 that may use the information to calculate a quantity of ethanol-containing inhalant 214 to be released to reach a selected blood alcohol concentration in a subject using the inhaler. The control unit 110 may then control operation of the aerosol canister content release mechanism 268 to release a quantity of ethanol-containing inhalant 214 to reach the selected blood alcohol concentration. The output device 120 is illustrated as indicating an assessed concentration of ethanol flowing through the flow channel 104A. Flow through the flow channel 104A is illustrated by two arrows pointing in opposite directions indicating bidirectional flow through the flow channel 104A.

FIG. 10A illustrates a perspective view of system 1000 that is configured as an embodiment of an inhaler. System 1000 includes a housing 102 having two flow channels 104 and 104A disposed therein. Also illustrated is a mouthpiece 192 that is operably coupled to flow channels 104 and 104A. System 1000 is illustrated as including a reservoir support 190 and an output device 120 that indicates an assessed concentration of ethanol flowing through the flow channel 104A.

Figure 10B:
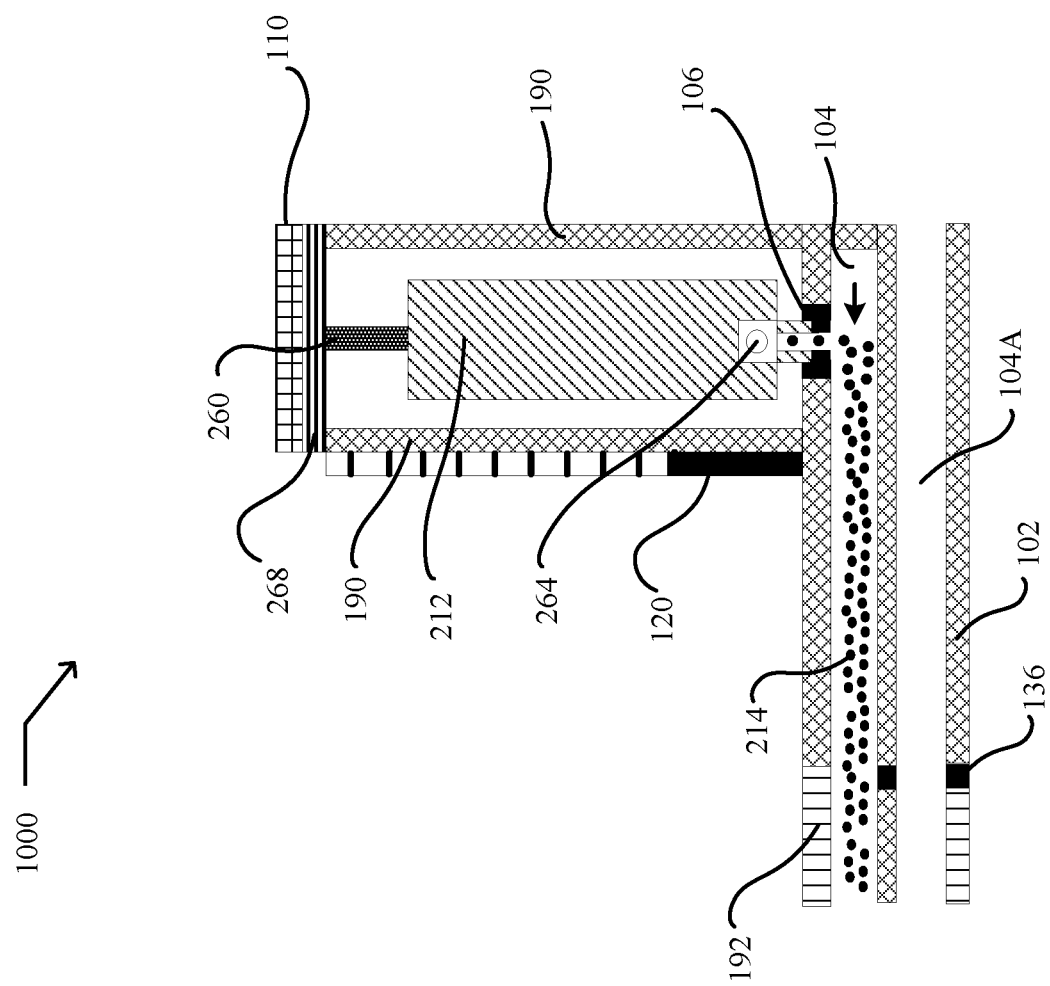
FIG. 10B illustrates a cross-sectional partial side view of an example inhaler 1000 (as viewed along view B-B of FIG. 10A) in which embodiments may be implemented.

FIG. 10B illustrates a partial cross-sectional side view of system 1000 in an activated state to release ethanol-containing inhalant 214 into flow channel 104. The controllable valve 264 that is operably coupled to the inhalant reservoir 212 is illustrated as being open as indicated by an open circle. An aerosol canister content release mechanism 268 is illustrated with the pushrod actuator 260 being activated to facilitate at least partial release of ethanol-containing inhalant 214 from the inhalant reservoir 212. In the activated state, the pushrod actuator 260 compresses the canister body of the inhalant reservoir 212 toward the valve stem that extends from the canister body to facilitate at least partial release of ethanol-containing inhalant 214 from the inhalant reservoir 212 through port 106 and into the flow channel 104. Flow through the flow channel 104 is from right to left toward mouthpiece 192 as indicated by the arrow.

Figure 11:
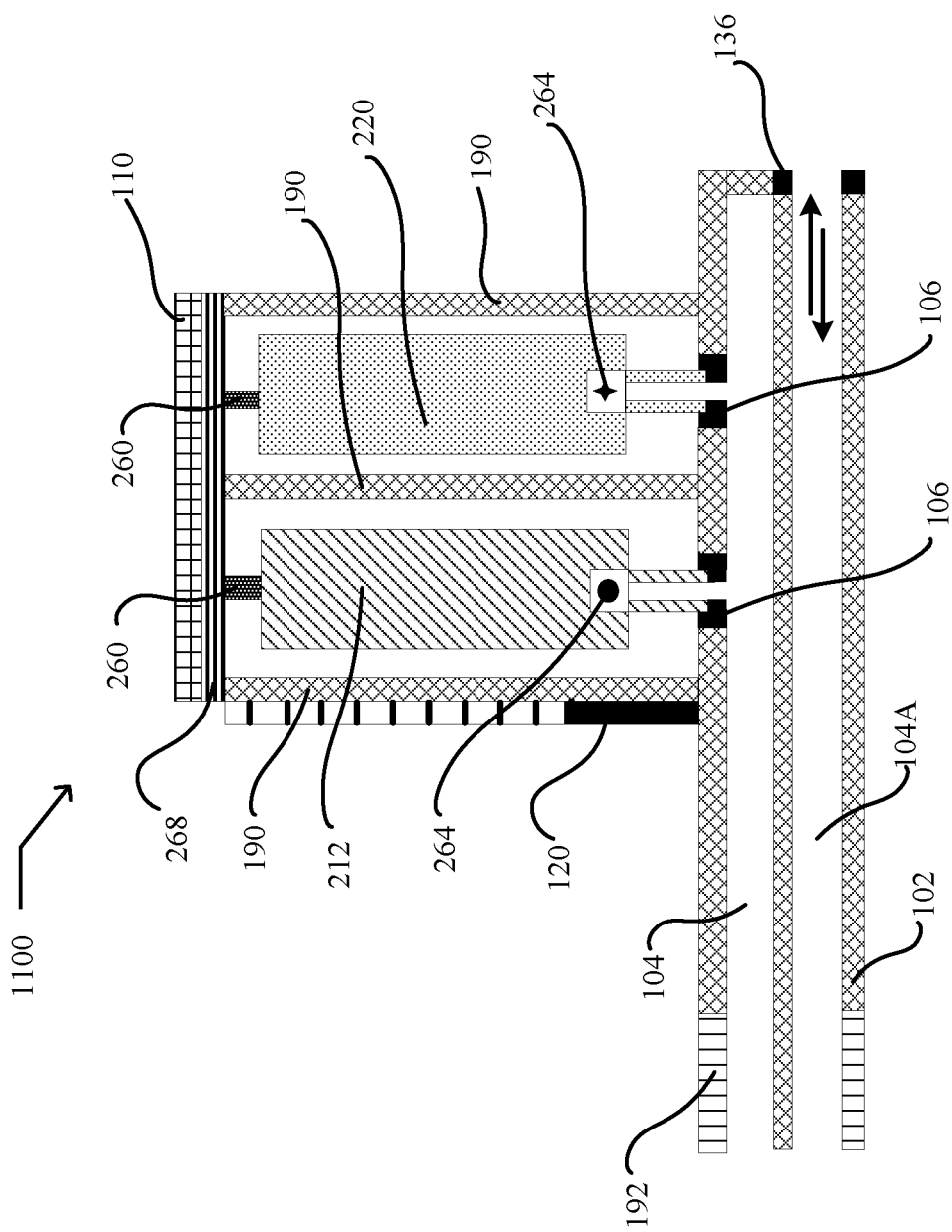
FIG. 11 illustrates a cross-sectional partial side view of an example inhaler 1100 (as viewed along view B-B of FIG. 10A) in which embodiments may be implemented.

FIG. 11 illustrates a partial cross-sectional side view of system 1100. System 1100 is shown as an embodiment of an inhaler that includes a housing 102 having flow channel 104 and flow channel 104A disposed therein. The housing 102 is illustrated as being operably coupled with a mouthpiece 192. Also illustrated are two ports 106 disposed in the housing 102 in fluid communication with the flow channel 104. An inhalant reservoir 212 is illustrated as being operably coupled to one of the ports 106. An agent reservoir 220 is illustrated as being operably coupled to the other port 106. The inhalant reservoir 212 and the agent reservoir 220 are illustrated as being held within a reservoir support 190. The inhalant reservoir 212 and the agent reservoir 220 are configured as aerosol canisters that include a canister body and a valve stem that each extend from the canister body into each of the ports 106. The inhalant reservoir 212 and the agent reservoir 220 include controllable valves 264. The controllable valves 264 are illustrated as being closed as indicated by a closed circle and a closed star. Flow through the flow channel 104A is illustrated by two arrows pointing in opposite directions indicating bidirectional flow through the flow channel 104A. An aerosol canister content release mechanism 268 is illustrated with a pushrod actuator 260 operably coupled with each of the inhalant reservoir 212 and the agent reservoir 220. The aerosol canister content release mechanism 268 is operably coupled with a control unit 110. The control unit 110 is configured to direct operation of the aerosol canister content release mechanism 268 to control the pushrod actuators 260 to facilitate at least partial release from the inhalant reservoir 212 and the agent reservoir 220. The control unit 110 is operably coupled with an ethanol sensor 136. Accordingly, in some embodiments, the control unit 110 may be configured to facilitate at least partial release from one or both of the inhalant reservoir 212 and the agent reservoir 220 in response to information received from the ethanol sensor 136. In some embodiments, an ethanol sensor 136 may be configured to detect a concentration of ethanol in exhalant that flows through flow channel 104A during use of the inhaler by a subject. Accordingly, in some embodiments, such concentration information may be transmitted to the control unit 110 that may use the information to calculate a quantity of ethanol-containing inhalant 214 to be released from an inhalant reservoir 212 to reach a selected blood alcohol concentration in a subject using the inhaler. The control unit 110 may then control operation of the aerosol canister content release mechanism 268 to facilitate release of a quantity of ethanol-containing inhalant 214 to reach the selected blood alcohol concentration. The indicator device 120 is illustrated as indicating an assessed concentration of ethanol flowing through the flow channel 104A.

Figure 11A:
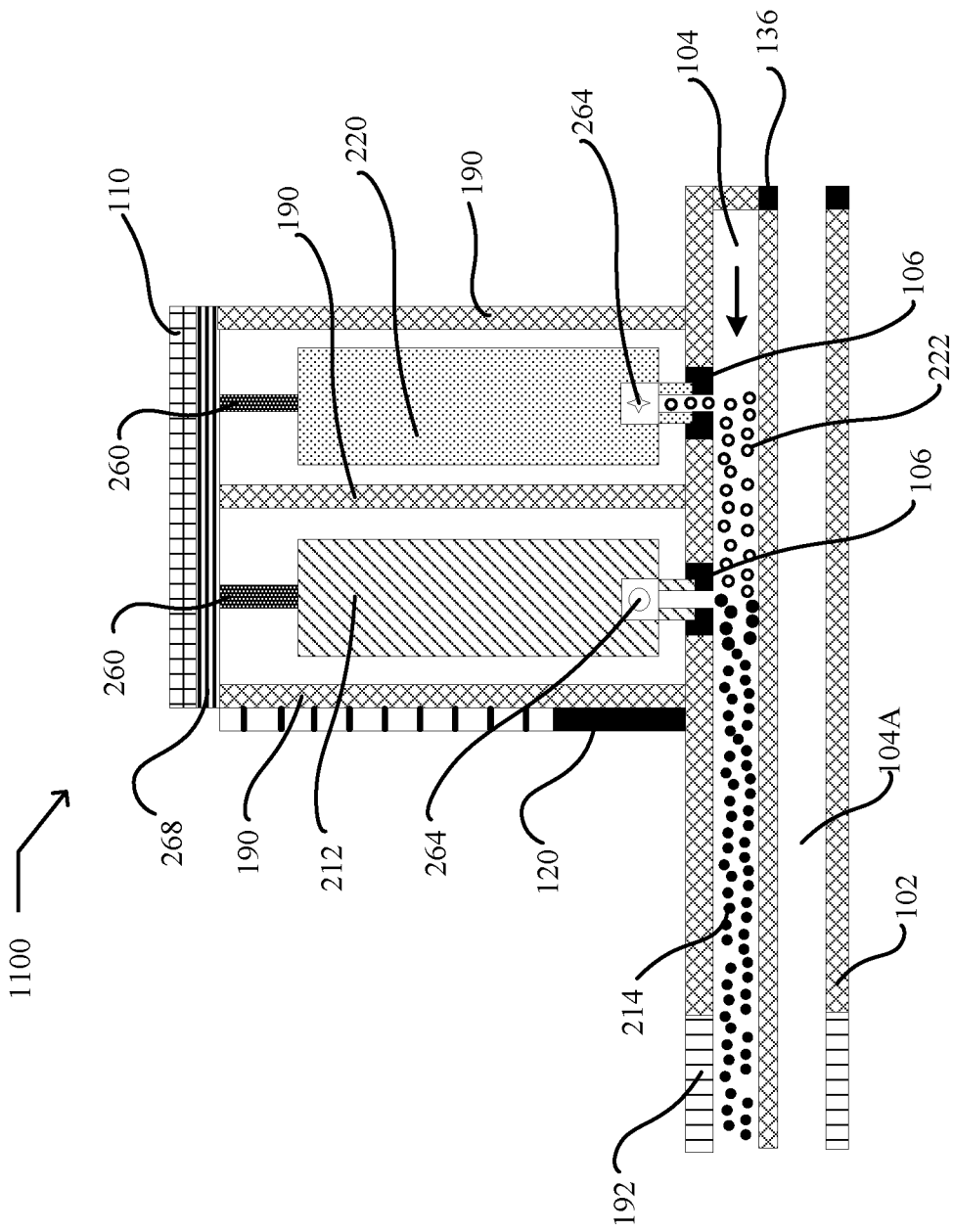
FIG. 11A illustrates a cross-sectional partial side view of an example inhaler 1100 (as viewed along view B-B of FIG. 10A) in which embodiments may be implemented.

FIG. 11A illustrates a partial cross-sectional side view of system 1100. System 1100 is shown as an embodiment of an inhaler in an activated state to release ethanol-containing inhalant 214 and agent 222. The controllable valves 264 that are operably coupled with the inhalant reservoir 212 and the agent reservoir 216 are illustrated as being open as indicated by an open circle and an open star. The inhalant reservoir 212 and the agent reservoir 216 are illustrated as at least partially releasing ethanol-containing inhalant 214 and agent 222 that flow from right to left toward the mouthpiece 192 as indicated by the arrow. The pushrod actuators 260 are illustrated as depressing each of the aerosol canisters to at least partially release the ethanol-containing inhalant 212 and the agent 222.

Figure 12:
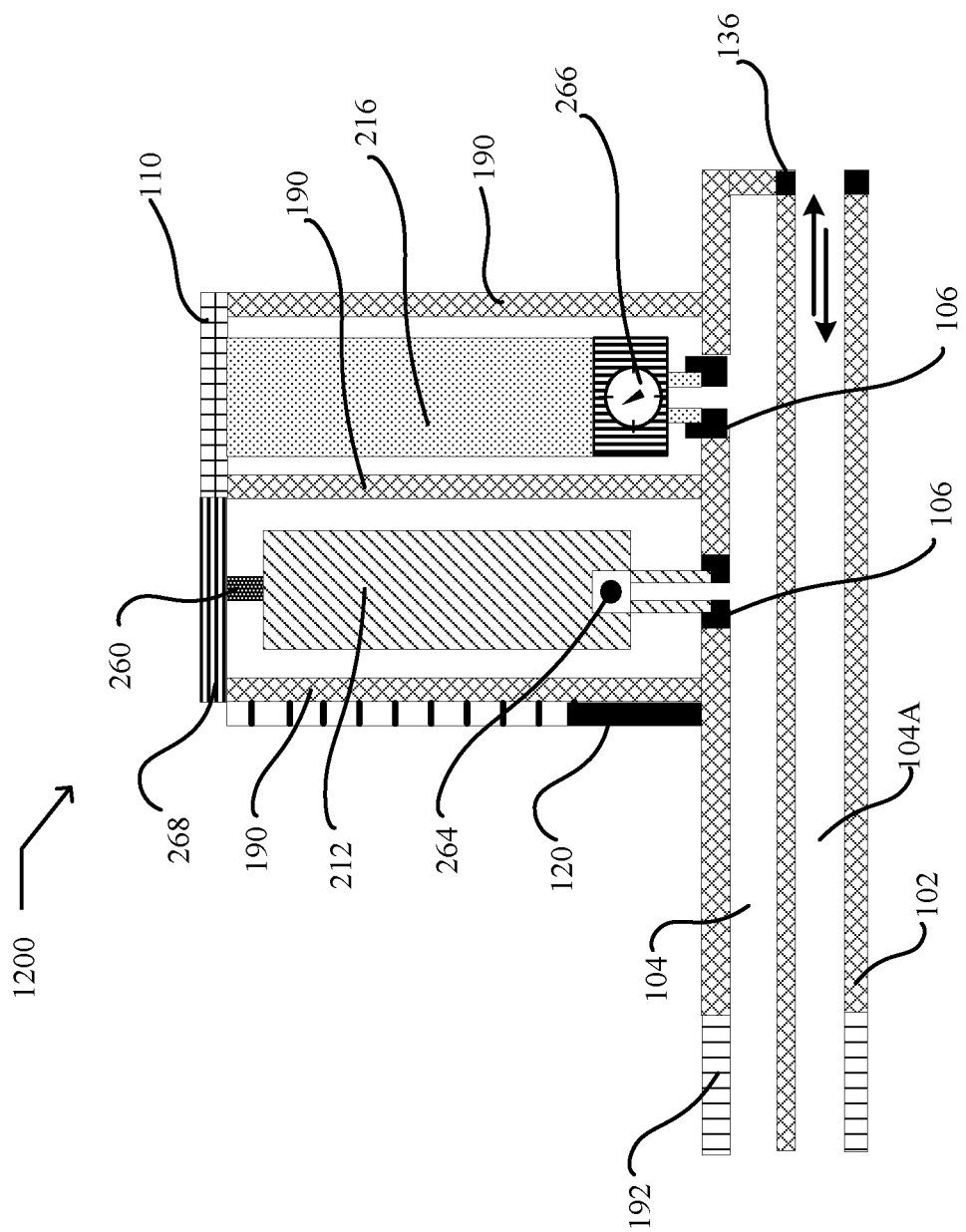
FIG. 12 illustrates a cross-sectional partial side view of an example inhaler 1200 (as viewed along view B-B of FIG. 10A) in which embodiments may be implemented.

FIG. 12 illustrates a partial cross-sectional side view of system 1200 that is configured as an embodiment of an inhaler that includes a housing 102 having flow channel 104 and flow channel 104A disposed therein. Also illustrated are two ports 106 disposed in the housing 102 in fluid communication with the flow channel 104. An inhalant reservoir 212 is illustrated as being operably coupled to one of the ports 106. A propellant reservoir 216 is illustrated as being operably coupled to the other port 106. The inhalant reservoir 212 and the propellant reservoir 216 are illustrated as being held within a reservoir support 190. The inhalant reservoir 212 is configured as an aerosol canister that includes a canister body and a valve stem that extends from the canister body into port 106. The inhalant reservoir 212 includes a controllable valve 264. The controllable valve 264 is illustrated as being closed as indicated by a closed circle. An aerosol canister content release mechanism 268 is illustrated with a pushrod actuator 260 operably coupled with the ethanol-containing inhalant reservoir 212. The aerosol canister content release mechanism 268 is operably coupled with control unit 110. The control unit 110 is configured to direct operation of the aerosol canister content release mechanism 268 to control the pushrod actuator 260 to facilitate at least partial release from the ethanol-containing inhalant reservoir 212. The propellant reservoir 216 is configured as a compressed gas cylinder that is operably coupled to regulator 266. The regulator 266 is operably coupled with control unit 110 that is configured to control operation of the regulator 266 to facilitate at least partial release from the propellant reservoir 216. The control unit 110 is operably coupled with ethanol sensor 136. Flow through flow channel 104A is illustrated by two arrows pointing in opposite directions indicating bidirectional flow through flow channel 104A. The indicator device 120 is illustrated as indicating an assessed concentration of ethanol flowing through the flow channel 104A.

Figure 12A:
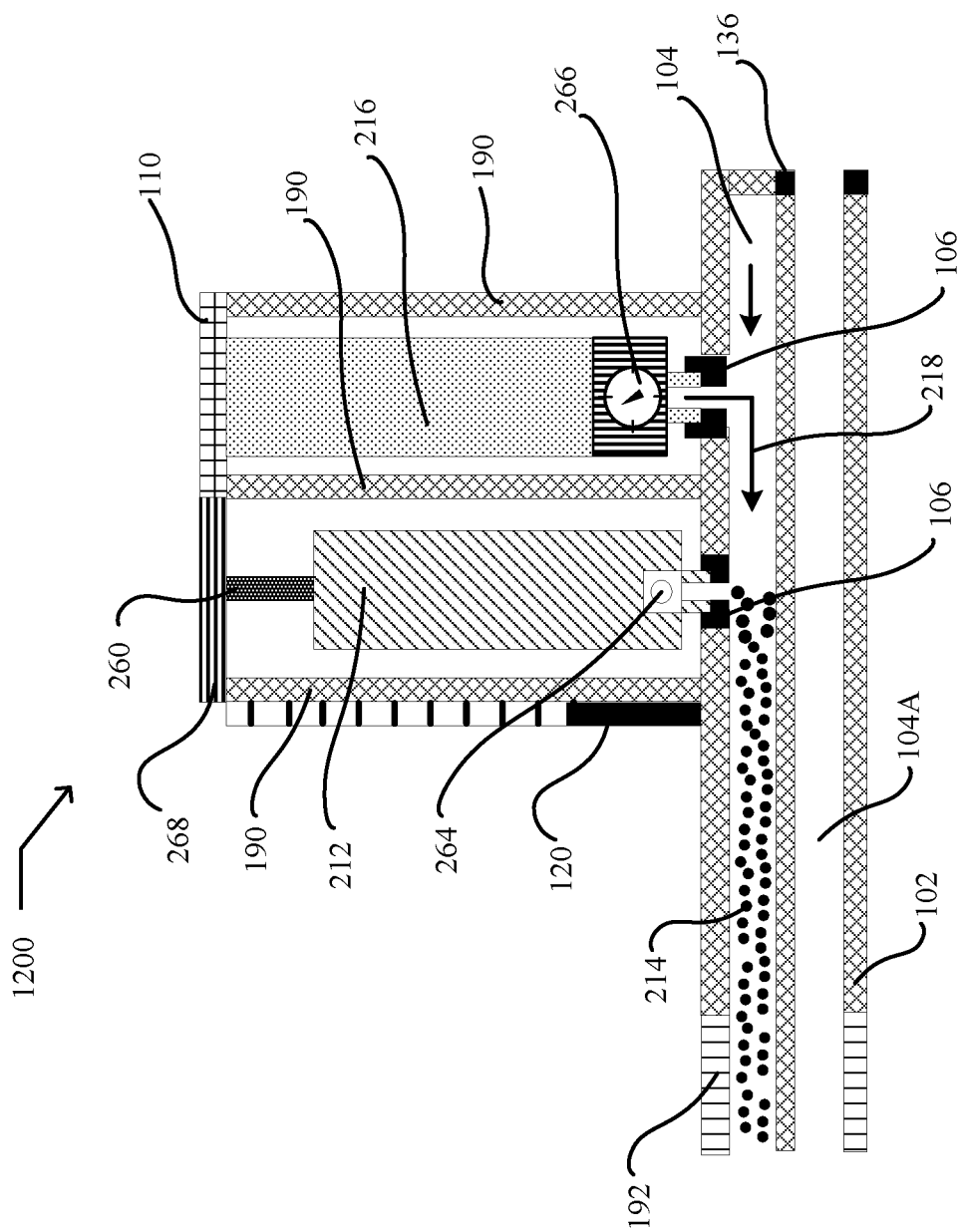
FIG. 12A illustrates a cross-sectional partial side view of an example inhaler 1200 (as viewed along view B-B of FIG. 10A) in which embodiments may be implemented.

FIG. 12A illustrates a partial cross-sectional side view of system 1200 in an activated state to release ethanol-containing inhalant 214 and propellant 218 into flow channel 104. The controllable valve 264 that is operably coupled to the inhalant reservoir 212 is illustrated as being open as indicated by an open circle. The pushrod actuator 260 is illustrated as depressing the aerosol canister to at least partially release the ethanol-containing inhalant 212. The right to left flow of ethanol-containing inhalant 214 and propellant 218 through flow channel 104 toward mouthpiece 192 is indicated by an arrow. Control unit 110 directed the regulator 266 to at least partially release propellant 218 from the propellant reservoir 216.

Figure 13:
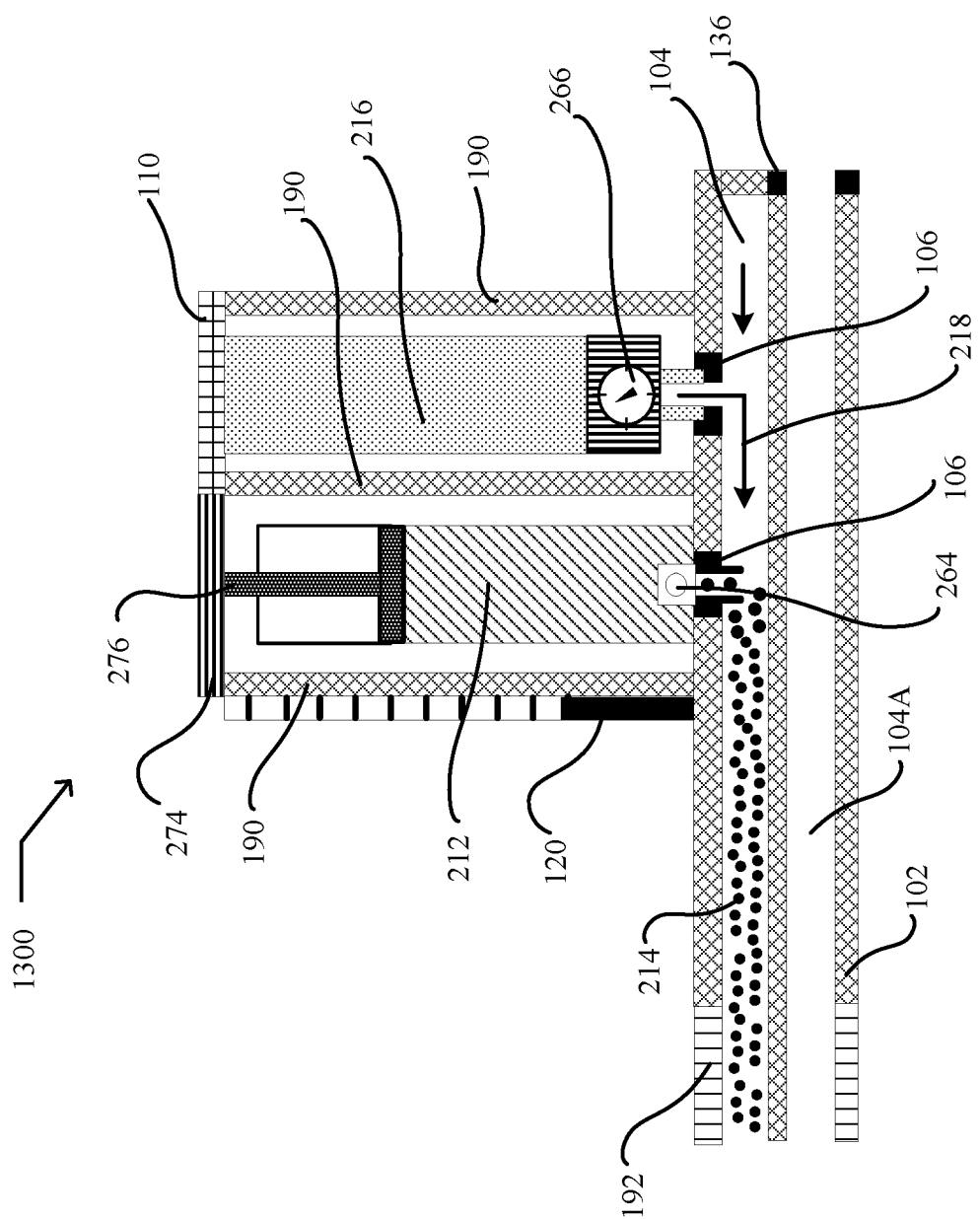
FIG. 13 illustrates a cross-sectional partial side view of an example inhaler 1300 (as viewed along view B-B of FIG. 10A) in which embodiments may be implemented.

FIG. 13 illustrates a partial cross-sectional side view of system 1300 that is configured as an embodiment of an inhaler illustrated as being in an activated state to release ethanol-containing inhalant 214 and propellant 218 into flow channel 104. System 1300 is configured as an inhaler that includes a housing 102 having flow channel 104 and flow channel 104A disposed therein. Two ports 106 are disposed in the housing 102 that are in fluid communication with the flow channel 104. An inhalant reservoir 212 is illustrated as being operably coupled to one of the ports 106. A propellant reservoir 216 is illustrated as being operably coupled to the other port 106. The inhalant reservoir 212 and the propellant reservoir 216 are illustrated as being held within a reservoir support 190. The inhalant reservoir 212 is configured as a barrel that includes a plunger 276 that is operably coupled to a plunger actuator 274 that is configured to depress the plunger 276 to facilitate release of ethanol-containing inhalant 214 from the inhalant reservoir 212. The plunger actuator 274 is operably coupled to control unit 110 that is configured to control operation of the plunger actuator 274. The plunger 276 is illustrated as being depressed into the barrel of the inhalant reservoir 212 to facilitate at least partial release of ethanol-containing inhalant 214 into flow channel 104. The inhalant reservoir 212 includes a controllable valve 264. The controllable valve 264 is illustrated as being open as indicated by an open circle. The controllable valve 264 is operably coupled to control unit 110 that is configured to control operation of the controllable valve 264. The propellant reservoir 216 is configured as a compressed gas cylinder that is operably coupled to a regulator 266. The regulator 266 is operably coupled with a control unit 110 that is configured to control operation of the regulator 266 to facilitate at least partial release from the propellant reservoir 216. The control unit 110 is operably coupled with ethanol sensor 136. Right to left flow through flow channel 104 is indicated by the arrow.

Figure 14:
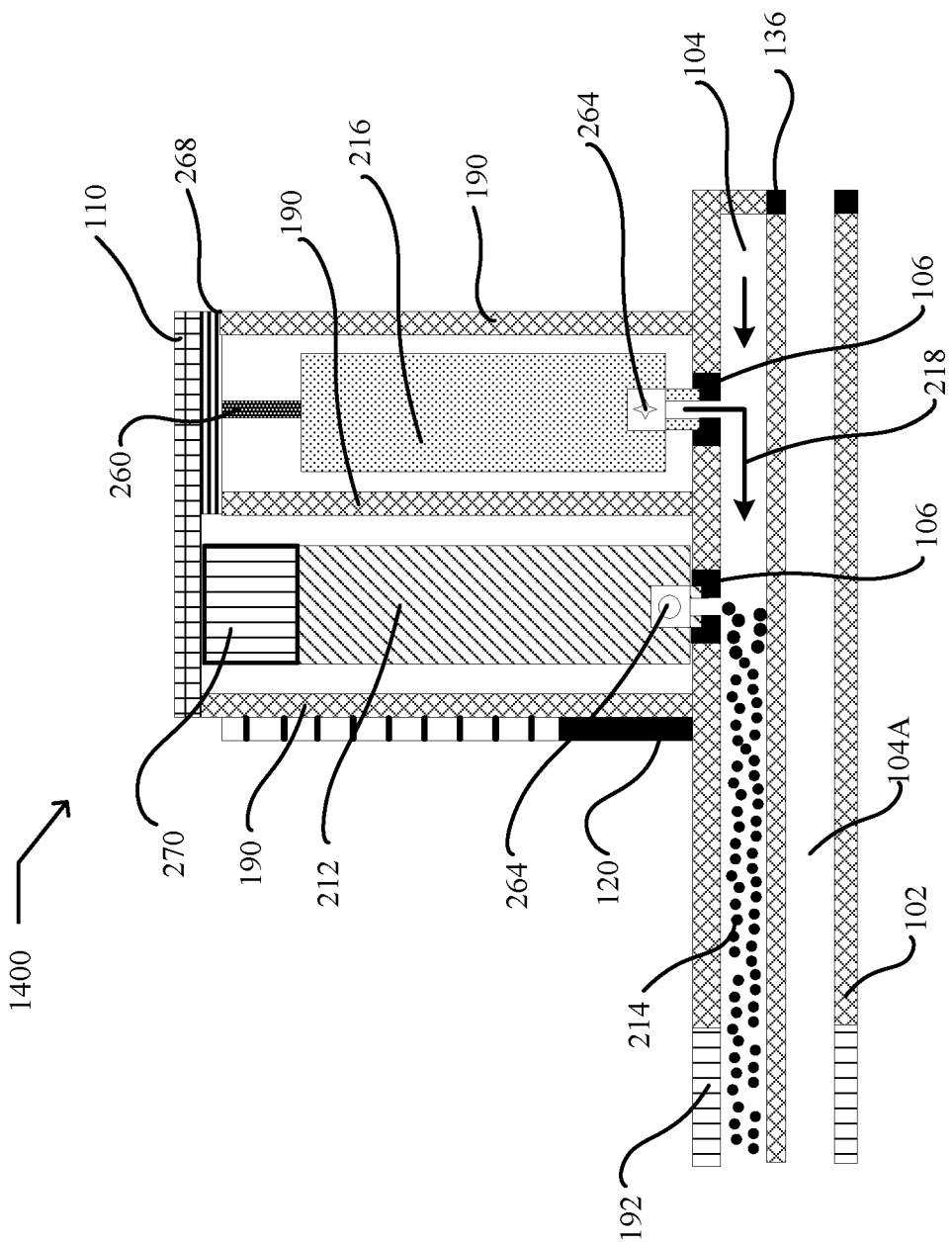
FIG. 14 illustrates a cross-sectional partial side view of an example inhaler 1400 (as viewed along view B-B of FIG. 10A) in which embodiments may be implemented.

FIG. 14 illustrates a partial cross-sectional side view of system 1400 that is configured as an embodiment of an inhaler illustrated as being in an activated state to release ethanol-containing inhalant 214 and propellant 218 into flow channel 104. System 1400 includes a housing 102 having flow channel 104 and flow channel 104A disposed therein. The housing 102 is operably coupled to mouthpiece 192. Also illustrated are ports 106 disposed in the housing 102 that are in fluid communication with flow channel 104. An inhalant reservoir 212 and a propellant reservoir 216 are each operably coupled to a port 106. The inhalant reservoir 212 and the propellant reservoir 216 are illustrated as being held within a reservoir support 190. The ethanol-containing inhalant reservoir 212 is operably coupled to heater 270. The heater 270 is operably coupled with control unit 110. The control unit 110 is configured to direct operation of the heater 270 and the controllable valve 264 to facilitate at least partial release from the ethanol-containing inhalant reservoir 212. The ethanol-containing inhalant reservoir 212 includes a controllable valve 264 that is illustrated as being open as indicated by an open circle. The propellant reservoir 216 is configured as an aerosol canister that includes a canister body and a valve stem that extends from the canister body into port 106. The propellant reservoir 216 includes a controllable valve 264. The controllable valve 264 is illustrated as being open as indicated by an open star. An aerosol canister content release mechanism 268 is illustrated with a pushrod actuator 260 operably coupled with the propellant reservoir 216. The aerosol canister content release mechanism 268 is operably coupled with a control unit 110. The control unit 110 is configured to direct operation of the aerosol canister content release mechanism 268 to control the pushrod actuator 260 to facilitate at least partial release from the propellant reservoir 216. The pushrod actuator 260 is illustrated as depressing the aerosol canister to at least partially release the propellant 218 into the flow channel 104. An ethanol sensor 136 is operably coupled to flow channel 104A and configured to detect the concentration of ethanol flowing through flow channel 104A. Control unit 110 is operably coupled with ethanol sensor 136. Accordingly, in some embodiments, ethanol sensor 136 may be configured to detect a concentration of ethanol flowing through flow channel 104A during use of the inhaler by a subject. In some embodiments, such information may be transmitted to control unit 110 that may use the information to calculate a quantity of ethanol-containing inhalant 214 to be released to reach a selected blood alcohol concentration in a subject using the inhaler. The control unit 110 may then control operation of the heater 270 and the controllable valve 264 to release ethanol-containing inhalant 214 to reach the selected blood alcohol concentration. Right to left flow through flow channel 104 is indicated by an arrow. An indicator device 120 is illustrated as showing the concentration of ethanol flowing through flow channel 104A.

Figure 15:
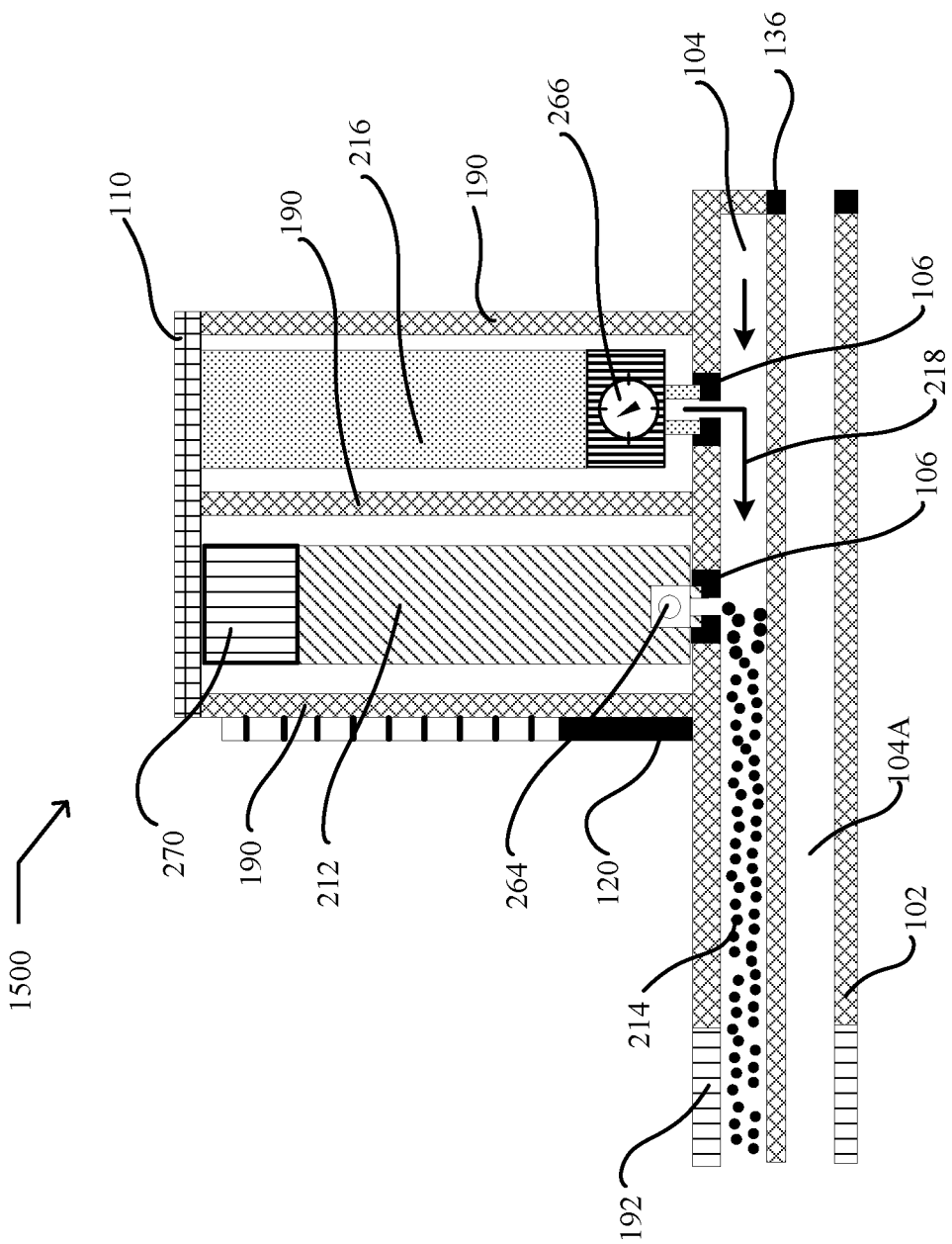
FIG. 15 illustrates a cross-sectional partial side view of an example inhaler 1500 (as viewed along view B-B of FIG. 10A) in which embodiments may be implemented.

FIG. 15 illustrates a partial cross-sectional side view of system 1500 that is configured as an embodiment of an inhaler illustrated as being in an activated state to release ethanol-containing inhalant 214 and propellant 218 into flow channel 104. System 1500 includes a housing 102 having flow channel 104 and flow channel 104A disposed therein. The housing 102 is operably coupled to mouthpiece 192. Also illustrated are ports 106 disposed in the housing 102 that are in fluid communication with flow channel 104. An inhalant reservoir 212 and a propellant reservoir 216 are each operably coupled to a port 106. The inhalant reservoir 212 and the propellant reservoir 216 are illustrated as being held within a reservoir support 190. The inhalant reservoir 212 is operably coupled to heater 270. The heater 270 is operably coupled with control unit 110. The control unit 110 is configured to direct operation of the heater 270 and the controllable valve 264 to facilitate at least partial release from the inhalant reservoir 212. The inhalant reservoir 212 includes a controllable valve 264 that is illustrated as being open as indicated by an open circle. The propellant reservoir 216 is configured as a compressed gas cylinder that is operably coupled to a regulator 266. The regulator 266 is operably coupled with a control unit 110 that is configured to control operation of the regulator 266 to facilitate at least partial release of propellant 218 from the propellant reservoir 216. An ethanol sensor 136 is operably coupled to flow channel 104A and configured to detect the concentration of ethanol flowing through flow channel 104A. Control unit 110 is operably coupled with ethanol sensor 136. Accordingly, in some embodiments, ethanol sensor 136 may be configured to detect a concentration of ethanol flowing through flow channel 104A during use of the inhaler by a subject. In some embodiments, such information may be transmitted to control unit 110 that may use the information to calculate a quantity of ethanol-containing inhalant 214 to be released to reach a selected blood alcohol concentration in the subject. The control unit 110 may then control operation of the heater 270 and the controllable valve 264 to release ethanol-containing inhalant 214 to reach the selected blood alcohol concentration. Right to left flow through flow channel 104 is indicated by an arrow. An indicator device 120 is illustrated as showing the concentration of ethanol flowing through flow channel 104A.

Figure 16:
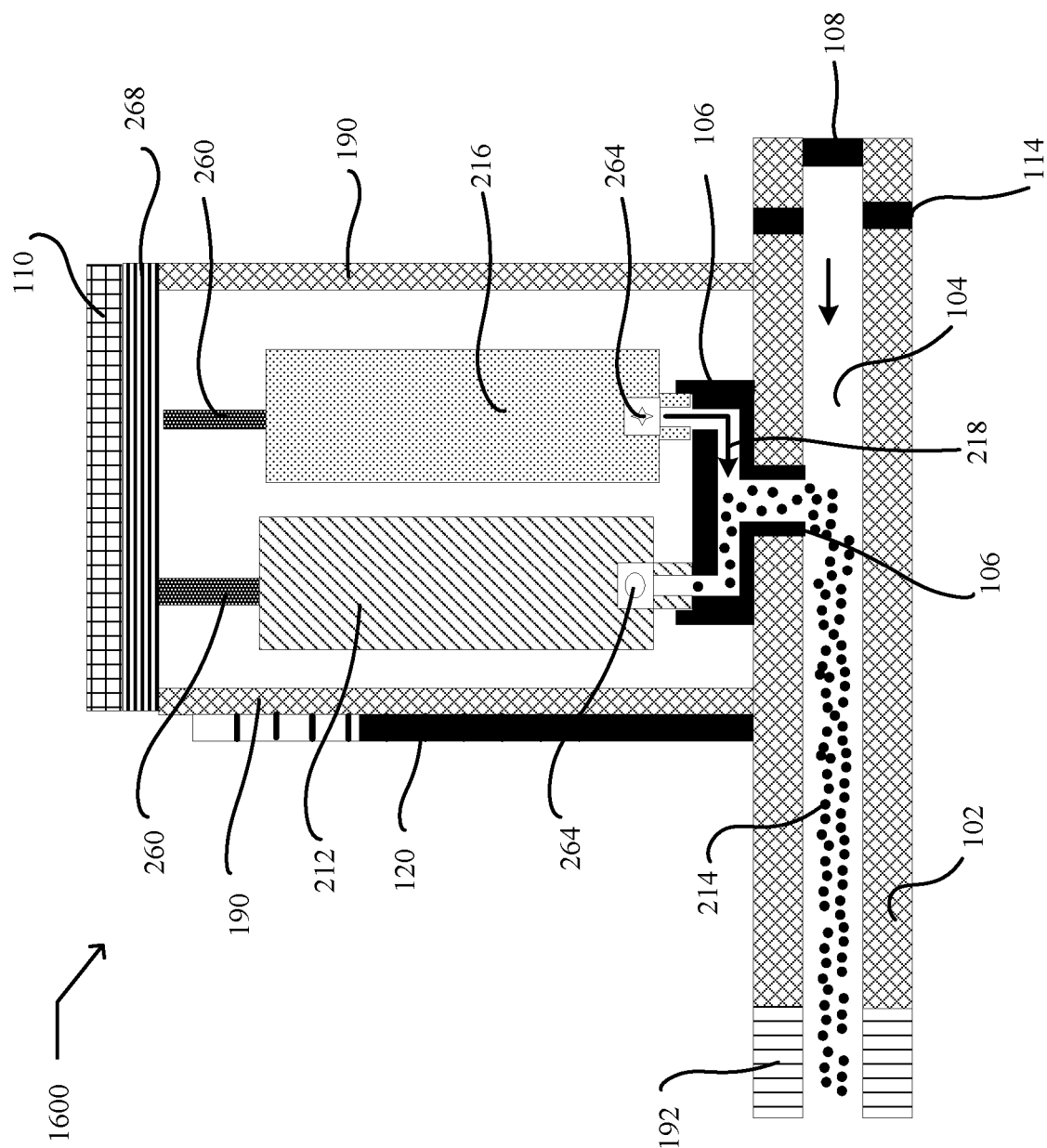
FIG. 16 illustrates a cross-sectional partial side view of an example inhaler 1600 (as viewed along view B-B of FIG. 10A) in which embodiments may be implemented.

FIG. 16 illustrates a partial cross-sectional side view of system 1600. System 1600 is shown as an embodiment of an inhaler in an activated state to release ethanol-containing inhalant 214 and propellant 218 into flow channel 104. System 1600 includes a housing 102 having flow channel 104 disposed therein. Also illustrated is port 106 disposed in the housing 102 in fluid communication with the flow channel 104. An inhalant reservoir 212 is illustrated as being operably coupled to port 106. A propellant reservoir 216 is illustrated as being operably coupled to port 106. The inhalant reservoir 212 and the propellant reservoir 216 are illustrated as being held within reservoir support 190. The inhalant reservoir 212 and the propellant reservoir 216 are configured as aerosol canisters that include a canister body and a valve stem that each extend from the canister body into port 106. The inhalant reservoir 212 and the propellant reservoir 216 each include a controllable valve 264. The controllable valves 264 are illustrated as being open as indicated by an open circle and an open star. Right to left flow through flow channel 104 is indicated by an arrow. A flow valve 108 is operably coupled to flow channel 104 and configured to control flow through flow channel 104. The flow valve 108 is illustrated in the closed position to direct flow toward mouthpiece 192. An aerosol canister content release mechanism 268 is illustrated with a pushrod actuator 260 operably coupled with each of the inhalant reservoir 212 and the propellant reservoir 216. Pushrod actuators 260 are illustrated as depressing each of the aerosol canisters to at least partially release the ethanol-containing inhalant 212 and the propellant 216. The aerosol canister content release mechanism 268 is operably coupled with a control unit 110. The control unit 110 is configured to direct operation of the aerosol canister content release mechanism 268 to control the pushrod actuators 260 to facilitate at least partial release from the inhalant reservoir 212 and the agent reservoir 220. The control unit 110 is operably coupled with an ethanol sensor 136. Accordingly, in some embodiments, the control unit 110 may be configured to facilitate at least partial release from one or both of the inhalant reservoir 212 and the propellant reservoir 216 in response to information received from ethanol sensor 136. In some embodiments, an ethanol sensor 136 may be configured to detect a concentration of ethanol in exhalant that flows through the flow channel 104 during use of the inhaler by a subject. Accordingly, in some embodiments, such concentration information may be transmitted to the control unit 110 that may use the information to calculate a quantity of ethanol-containing inhalant 214 to be released from an inhalant reservoir 212 to reach a selected blood alcohol concentration in a subject using the inhaler. The control unit 110 may then control operation of the aerosol canister content release mechanism 268 to facilitate release of ethanol-containing inhalant 214 to reach the selected blood alcohol concentration. An indicator device 120 is illustrated as showing a concentration of ethanol flowing through flow channel 104.

Figure 17:
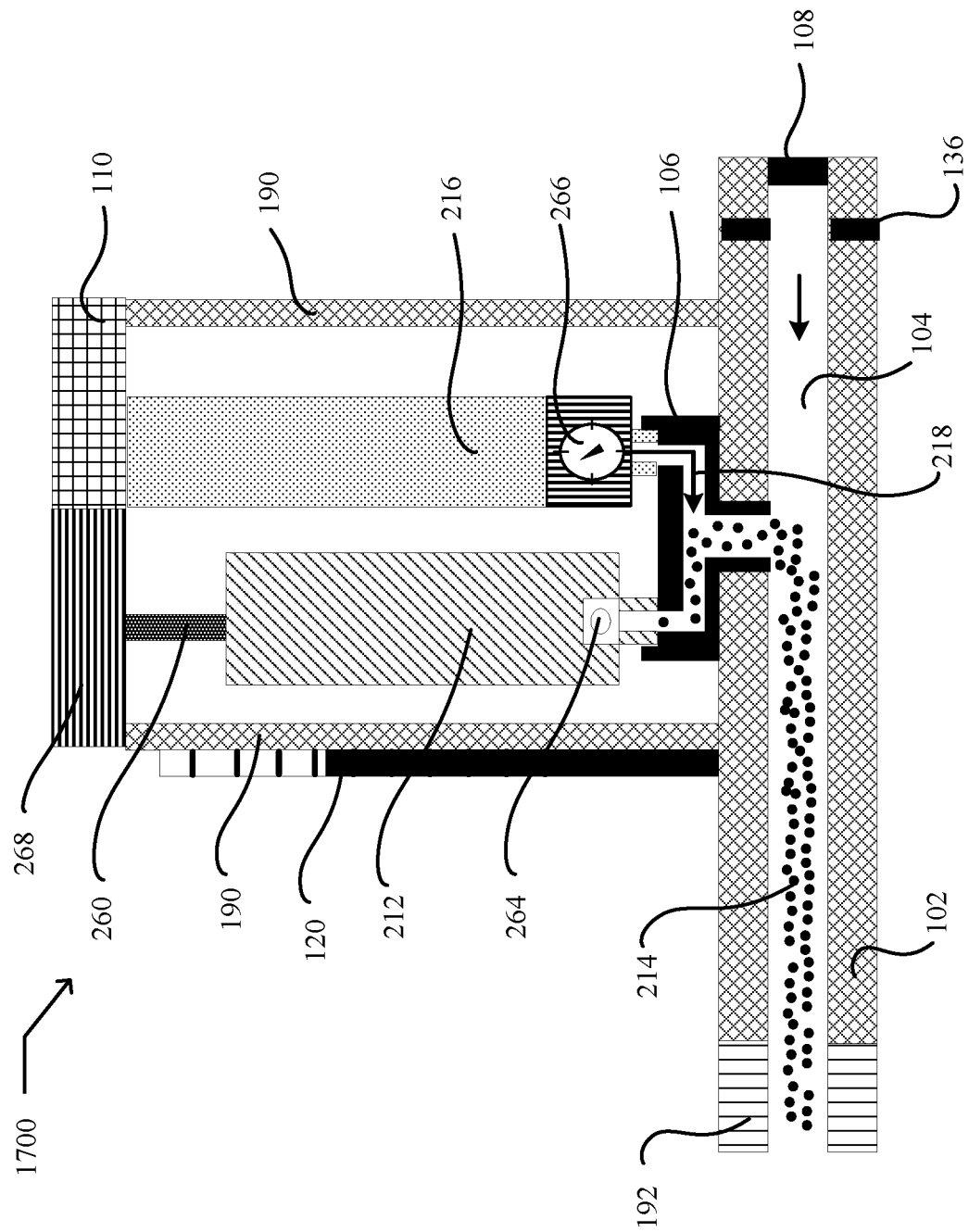
FIG. 17 illustrates a cross-sectional partial side view of an example inhaler 1700 (as viewed along view B-B of FIG. 10A) in which embodiments may be implemented.

FIG. 17 illustrates a partial cross-sectional side view of system 1700. System 1600 is shown as an embodiment of an inhaler in an activated state to release ethanol-containing inhalant 214 and propellant 218 into flow channel 104. System 1700 is an embodiment of an inhaler that includes a housing 102 having flow channel 104 disposed therein. Also illustrated is port 106 disposed in the housing 102 in fluid communication with the flow channel 104. An inhalant reservoir 212 is illustrated as being operably coupled to port 106. A propellant reservoir 216 is illustrated as being operably coupled to port 106. The inhalant reservoir 212 and the propellant reservoir 216 are illustrated as being held within a reservoir support 190. The inhalant reservoir 212 is configured as an aerosol canister that includes a canister body and a valve stem that extends from the canister body into port 106. The inhalant reservoir 212 includes a controllable valve 264. The controllable valve 264 is illustrated as being open as indicated by an open circle. An aerosol canister content release mechanism 268 is illustrated with a pushrod actuator 260 operably coupled with the inhalant reservoir 212. Pushrod actuator 260 is illustrated as depressing the aerosol canister to at least partially release the ethanol-containing inhalant 212. The aerosol canister content release mechanism 268 is operably coupled with a control unit 110. The control unit 110 is configured to direct operation of the aerosol canister content release mechanism 268 to control the pushrod actuator 260 to facilitate at least partial release from the inhalant reservoir 212. The propellant reservoir 216 is configured as a compressed gas cylinder that is operably coupled to a regulator 266. The regulator 266 is operably coupled with a control unit 110 that is configured to control operation of the regulator 266 to facilitate at least partial release from the propellant reservoir 216. The control unit 110 is operably coupled with ethanol sensor 136. A flow valve 108 is operably coupled to flow channel 104 and configured to control flow through flow channel 104. Flow valve 108 is illustrated in the closed position to direct flow toward mouthpiece 192. Right to left flow through flow channel 104 is indicated by the arrow. The indicator device 120 is illustrated as indicating an assessed concentration of ethanol flowing through the flow channel 104.

Figure 18:
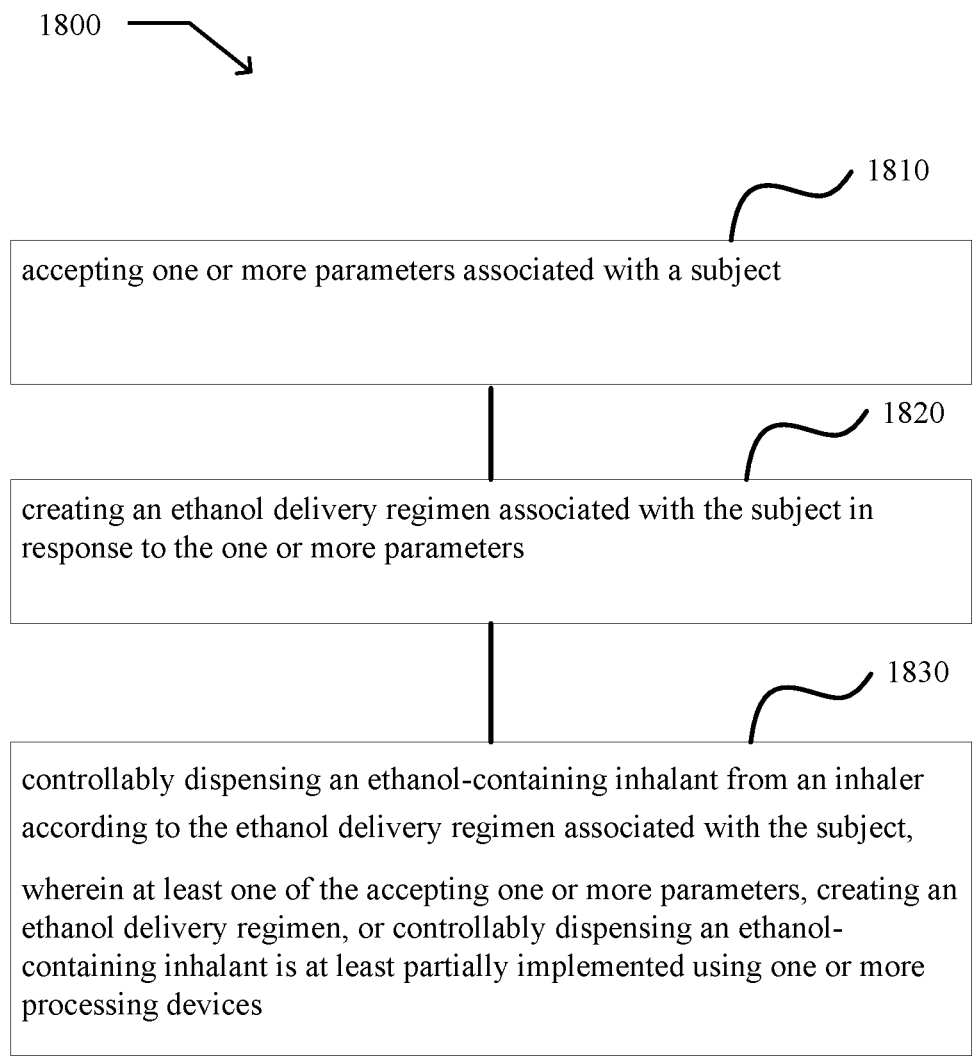
FIG. 18 illustrates an example operational flow 1800 in which embodiments may be implemented.

FIG. 18 illustrates operational flow 1800 that includes operation 1810 that includes accepting one or more parameters associated with a subject, operation 1820 that includes creating an ethanol delivery regimen associated with the subject in response to the one or more parameters, and operation 1830 that includes controllably dispensing an ethanol-containing inhalant from an inhaler according to the ethanol delivery regimen associated with the subject, wherein at least one of the accepting one or more parameters, creating an ethanol delivery regimen, or controllably dispensing an ethanol-containing inhalant is at least partially implemented using one or more processing devices.

In FIG. 18 and in the following description that includes various examples of operations used during performance of the method, discussion and explanation may be provided with respect to any one or combination of the above-described examples, and/or with respect to other examples and contexts. However, it should be understood that the operations may be executed in a number of other environments and contexts, and/or modified versions of the figures.

Also, although the various operations are presented in the sequence(s) illustrated, it should be understood that the various operations may be performed in other orders than those which are illustrated, or may be performed concurrently.

Operation 1810 includes accepting one or more parameters associated with a subject. In some embodiments, system 100 may be used to accept one or more parameters associated with a subject. For example, in some embodiments, a user interface 112 may be used to accept one or more parameters associated with a subject. In some embodiments, a sensor 116 may be used to accept one or more parameters associated with a subject. Numerous types of parameters associated with a subject may be accepted. Examples of such parameters include, but are not limited to, physical parameters (e.g., age, height, weight, gender), physiological parameters (e.g., metabolism), psychological parameters (e.g., depression, mood disorders, hyperactivity), identity parameters (e.g., name, address), age parameters, occupancy parameters (e.g., proximity of other subjects in the vicinity of a subject), motion parameters (e.g., transport in an automobile), ethanol parameters (e.g., daily consumption of ethanol, selected blood alcohol concentration), substance parameters (e.g., use of prescription drugs, use of illegal drugs, use of over the counter drugs), timing parameters (e.g., time of day, time when blood alcohol concentration is to be 0.0), location parameters (e.g., global positioning coordinates, permissible location, impermissible location), legal parameters (e.g., court orders, restraining orders), activity parameters (e.g., driving, skiing, walking, running), consumption parameters (e.g., intended consumption of ethanol at one or more times, one or more quantities of ethanol consumed), flavoring parameters (e.g., subject selected flavoring agent), and the like. In some embodiments, one or more parameters may be accepted from a remote device (e.g., remote sensor 116, bracelet, badge, cellular telephone, transdermal ethanol sensor). In some embodiments, one or more parameters may be retrieved from a database.

Operation 1820 includes creating an ethanol delivery regimen associated with the subject in response to the one or more parameters. In some embodiments, system 100 may be used to create an ethanol delivery regimen associated with the subject in response to the one or more parameters. For example, in some embodiments, a control unit 110 may be used to create an ethanol delivery regimen associated with a subject in response to one or more parameters associated with the subject. Numerous types of ethanol delivery regimens may be obtained or created. For example, in some embodiments, a control unit 110 may create an ethanol delivery regimen to dispense an ethanol-containing inhalant 214. In some embodiments, a control unit 110 may prevent an ethanol-containing inhalant 214 from being dispensed in response to one or more parameters. In some embodiments, a control unit 110 may determine one or more quantities of an ethanol-containing inhalant to dispense. In some embodiments, a control unit 110 may determine one or more quantities of an ethanol-containing inhalant to dispense at one or more times. In some embodiments, a control unit 110 may determine one or more rates at which to dispense an ethanol-containing inhalant. In some embodiments, a control unit 110 may determine one or more times to dispense an ethanol-containing inhalant. In some embodiments, a control unit 110 may determine one or more times not to dispense an ethanol-containing inhalant. In some embodiments, a control unit 110 may determine one or more particle sizes of an ethanol-containing inhalant to dispense. In some embodiments, a control unit 110 may determine one or more ethanol-containing inhalant formulations to dispense. In some embodiments, a control unit 110 may select a preexisting ethanol-containing inhalant delivery regimen. In some embodiments, a control unit 110 may select a preexisting ethanol-containing inhalant delivery regimen from a list, a catalog, a database, a table, or substantially any combination thereof.

Operation 1830 includes controllably dispensing an ethanol-containing inhalant from an inhaler according to the ethanol delivery regimen associated with the subject, wherein at least one of the accepting one or more parameters, creating an ethanol delivery regimen, or controllably dispensing an ethanol-containing inhalant is at least partially implemented using one or more processing devices. In some embodiments, system 100 may be used to controllably dispense an ethanol-containing inhalant from an inhaler according to the ethanol delivery regimen associated with the subject, wherein at least one of the accepting one or more parameters, creating an ethanol delivery regimen, or controllably dispensing an ethanol-containing inhalant is at least partially implemented using one or more processing devices. For example, in some embodiments, a control unit 110 may be configured to control the operation of one or more actuators 122 to facilitate at least partial release of an ethanol-containing inhalant 214 from one or more inhalant reservoirs 212. In some embodiments, a control unit 110 may be configured to control the operation of one or more actuators 122 to facilitate at least partial release of an ethanol-containing inhalant 214 from one or more inhalant reservoirs 212 at one or more permissible times. In some embodiments, a control unit 110 may be configured to control the operation of one or more actuators 122 to prevent release of an ethanol-containing inhalant 214 from one or more inhalant reservoirs 212 at one or more impermissible times. In some embodiments, a control unit 110 may be configured to control the operation of one or more actuators 122 to facilitate at least partial release of an ethanol-containing inhalant 214 from one or more inhalant reservoirs 212 at one or more permissible locations. In some embodiments, a control unit 110 may be configured to control the operation of one or more actuators 122 to prevent release of an ethanol-containing inhalant 214 from one or more inhalant reservoirs 212 at one or more impermissible locations. In some embodiments, a control unit 110 may be configured to control the operation of one or more actuators 122 to facilitate at least partial release of an ethanol-containing inhalant 214 from one or more inhalant reservoirs 212 to one or more approved subjects. In some embodiments, a control unit 110 may be configured to control the operation of one or more actuators 122 to prevent release of an ethanol-containing inhalant 214 from one or more inhalant reservoirs 212 at one or more disapproved subjects. In some embodiments, a control unit 110 may be configured to control the operation of one or more actuators 122 to release one or more determined quantities of an ethanol-containing inhalant 214 from one or more inhalant reservoirs 212. In some embodiments, a control unit 110 may be configured to control the operation of one or more actuators 122 to release one or more determined quantities of an ethanol-containing inhalant 214 from one or more inhalant reservoirs 212 at one or more times. In some embodiments, a control unit 110 may be configured to select one or more inhalant reservoirs 212 that contain an ethanol-containing inhalant 214 having selected particle sizes and then control the operation of one or more actuators 122 to release the ethanol-containing inhalant 214 from one or more inhalant reservoirs 212. In some embodiments, a control unit 110 may be configured to select one or more inhalant reservoirs 212 that contain a selected ethanol-containing inhalant 214 formulation and then control the operation of one or more actuators 122 to release the ethanol-containing inhalant 21 from one or more inhalant reservoirs 212.

In some embodiments, operation 1810 includes accepting one or more physical parameters (not shown). In some embodiments, system 100 may be used to accept one or more physical parameters. For example, in some embodiments, a user interface 112 may be used to accept one or more physical parameters associated with a subject. In some embodiments, a control unit 110 may be used to accept one or more physical parameters associated with a subject. Numerous types of physical parameters may be accepted. Examples of such physical parameters include, but are not limited to, height, weight, gender, and the like.

In some embodiments, operation 1810 includes accepting one or more location parameters (not shown). In some embodiments, system 100 may be used to accept one or more location parameters. For example, in some embodiments, a user interface 112 may be used to accept one or more location parameters. In some embodiments, a control unit 110 may be used to accept one or more location parameters. Numerous types of location parameters may be accepted. Examples of such location parameters include, but are not limited to, global positioning coordinates, location parameters associated with a mode of transportation (e.g., presence in an automobile, airplane, or the like), location parameters associated with being present in a building (e.g., police station, school, church, home, or the like), and the like.

In some embodiments, operation 1810 includes accepting one or more time and one or more location parameters (not shown). In some embodiments, system 100 may be used to accept one or more time and one or more location parameters. For example, in some embodiments, a user interface 112 may be used to accept one or more time and one or more location parameters. In some embodiments, a control unit 110 may be used to accept one or more time and one or more location parameters. Numerous types of location parameters may be accepted. Examples of such location parameters include, but are not limited to, global positioning coordinates, location parameters associated with a mode of transportation (e.g., presence in an automobile, airplane, or the like), location parameters associated with being present in a building (e.g., police station, school, church, home, or the like), and the like. Numerous types of time parameters may be accepted. Examples of such time parameters include, but are not limited to, the time of day, time following the consumption of ethanol, time following the intake of a pharmaceutical agent, an amount of time preceding an activity (e.g., time until a subject expects to drive an automobile), and the like.

In some embodiments, operation 1810 includes receiving information associated with the one or more parameters from an electronic device associated with the subject (see device 125 of FIG. 1). In some embodiments, system 100 may be used to receive information associated with the one or more parameters from an electronic device associated with the subject. For example, in some embodiments, a user interface 112 may be used to receive information associated with the one or more parameters from an electronic device associated with the subject. In some embodiments, a control unit 110 may be used to receive information associated with the one or more parameters from an electronic device associated with the subject. Information may be received from numerous types of electronic devices associated with a subject. Examples of such devices include, but are not limited to, heart monitors, blood pressure monitors, transdermal ethanol sensors 136, breathalyzers, and the like. Such devices may be configured in numerous ways. Examples of such configurations include, but are not limited to, badges, bracelets, rings, keychains, and the like.

In some embodiments, operation 1810 includes receiving information associated with the one or more parameters from at least one database (not shown). In some embodiments, system 100 may be used to receive information associated with the one or more parameters from at least one database. For example, in some embodiments, a user interface 112 may be used to receive information associated with the one or more parameters from at least one database. In some embodiments, a control unit 110 may be used to receive information associated with the one or more parameters from at least one database.

In some embodiments, operation 1820 includes creating an ethanol delivery regimen to dispense the ethanol-containing inhalant 214 (not shown). In some embodiments, system 100 may be used to create an ethanol delivery regimen to dispense the ethanol-containing inhalant 214. For example, in some embodiments, a control unit 110 may be used to create an ethanol delivery regimen to dispense the ethanol-containing inhalant 214. Numerous types of ethanol delivery regimens may be created to dispense the ethanol-containing inhalant 214. For example, in some embodiments, an ethanol delivery regimen may be created to deliver an ethanol-containing inhalant 214 at one or more times. In some embodiments, an ethanol delivery regimen may be created to deliver an ethanol-containing inhalant 214 at one or more locations. In some embodiments, an ethanol delivery regimen may be created to deliver an ethanol-containing inhalant 214 at one or more times and one or more locations. In some embodiments, an ethanol delivery regimen may be created to deliver a determined quantity of an ethanol-containing inhalant 214 to a subject. In some embodiments, an ethanol delivery regimen may be created to deliver an ethanol-containing inhalant 214 to a subject until a predetermined blood alcohol concentration is reached for the subject.

In some embodiments, operation 1820 includes determining one or more quantities of the ethanol-containing inhalant 214 to dispense at one or more times (not shown). In some embodiments, system 100 may be used to determine one or more quantities of ethanol-containing inhalant 214 to dispense at one or more times. For example, in some embodiments, a control unit 110 may be used to determine one or more quantities of ethanol-containing inhalant 214 to dispense at one or more times. The quantity of ethanol-containing inhalant 214 to dispense may be determined in numerous ways. In some embodiments, one or more parameters associated with a subject may be used to determine one or more quantities of ethanol-containing inhalant 214 to dispense at one or more times. For example, in some embodiments, a control unit 110 may be configured to determine one or more quantities of ethanol-containing inhalant 214 to dispense based on the weight and gender of a subject. For example, in some embodiments, a control unit 110 may accept weight and gender parameters associated with a subject, accept a selected blood alcohol concentration that the subject would like to achieve, and then calculate a quantity of an ethanol-containing inhalant 214 to dispense to the subject to achieve the desired blood alcohol concentration based on a correlation of weight, gender, and ethanol intake. In some embodiments, a control unit 110 may determine one or more quantities of ethanol-containing inhalant 214 to dispense based on an assessed value associated with the blood alcohol concentration of a subject in combination with the weight and gender of the subject. For example, in some embodiments, a control unit 110 may accept information related to the current blood alcohol concentration associated with a subject, accept weight and gender information associated with the subject, accept information associate with a selected blood alcohol concentration that the subject would like to achieve, and then use the information in combination with a correlation between ethanol intake and weight and gender to calculate an additional quantity of an ethanol-containing inhalant 214 to deliver to the subject.

In some embodiments, operation 1820 includes determining one or more particle sizes to deliver the ethanol-containing inhalant 214 (not shown). In some embodiments, system 100 may be used to determine one or more particle sizes to deliver the ethanol-containing inhalant 214. For example, in some embodiments, a control unit 110 may be used to determine one or more particle sizes to deliver the ethanol-containing inhalant 214. In some embodiments, a control unit 110 may select an inhalant reservoir 212 that contains ethanol containing particles having a diameter less than about one micrometer to deliver the ethanol containing particles to peripheral airways or alveoli of a subject. In some embodiments, a control unit 110 may select an inhalant reservoir 212 that contains ethanol containing particles having a diameter between about one micrometer and about five micrometers to deliver the ethanol containing particles to the large and conducting airways of a subject. In some embodiments, a control unit 110 may select an inhalant reservoir 212 that contains ethanol containing particles having a diameter greater than about five micrometers to deliver the ethanol containing particles to the oropharynx of a subject.

In some embodiments, operation 1820 includes selecting one or more ethanol-containing inhalant 214 formulations (not shown). In some embodiments, system 100 may be used to select one or more ethanol-containing inhalant 214 formulations. For example, in some embodiments, a control unit 110 may be used to select one or more ethanol-containing inhalant 214 formulations. In some embodiments, a control unit 110 may select an inhalant reservoir 212 that contains a desired ethanol-containing inhalant 214 formulation. Numerous types of formulations may be selected. For example, in some embodiments, a formulation having a substantially immediate release profile may be selected. In some embodiments, a formulation having a substantially delayed release profile may be selected. In some embodiments, a formulation having an intermediate release profile may be selected. In some embodiments, one or more formulations may be selected that have different release profiles. For example, in some embodiments, a formulation having a substantially immediate release profile may be selected and another formulation having a substantially delayed release profile may be selected. Accordingly, in some embodiments, a control unit 110 may select numerous types of ethanol-containing inhalant 214 formulations.

In some embodiments, operation 1820 includes selecting at least one preexisting ethanol-containing inhalant delivery regimen (not shown). In some embodiments, system 100 may be used to select at least one preexisting ethanol-containing inhalant delivery regimen. For example, in some embodiments, a control unit 110 may be used to select at least one preexisting ethanol-containing inhalant delivery regimen. In some embodiments, ethanol-containing inhalant delivery regimens may be prepared and saved in a database or other storage medium. Accordingly, in some embodiments, a control unit 110 may use one or more parameters associated with a subject to select a preexisting ethanol-containing inhalant delivery regimen. Such preexisting ethanol-containing inhalant delivery regimens may be prepared by correlating parameters associated with subjects with blood alcohol concentrations to be associated with the subjects. For example, in some embodiments, a preexisting ethanol-containing inhalant delivery regimen may be prepared for a 180 pound male who would like to achieve a blood alcohol concentration of 0.05 by accessing existing tables that correlate gender, weight, and ethanol intake to blood alcohol concentration and use the information to determine a quantity of an ethanol-containing inhalant 214 to be delivered to the subject and save the information in a storage medium. Accordingly, such information may be accessed by a control unit 110 that can select the preexisting ethanol-containing inhalant delivery regimen from memory.

In some embodiments, operation 1830 includes preventing dispensation of the ethanol-containing inhalant 214 at one or more impermissible times (not shown). In some embodiments, system 100 may be used to prevent dispensation of an ethanol-containing inhalant 214 at one or more impermissible times. In some embodiments, control unit 110 may be configured to prevent dispensation of an ethanol-containing inhalant 214 at one or more impermissible times. For example, in some embodiments, control unit 110 may be configured to prevent dispensation of an ethanol-containing inhalant 214 between the hours of 12 AM and 6 PM. In some embodiments, control unit 110 may be configured to prevent dispensation of an ethanol-containing inhalant 214 between the hours of 8 AM and 6 PM. In some embodiments, control unit 110 may be configured to dispense an ethanol-containing inhalant 214 only during permissible times and prevent dispensation of an ethanol-containing inhalant 214 during times that are outside of the permissible times.

In some embodiments, operation 1830 includes preventing dispensation of the ethanol-containing inhalant 214 at one or more impermissible locations (not shown). In some embodiments, system 100 may be used to prevent dispensation of an ethanol-containing inhalant 214 at one or more impermissible locations. In some embodiments, control unit 110 may be configured to prevent dispensation of an ethanol-containing inhalant 214 at one or more impermissible locations. For example, in some embodiments, a control unit 110 may be programmed to prevent dispensation of an ethanol-containing inhalant 214 at one or more global position coordinates. In some embodiments, a control unit 110 may be programmed to prevent dispensation of an ethanol-containing inhalant 214 within an automobile. In some embodiments, a control unit 110 may be programmed to prevent dispensation of an ethanol-containing inhalant 214 within a workplace. Accordingly, a control unit 110 may be programmed to prevent dispensation at numerous locations and types of locations.

In some embodiments, operation 1830 includes dispensing one or more determined quantities of the ethanol-containing inhalant 214 at one or more determined times (not shown). In some embodiments, system 100 may be used to dispense one or more determined quantities of an ethanol-containing inhalant 214 at one or more determined times. In some embodiments, control unit 110 may be configured to dispense one or more determined quantities of an ethanol-containing inhalant 214 at one or more determined times. For example, in some embodiments, control unit 110 may be configured to dispense 4 ounces of an ethanol-containing inhalant 214 between the hours of 6 PM and 11 PM. In some embodiments, control unit 110 may be configured to dispense an ethanol-containing inhalant 214 according to a time schedule. For example, in some embodiments, a control unit 110 may be configured to dispense 1.5 ounces of an ethanol-containing inhalant 214 once every hour. In some embodiments, a control unit 110 may be configured to dispense 1.5 ounces of an ethanol-containing inhalant 214 once every hour between the hours of 7 PM and 11 PM. Accordingly, an ethanol-containing inhalant 214 may be dispensed according to numerous combinations of quantity and time.

In some embodiments, operation 1830 includes dispensing one or more ethosomes (not shown). In some embodiments, system 100 may be used to dispense one or more ethosomes. In some embodiments, control unit 110 may be configured to select one or more inhalant reservoirs 212 that contain ethosomes and control one or more actuators to facilitate at least partial release of ethosomes from the one or more inhalant reservoirs 212. In some embodiments, a control unit 110 may be configured to control one or more actuators 122 to facilitate at least partial release of ethosomal components from an inhalant reservoir 212 that form ethosomes.

In some embodiments, operation 1830 includes dispensing one or more ethanol-containing inhalant 214 formulations (not shown). In some embodiments, system 100 may be used to dispense one or more ethanol-containing inhalant 214 formulations. In some embodiments, control unit 110 may be configured to select one or more inhalant reservoirs 212 that contain an ethanol-containing inhalant 214 formulation and control one or more actuators 122 to facilitate at least partial release of the formulation. For example, in some embodiments, a control unit 110 may be configured to select one or more inhalant reservoirs 212 that contain a desired ethanol-containing inhalant 214 formulation and control one or more actuators 122 to facilitate at least partial release of the selected formulation from the inhalant reservoir 212.

Figure 19:
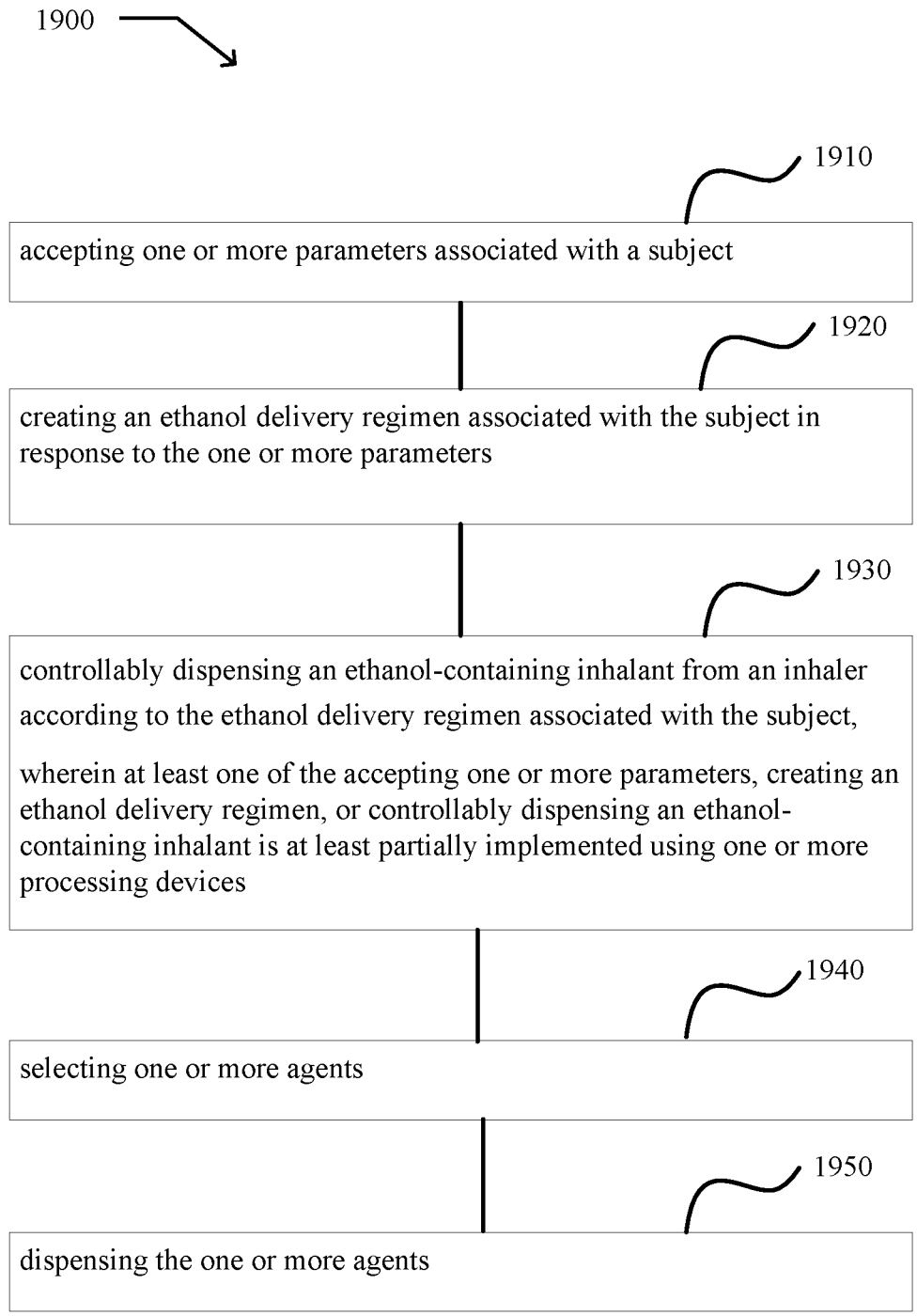
FIG. 19 illustrates an example operational flow 1900 in which embodiments may be implemented.

FIG. 19 illustrates operational flow 1900 that includes operation 1910 that includes accepting one or more parameters associated with a subject; operation 1920 that includes creating an ethanol delivery regimen associated with the subject in response to the one or more parameters; operation 1930 that includes controllably dispensing an ethanol-containing inhalant from an inhaler according to the ethanol delivery regimen associated with the subject, wherein at least one of the accepting one or more parameters, creating an ethanol delivery regimen, or controllably dispensing an ethanol-containing inhalant is at least partially implemented using one or more processing devices; operation 1940 that includes selecting one or more agents; and operation 1950 that includes dispensing the one or more agents. Operations 1910, 1920, and 1930 correspond to operations 1810, 1820, and 1830 as previously described with reference to FIG. 18.

In FIG. 19 and in the following description that includes various examples of operations used during performance of the method, discussion and explanation may be provided with respect to any one or combination of the above-described examples, and/or with respect to other examples and contexts. However, it should be understood that the operations may be executed in a number of other environments and contexts, and/or modified versions of the figures. Also, although the various operations are presented in the sequence(s) illustrated, it should be understood that the various operations may be performed in other orders than those which are illustrated, or may be performed concurrently.

Operation 1940 includes selecting one or more agents 222. In some embodiments, system 100 may be used to select one or more agents 222. In some embodiments, control unit 110 may be configured to select one or more agent reservoirs 220 that include one or more selected agents 222. For example, in some embodiments, a control unit 110 may receive one or more signals 116 from a user interface 112 that include the identities of one or more agents 222 selected by a subject. The control unit 110 may then select one or more agent reservoirs 220 that include the one or more selected agents 222. Numerous types of agents 222 may be selected. Examples of such agents 222 include, but are not limited to, pharmaceutical agents, caffeine, nicotine, tetrahydrocannabinol, and the like.

Operation 1950 includes dispensing the one or more agents 222. In some embodiments, system 100 may be used to dispense one or more agents 222. In some embodiments, control unit 110 may be configured to facilitate the dispensation of one or more agents 222. For example, in some embodiments, a control unit 110 may receive one or more signals that include the identities of one or more agents 222 selected by a subject. The control unit 110 may then select one or more agent reservoirs 220 that include the one or more selected agents 222 and control one or more actuators 122 to facilitate at least partial release of the one or more agents 222 from the one or more agent reservoirs 220.

In some embodiments, operation 1940 includes selecting at least one of caffeine, nicotine, and tetrahydrocannabinol (not shown). In some embodiments, system 100 may be used to select at least one of caffeine, nicotine, and tetrahydrocannabinol. In some embodiments, control unit 110 may be configured to select at least one of caffeine, nicotine, and tetrahydrocannabinol. For example, in some embodiments, a control unit 110 may receive one or more signals 116 from a user interface 112 that include one or more instructions to select at least one of caffeine, nicotine, and tetrahydrocannabinol. The control unit 110 may then select one or more agent reservoirs 220 that include caffeine, nicotine, or tetrahydrocannabinol.

In some embodiments, operation 1950 includes dispensing at least one of caffeine, nicotine, and tetrahydrocannabinol (not shown). In some embodiments, system 100 may be used to dispense at least one of caffeine, nicotine, and tetrahydrocannabinol. In some embodiments, control unit 110 may be configured to facilitate the dispensation of at least one of caffeine, nicotine, and tetrahydrocannabinol. For example, in some embodiments, a control unit 110 may receive one or more signals 116 from a user interface 112 that include one or more instructions to select at least one of caffeine, nicotine, and tetrahydrocannabinol. The control unit 110 may then select one or more agent reservoirs 220 that include caffeine, nicotine, or tetrahydrocannabinol and control one or more actuators 122 to facilitate at least partial release of caffeine, nicotine, and/or tetrahydrocannabinol from the one or more agent reservoirs 220.

Figure 20:
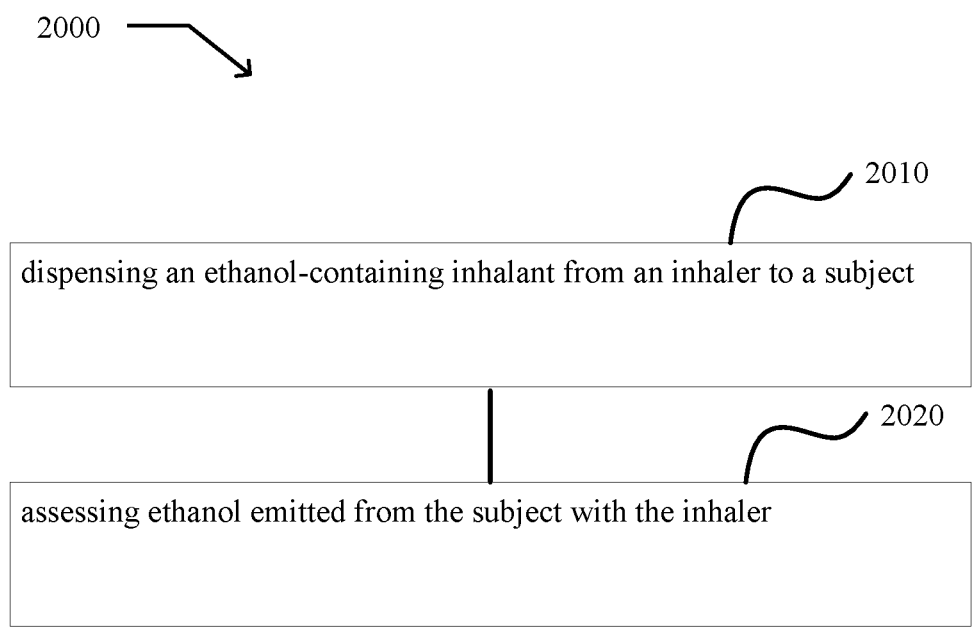
FIG. 20 illustrates an example operational flow 2000 in which embodiments may be implemented.

FIG. 20 illustrates operational flow 2000 that includes operation 2010 that includes dispensing an ethanol-containing inhalant 214 from an inhaler to a subject and operation 2020 that includes assessing ethanol emitted from the subject with the inhaler.

In FIG. 20 and in the following description that includes various examples of operations used during performance of the method, discussion and explanation may be provided with respect to any one or combination of the above-described examples, and/or with respect to other examples and contexts. However, it should be understood that the operations may be executed in a number of other environments and contexts, and/or modified versions of the figures. Also, although the various operations are presented in the sequence(s) illustrated, it should be understood that the various operations may be performed in other orders than those which are illustrated, or may be performed concurrently.

Operation 2010 includes dispensing an ethanol-containing inhalant 214 from an inhaler to a subject. In some embodiments, system 100 may be used to dispense an ethanol-containing inhalant 214 from an inhaler to a subject. For example, in some embodiments, a control unit 110 may control the operation of one or more actuators 122 to facilitate at least partial release of an ethanol-containing inhalant 214 from one or more inhalant reservoirs 212 that are operably coupled to an inhaler.

Operation 2020 includes assessing ethanol emitted from the subject with the inhaler. In some embodiments, system 100 may be used to assess ethanol emitted from a subject with an inhaler. In some embodiments, one or more ethanol sensors 136 may be used to assess ethanol emitted from a subject. In some embodiments, ethanol sensors 136 that are configured to detect metabolites of ethanol may be used to assess ethanol emitted from a subject. In some embodiments, one or more control units 110 may be used to assess ethanol emitted from a subject. In some embodiments, one or more control units 110 may be used to assess a metabolite of ethanol emitted from a subject. In some embodiments, one or more ethanol sensors 136 and one or more control units 110 may be used to assess ethanol emitted from a subject. In some embodiments, one or more ethanol sensors 136 may be physically coupled with an inhaler. For example, in some embodiments, an ethanol sensor 136 may be physically coupled with an inhaler. In some embodiments, an ethanol sensor 136 may be wirelessly coupled with the inhaler. For example, in some embodiments, a remote transdermal ethanol sensor 136 may be wirelessly coupled with an inhaler. Accordingly, in some embodiments, a control unit 110 that is operably coupled with an inhaler may receive one or more signals 114 from one or more ethanol sensors 136 that are configured to detect ethanol, an ethanol metabolite, or a combination thereof to assess ethanol emitted from a subject.

In some embodiments, operation 2010 includes dispensing one or more predetermined quantities of the ethanol-containing inhalant 214 (not shown). In some embodiments, system 100 may be used to dispense one or more predetermined quantities of an ethanol-containing inhalant 214. In some embodiments, control unit 110 may be configured to control one or more actuators 122 to facilitate release of one or more predetermined quantities of an ethanol-containing inhalant 214 from one or more inhalant reservoirs 212. In some embodiments, a control unit 110 may receive one or more signals 114 that include information associated with a predetermined quantity of an ethanol-containing inhalant 214 to be dispensed.

In some embodiments, operation 2010 includes dispensing the ethanol-containing inhalant 214 in one or more predetermined particle sizes (not shown). In some embodiments, system 100 may be used to dispense an ethanol-containing inhalant 214 having one or more predetermined particle sizes. In some embodiments, control unit 110 may be configured to select one or more inhalant reservoirs 212 that contain an ethanol-containing inhalant 214 having one or more predetermined particle sizes and control one or more actuators 122 to facilitate release of the ethanol-containing inhalant 214. In some embodiments, control unit 110 may be configured to control one or more ultrasonic nozzles to produce an ethanol-containing inhalant 214 having one or more predetermined particle sizes.

In some embodiments, operation 2010 includes dispensing one or more ethosomes (not shown). In some embodiments, system 100 may be used to dispensing one or more ethosomes. In some embodiments, control unit 110 may be configured to select one or more inhalant reservoirs 212 that contain ethosomes and control one or more actuators 122 to facilitate release of the ethosomes. In some embodiments, a control unit 110 may select one or more reservoirs 124 that include components that form ethosomes and control one or more actuators 122 to facilitate release of the components and ethanol to form ethosomes. Examples of such components that form ethosomes include, but are not limited to, ethanol, lecithin, and water.

In some embodiments, operation 2020 includes assessing a presence or absence of ethanol emitted from the subject (not shown). In some embodiments, system 100 may be used to assess a presence or absence of ethanol emitted from the subject. In some embodiments, an ethanol sensor 136 may be used to assess a presence or absence of ethanol emitted from a subject using an inhaler. For example, in some embodiments, an ethanol sensor 136 may be operably coupled with a flow channel 104 disposed within an inhaler (see e.g., FIGS. 5-17). In some embodiments, an ethanol sensor 136 may be configured as a breathalyzer. In some embodiments, a control unit 110 may receive one or more signals 114 that include information related to the presence or absence of ethanol emitted from a subject. For example, in some embodiments, an ethanol sensor 136 may be configured as a transdermal ethanol sensor 136 that detects ethanol and then transmits one or more signals 114 that include information related to the presence or absence of ethanol emitted from a subject.

In some embodiments, operation 2020 includes assessing one or more concentrations of the ethanol emitted from the subject (not shown). In some embodiments, system 100 may be used to assess one or more concentrations of the ethanol emitted from a subject. In some embodiments, an ethanol sensor 136 may be used to assess one or more concentrations of ethanol emitted from a subject using an inhaler. For example, in some embodiments, an ethanol sensor 136 that is configured to assess ethanol concentration may be operably coupled with a flow channel 104 disposed within an inhaler (see e.g., FIGS. 5-17). In some embodiments, an ethanol sensor 136 may be configured as a breathalyzer. In some embodiments, a control unit 110 may receive one or more signals 114 that include information related to one or more concentrations of ethanol emitted from a subject. For example, in some embodiments, an ethanol sensor 136 may be configured as a transdermal ethanol sensor 136 that assesses one or more concentrations of ethanol and then transmits one or more signals 114 that include information related to the concentration of ethanol emitted from a subject.

In some embodiments, operation 2020 includes assessing one or more concentrations of the ethanol emitted from the subject at one or more times (not shown). In some embodiments, system 100 may be used to assess one or more concentrations of the ethanol emitted from a subject at one or more times. In some embodiments, an ethanol sensor 136 may be used to assess one or more concentrations of the ethanol emitted from a subject at one or more times. For example, in some embodiments, an ethanol sensor 136 may be operably coupled with a flow channel 104 disposed within an inhaler and used to assess ethanol concentration at one or more times (see e.g., FIGS. 5-17). In some embodiments, an ethanol sensor 136 may be configured as a breathalyzer and used to assess ethanol concentration at one or more times. In some embodiments, a control unit 110 may receive one or more signals 114 that include information related to one or more concentrations of ethanol emitted from a subject at one or more times. For example, in some embodiments, an ethanol sensor 136 may be configured as a transdermal ethanol sensor 136 that assesses one or more concentrations of ethanol at one or more times and then transmits one or more signals 114 that include information related to the concentration of ethanol emitted from a subject.

In some embodiments, operation 2020 includes assessing the ethanol emitted from the subject with a transdermal sensor (not shown). In some embodiments, system 100 may be used to assess the ethanol emitted from the subject with a transdermal sensor. For example, in some embodiments, an ethanol sensor 136 may be a transdermal ethanol sensor 136. In some embodiments, a transdermal ethanol sensor 136 may be used to assess ethanol emitted from a subject. In some embodiments, a transdermal ethanol sensor 136 may be used to assess a presence or absence of ethanol emitted from a subject. In some embodiments, a transdermal ethanol sensor 136 may be used to assess one or more concentrations of ethanol emitted from a subject. In some embodiments, a transdermal ethanol sensor 136 may be used to assess one or more concentrations of ethanol emitted from a subject at one or more times. In some embodiments, a transdermal ethanol sensor 136 may be used to assess one or more concentrations of ethanol emitted from a subject and transmit one or more signals 114 that include information related to one or more assessed concentrations that are received by one or more control units 110.

Figure 21:
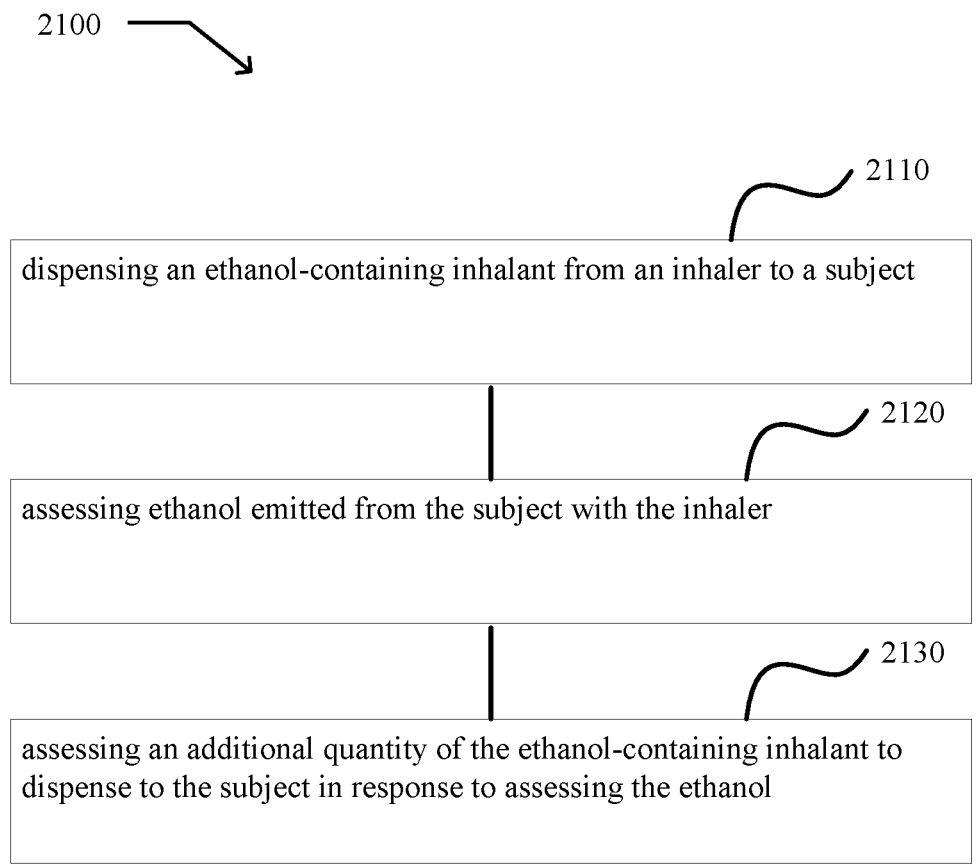
FIG. 21 illustrates an example operational flow 2100 in which embodiments may be implemented.

FIG. 21 illustrates operational flow 2100 that includes operation 2110 that includes dispensing an ethanol-containing inhalant 214 from an inhaler to a subject, operation 2120 that includes assessing ethanol emitted from the subject with the inhaler, and operation 2130 that includes assessing an additional quantity of the ethanol-containing inhalant 214 to dispense to the subject in response to assessing the ethanol. Operations 2110 and 2120 correspond to operations 2010 and 2020 as previously described with reference to FIG. 20.

Operation 2130 includes assessing an additional quantity of the ethanol-containing inhalant 214 to dispense to the subject in response to assessing the ethanol. In some embodiments, system 100 may be used to assess an additional quantity of an ethanol-containing inhalant 214 to dispense to a subject in response to assessing the ethanol. In some embodiments, control unit 110 may be used to assess an additional quantity of an ethanol-containing inhalant 214 to dispense to a subject in response to assessing the ethanol. For example, in some embodiments, a control unit 110 may receive an assessed concentration of ethanol emitted from a subject using an inhaler from an ethanol sensor 136 and then assess an additional quantity of an ethanol-containing inhalant 214 to dispense to the subject. In some embodiments, a control unit 110 may determine an additional quantity of an ethanol-containing inhalant 214 to dispense to the subject through use of a table or a database. For example, in some embodiments, a control unit 110 may access a table that correlates the weight, gender and quantity of alcohol consumed by a subject to the blood alcohol concentration of the subject. The control unit 110 may then use an assessed concentration of ethanol emitted from a subject in combination with such a table to determine an additional quantity of an ethanol-containing inhalant 214 to dispense to the subject to reach a selected blood alcohol concentration within the subject. In some embodiments, a control unit 110 may receive an assessed concentration of ethanol emitted from a subject using an inhaler from an ethanol sensor 136 and then dispense an ethanol-containing inhalant 214 until a desired blood alcohol concentration is achieved.

In some embodiments, operation 2130 includes determining an additional quantity of the ethanol-containing inhalant 214 to dispense to the subject to reach a predetermined blood alcohol content (not shown). In some embodiments, system 100 may be used to determining an additional quantity of the ethanol-containing inhalant 214 to dispense to the subject to reach a predetermined blood alcohol concentration. In some embodiments, control unit 110 may be used to assess an additional quantity of an ethanol-containing inhalant 214 to dispense to a subject to reach a predetermined blood alcohol concentration. For example, in some embodiments, a control unit 110 may receive an assessed concentration of ethanol emitted from a subject using an inhaler from an ethanol sensor 136 and then assess an additional quantity of an ethanol-containing inhalant 214 to dispense to the subject to reach a predetermined blood alcohol concentration. In some embodiments, a control unit 110 may determine an additional quantity of an ethanol-containing inhalant 214 to dispense to the subject through use of a table or a database. For example, in some embodiments, a control unit 110 may access a table that correlates the weight, gender and quantity of alcohol consumed by a subject to the blood alcohol concentration of the subject. The control unit 110 may then use an assessed concentration of ethanol emitted from a subject in combination with such a table to determine an additional quantity of an ethanol-containing inhalant 214 to dispense to the subject to reach a predetermined blood alcohol concentration. In some embodiments, a control unit 110 may receive an assessed concentration of ethanol emitted from a subject using an inhaler from an ethanol sensor 136 and then dispense an ethanol-containing inhalant 214 until a predetermined blood alcohol concentration is achieved.

Figure 22:
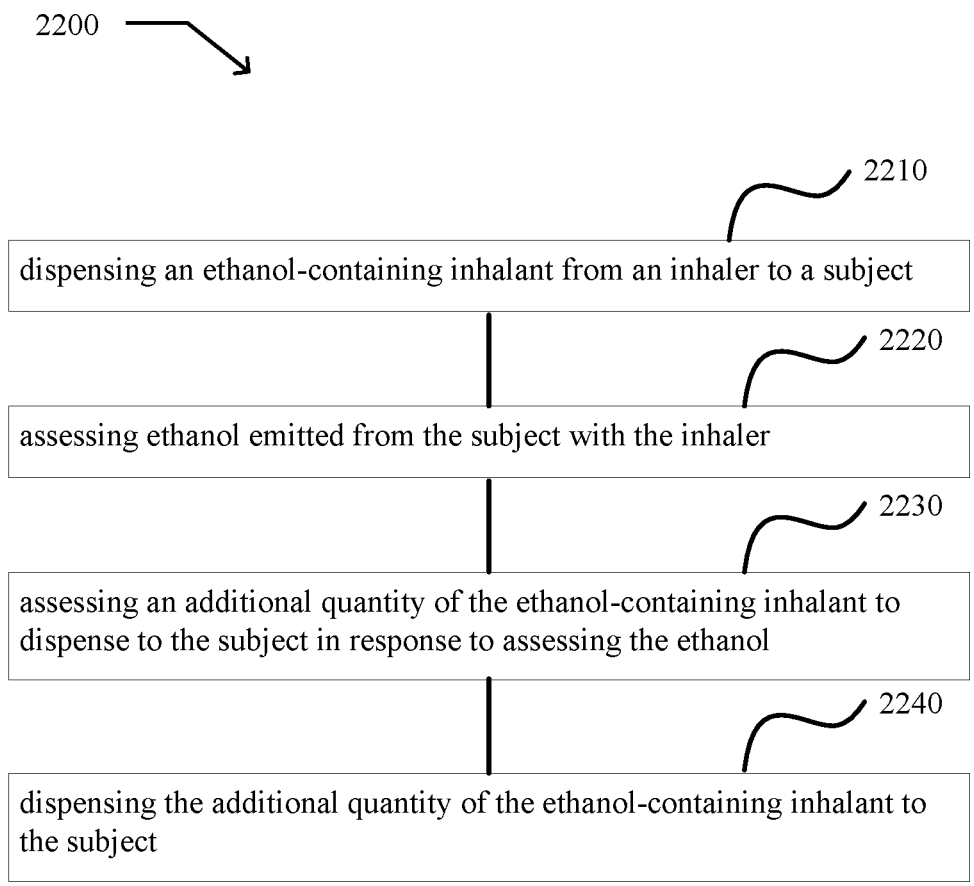
FIG. 22 illustrates an example operational flow 2200 in which embodiments may be implemented.

FIG. 22 illustrates operational flow 2200 that includes operation 2210 that includes dispensing an ethanol-containing inhalant 214 from an inhaler to a subject, operation 2220 that includes assessing ethanol emitted from the subject with the inhaler, operation 2230 that includes assessing an additional quantity of the ethanol-containing inhalant 214 to dispense to the subject in response to assessing the ethanol, and operation 2240 that includes dispensing the additional quantity of the ethanol-containing inhalant 214 to the subject. Operations 2210, 2220, and 2230 correspond to operations 2110, 2120, and 2130 as previously described with reference to FIG. 21.

Operation 2240 includes dispensing the additional quantity of the ethanol-containing inhalant 214 to the subject. In some embodiments, system 100 may be used to dispense an additional quantity of ethanol-containing inhalant 214 to a subject. In some embodiments, a control unit 110 may assess an additional quantity of an ethanol-containing inhalant 214 to dispense to a subject using an inhaler and then control one or more actuators 122 to facilitate release of the additional quantity of the ethanol-containing inhalant 214. For example, in some embodiments, a control unit 110 may cause an aerosol canister content release mechanism to depress an inhalant reservoir 212 that is configured as an aerosol canister to release an assessed quantity of ethanol-containing inhalant 214. In some embodiments, a control unit 110 may cause a controllable valve 264 to open in order to release an assessed quantity of ethanol-containing inhalant 214. Accordingly, a control unit 110 may control numerous types of actuators 122 to dispense and additional quantity of an ethanol-containing inhalant 214 from one or more inhalant reservoirs 212.

In some embodiments, operation 2240 includes dispensing the ethanol-containing inhalant 214 at one or more times (not shown). In some embodiments, system 100 may be used to dispense the ethanol-containing inhalant 214 at one or more times. In some embodiments, a control unit 110 may control one or more actuators 122 to facilitate release of an additional quantity of the ethanol-containing inhalant 214 at one or more times. For example, in some embodiments, a control unit 110 may cause an aerosol canister content release mechanism 268 to depress an inhalant reservoir 212 that is configured as an aerosol canister to release an assessed quantity of ethanol-containing inhalant 214 at one or more times. In some embodiments, a control unit 110 may cause a controllable valve 264 to open in order to release an assessed quantity of ethanol-containing inhalant 214 at one or more times. Accordingly, a control unit 110 may control numerous types of actuators 122 to dispense and additional quantity of an ethanol-containing inhalant 214 from one or more inhalant reservoirs 212 at one or more times.

In some embodiments, operation 2240 includes dispensing one or more ethosomes (not shown). In some embodiments, system 100 may be used to dispense one or more ethosomes. In some embodiments, a control unit 110 may select one or more inhalant reservoirs 212 that contain ethosomes and control one or more actuators 122 to facilitate release of ethosomes from the one or more inhalant reservoirs 212. In some embodiments, a control unit 110 may select one or more reservoirs 124 that contain components that will form ethosomes and control one or more actuators 122 to facilitate release of the components from the one or more reservoirs 124. For example, in some embodiments, a control unit 110 may select a first reservoir 124 that contains lecithin and water and a second reservoir 124 that contains ethanol and then control one or more actuators 122 to facilitate release of the lecithin, water, and ethanol to dispense ethosomes.

In some embodiments, operation 2240 includes dispensing one or more ethanol-containing inhalant 214 formulations (not shown). In some embodiments, system 100 may be used to dispense one or more ethanol-containing inhalant 214 formulations. In some embodiments, a control unit 110 may select on or more inhalant reservoirs 212 that contain one or more selected ethanol-containing inhalant 214 formulation and control one or more actuators 122 to facilitate release of the one or more ethanol-containing inhalant 214 formulations. A control unit 110 may select numerous types of ethanol-containing inhalant 214 formulations. For example, in some embodiments, a control unit 110 may select one or more ethanol-containing inhalant 214 formulations having a desired release profile or combinations of release profiles. In some embodiments, a control unit 110 may select one or more ethanol-containing inhalant 214 formulations that include one or more additional agents 222.

Figure 23:
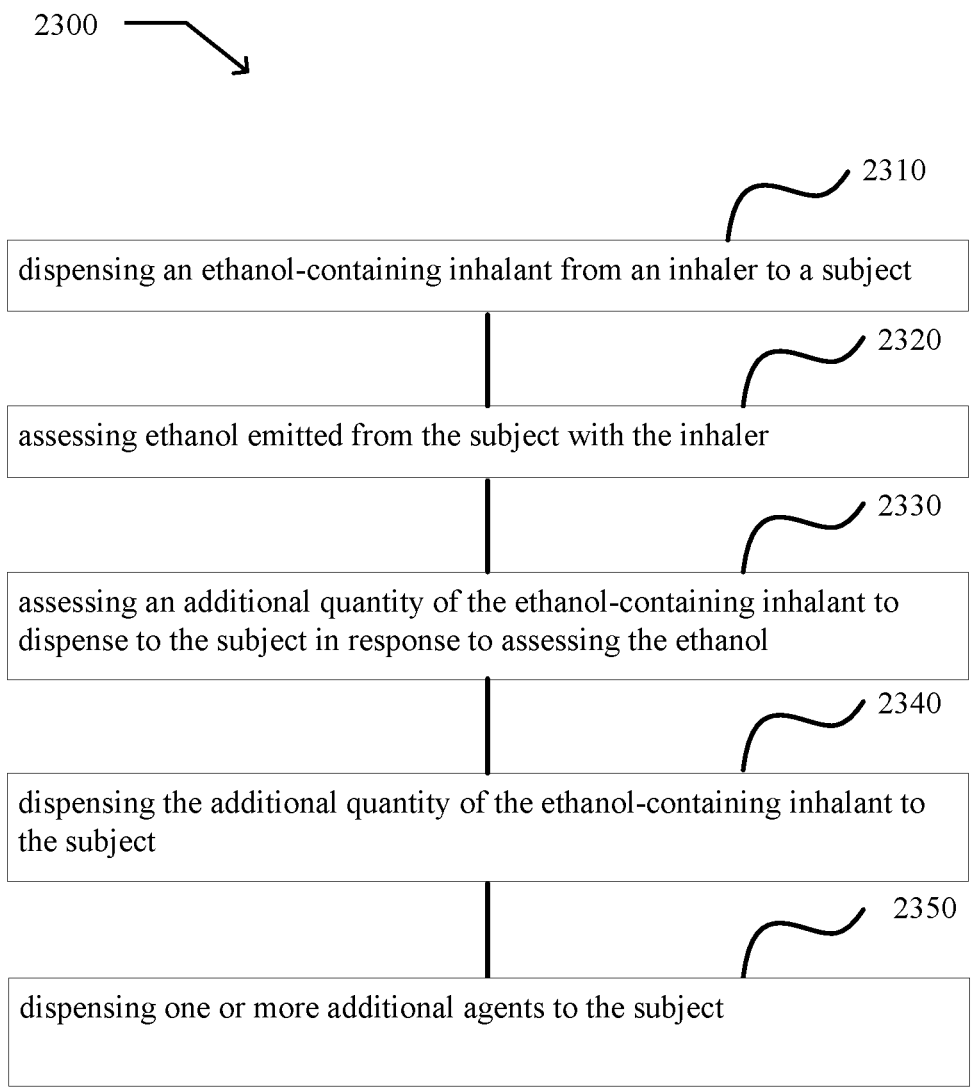
FIG. 23 illustrates an example operational flow 2300 in which embodiments may be implemented.

FIG. 23 illustrates operational flow 2300 that includes operation 2310 that includes dispensing an ethanol-containing inhalant 214 from an inhaler to a subject, operation 2320 that includes assessing ethanol emitted from the subject with the inhaler, operation 2330 that includes assessing an additional quantity of the ethanol-containing inhalant 214 to dispense to the subject in response to assessing the ethanol, operation 2340 that includes dispensing the additional quantity of the ethanol-containing inhalant 214 to the subject, and operation 2350 that includes dispensing one or more additional agents 222 to the subject. Operations 2310, 2320, 2330, and 2340 correspond to operations 2210, 2220, 2230, and 2240 as previously described with reference to FIG. 22.

Operation 2350 includes dispensing one or more additional agents 222 to the subject. In some embodiments, system 100 may be used to dispense one or more additional agents 222 to the subject. In some embodiments, a control unit 110 may select on or more agent reservoirs 220 that contain one or more agents 222 and control one or more actuators 122 to facilitate release of the one or more agents 222. For example, in some embodiments, a control unit 110 may receive one or more signals 114 from a user interface 112 that include information related to one or more subject selected flavorants to dispense. The control unit 110 may then select one or more agent reservoirs 220 that contain the selected flavorants and control one or more actuators 122 to facilitate release of the one or more selected flavorants. Accordingly, a control unit 110 may select one or more agent reservoirs 220 that contain numerous types of agents 222 and control one or more actuators 122 to facilitate release of the one or more agents 222.

In some embodiments, operation 2130 includes dispensing one or more pharmaceutical agents (not shown). In some embodiments, system 100 may be used to dispense one or more pharmaceutical agents. In some embodiments, a control unit 110 may select on or more agent reservoirs 220 that contain one or more pharmaceutical agents and control one or more actuators 122 to facilitate release of the one or more pharmaceutical agents. For example, in some embodiments, a control unit 110 may receive one or more signals 114 from a user interface 112 that include information related to one or more subject selected pharmaceuticals to dispense. The control unit 110 may then select one or more agent reservoirs 220 that contain the selected pharmaceuticals and control one or more actuators 122 to facilitate release of the one or more selected pharmaceuticals. Accordingly, a control unit 110 may select one or more agent reservoirs 220 that contain numerous types of pharmaceutical agents 222 and control one or more actuators 122 to facilitate release of the one or more pharmaceutical agents 222.

In some embodiments, operation 2130 includes dispensing at least one of caffeine, nicotine, and tetrahydrocannabinol (not shown). In some embodiments, system 100 may be used to dispense at least one of caffeine, nicotine, and tetrahydrocannabinol. In some embodiments, a control unit 110 may select on or more agent reservoirs 220 that contain at least one of caffeine, nicotine, and tetrahydrocannabinol and control one or more actuators 122 to facilitate release of at least one of caffeine, nicotine, and tetrahydrocannabinol. For example, in some embodiments, a control unit 110 may receive one or more signals 114 from a user interface 112 that include a request to dispense caffeine. The control unit 110 may then select an agent reservoir 220 that contains caffeine and control one or more actuators 122 to facilitate release of the caffeine. Accordingly, a control unit 110 may select one or more agent reservoirs 220 that contain caffeine, nicotine, and/or tetrahydrocannabinol and control one or more actuators 122 to facilitate release of the caffeine, nicotine, and/or tetrahydrocannabinol.

In some embodiments, a system includes a computer program for executing a computer process on a computing device that may be used to control an inhaler. In some embodiments, such a system is provided that includes a non-transitory signal-bearing medium bearing one or more instructions that, when executed by one or more processing components, direct performance of operations that include at least: accepting one or more parameters associated with a subject; creating an ethanol delivery regimen in response to the one or more parameters; and dispensing an ethanol-containing inhalant 214 from an inhaler according to the ethanol delivery regimen associated with the subject. In some embodiments, the non-transitory signal-bearing medium may further include one or more instructions that direct performance of an operation that includes at least selecting one or more agents 222; and one or more instructions that direct performance of an operation that includes at least dispensing the one or more agents 222. The one or more instructions may be, for example, computer executable and/or logic-implemented instructions. In some embodiments, the non-transitory signal-bearing medium may include a computer-readable medium. In some embodiments, the non-transitory signal-bearing medium may include a recordable medium. In some embodiments, the non-transitory signal-bearing medium may include a communications medium.

In some embodiments, a system includes a computer program for executing a computer process on a computing device that may be used to control an inhaler. In some embodiments, such a system is provided that includes a non-transitory signal-bearing medium bearing one or more instructions that, when executed by one or more processing components, direct performance of operations that include at least: facilitating at least partial release of an ethanol-containing inhalant 214 from at least one ethanol-containing inhalant reservoir 212 that is operably coupled to an inhaler; and assessing ethanol emitted from a subject associated with the inhaler. In some embodiments, the non-transitory signal-bearing medium may further include one or more instructions that direct performance of an operation that includes at least determining an additional quantity of the ethanol-containing inhalant 214 to release in response to assessing the ethanol emitted from the subject. In some embodiments, the non-transitory signal-bearing medium may further include one or more instructions that direct performance of an operation that includes at least facilitating at least partial release of the additional quantity of the ethanol-containing inhalant 214. In some embodiments, the non-transitory signal-bearing medium may further include one or more one or more instructions that direct performance of an operation that includes at least dispensing one or more agents 222 to the subject. The one or more instructions may be, for example, computer executable and/or logic-implemented instructions. In some embodiments, the non-transitory signal-bearing medium may include a computer-readable medium. In some embodiments, the non-transitory signal-bearing medium may include a recordable medium. In some embodiments, the non-transitory signal-bearing medium may include a communications medium.

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

In some instances, one or more components may be referred to herein as "configured to," "configured by," "configurable to," "operable/operative to," "adapted/adaptable," "able to," "conformable/conformed to," etc. Those skilled in the art will recognize that such terms (e.g. "configured to") generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

Those having skill in the art will recognize that the state of the art has progressed to the point where there is little distinction left between hardware, software, and/or firmware implementations of aspects of systems; the use of hardware, software, and/or firmware is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware in one or more machines, compositions of matter, and articles of manufacture, limited to patentable subject matter under 35 USC 101. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

In some implementations described herein, logic and similar implementations may include computer programs or other control structures. Electronic circuitry, for example, may have one or more paths of electrical current constructed and arranged to implement various functions as described herein. In some implementations, one or more media may be configured to bear a device-detectable implementation when such media hold or transmit device detectable instructions operable to perform as described herein. In some variants, for example, implementations may include an update or modification of existing software or firmware, or of gate arrays or programmable hardware, such as by performing a reception of or a transmission of one or more instructions in relation to one or more operations described herein. Alternatively or additionally, in some variants, an implementation may include special-purpose hardware, software, firmware components, and/or general-purpose components executing or otherwise invoking special-purpose components. Specifications or other implementations may be transmitted by one or more instances of tangible transmission media as described herein, optionally by packet transmission or otherwise by passing through distributed media at various times.

Alternatively or additionally, implementations may include executing a special-purpose instruction sequence or invoking circuitry for enabling, triggering, coordinating, requesting, or otherwise causing one or more occurrences of virtually any functional operation described herein. In some variants, operational or other logical descriptions herein may be expressed as source code and compiled or otherwise invoked as an executable instruction sequence. In some contexts, for example, implementations may be provided, in whole or in part, by source code, such as C++, or other code sequences. In other implementations, source or other code implementation, using commercially available and/or techniques in the art, may be compiled/implemented/translated/converted into a high-level descriptor language (e.g., initially implementing described technologies in C or C++ programming language and thereafter converting the programming language implementation into a logic-synthesizable language implementation, a hardware description language implementation, a hardware design simulation implementation, and/or other such similar mode(s) of expression). For example, some or all of a logical expression (e.g., computer programming language implementation) may be manifested as a Verilog-type hardware description (e.g., via Hardware Description Language (HDL) and/or Very High Speed Integrated Circuit Hardware Descriptor Language (VHDL)) or other circuitry model which may then be used to create a physical implementation having hardware (e.g., an Application Specific Integrated Circuit). Those skilled in the art will recognize how to obtain, configure, and optimize suitable transmission or computational elements, material supplies, actuators, or other structures in light of these teachings.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof, limited to patentable subject matter under 35 U.S.C. 101. In an embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, limited to patentable subject matter under 35 U.S.C. 101, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.), etc.).

In a general sense, those skilled in the art will recognize that the various embodiments described herein can be implemented, individually and/or collectively, by various types of electro-mechanical systems having a wide range of electrical components such as hardware, software, firmware, and/or virtually any combination thereof, limited to patentable subject matter under 35 U.S.C. 101; and a wide range of components that may impart mechanical force or motion such as rigid bodies, spring or torsional bodies, hydraulics, electro-magnetically actuated devices, and/or virtually any combination thereof. Consequently, as used herein "electro-mechanical system" includes, but is not limited to, electrical circuitry operably coupled with a transducer (e.g., an actuator, a motor, a piezoelectric crystal, a Micro Electro Mechanical System (MEMS), etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), electrical circuitry forming a communications device (e.g., a modem, communications switch, optical-electrical equipment, etc.), and/or any non-electrical analog thereto, such as optical or other analogs (e.g., graphene based circuitry). Those skilled in the art will also appreciate that examples of electro-mechanical systems include but are not limited to a variety of consumer electronics systems, medical devices, as well as other systems such as motorized transport systems, factory automation systems, security systems, and/or communication/computing systems. Those skilled in the art will recognize that electro-mechanical as used herein is not necessarily limited to a system that has both electrical and mechanical actuation except as context may dictate otherwise.

In a general sense, those skilled in the art will recognize that the various aspects described herein which can be implemented, individually and/or collectively, by a wide range of hardware, software, firmware, and/or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), and/or electrical circuitry forming a communications device (e.g., a modem, communications switch, optical-electrical equipment, etc.). Those having skill in the art will recognize that the subject matter described herein may be implemented in an analog or digital fashion or some combination thereof.

Those skilled in the art will recognize that at least a portion of the devices and/or processes described herein can be integrated into an image processing system. Those having skill in the art will recognize that a typical image processing system generally includes one or more of a system unit housing, a video display device, memory such as volatile or non-volatile memory, processors such as microprocessors or digital signal processors, computational entities such as operating systems, drivers, applications programs, one or more interaction devices (e.g., a touch pad, a touch screen, an antenna, etc.), control systems including feedback loops and control motors (e.g., feedback for sensing lens position and/or velocity; control motors for moving/distorting lenses to give desired focuses). An image processing system may be implemented utilizing suitable commercially available components, such as those typically found in digital still systems and/or digital motion systems.

Those skilled in the art will recognize that at least a portion of the devices and/or processes described herein can be integrated into a data processing system. Those having skill in the art will recognize that a data processing system generally includes one or more of a system unit housing, a video display device, memory such as volatile or non-volatile memory, processors such as microprocessors or digital signal processors, computational entities such as operating systems, drivers, graphical user interfaces, and applications programs, one or more interaction devices (e.g., a touch pad, a touch screen, an antenna, etc.), and/or control systems including feedback loops and control motors (e.g., feedback for sensing position and/or velocity; control motors for moving and/or adjusting components and/or quantities). A data processing system may be implemented utilizing suitable commercially available components, such as those typically found in data computing/communication and/or network computing/communication systems.

The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

All publications, patents and patent applications cited herein are incorporated herein by reference. The foregoing specification has been described in relation to certain embodiments thereof, and many details have been set forth for purposes of illustration, however, it will be apparent to those skilled in the art that the invention is susceptible to additional embodiments and that certain of the details described herein may be varied considerably without departing from the basic principles of the invention.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. An inhaler, comprising:
   a housing having at least one flow channel disposed therein configured to be fluidly coupled to at least one inhalant reservoir including ethanol and at least one agent;
   at least one actuator configured to facilitate at least partial release of at least one ethanol-containing inhalant and the at least one agent from the at least one inhalant reservoir into the at least one flow channel;
   at least one sensor configured to sense at least one agent level within the at least one ethanol-containing inhalant during flow of the at least one ethanol-containing inhalant; and
   at least one control unit operatively coupled to the at least one sensor and to the at least one actuator, the at least one control unit including at least one processing component configured to:
      accept one or more parameters associated with a subject, including at least receive real-time information associated with the one or more parameters from at least one electronic device worn by the subject, the at least one electronic device including a transdermal sensor, the one or more parameters including at least one of a blood alcohol concentration or an ethanol emission detected by the transdermal sensor of at least one electronic device worn by the subject;
      at least one of access or create an ethanol-containing inhalant and agent delivery regimen associated with the subject in response to the one or more parameters, including at least one of:
         at least one of access or create the ethanol-containing inhalant and agent delivery regimen associated with the subject in response to the blood alcohol concentration detected by the transdermal sensor; or
         at least one of access or create the ethanol-containing inhalant and agent delivery regimen associated with the subject in response to the ethanol emission detected by the transdermal sensor;
      receive the at least one agent level sensed by the at least one sensor within the at least one ethanol-containing inhalant during flow of the at least one ethanol-containing inhalant; and
      control operation of the at least one actuator to control dispensation of the at least one agent to provide the ethanol-containing inhalant and agent delivery regimen based at least partially on the at least one agent level within the at least one ethanol-containing inhalant during flow of the at least one ethanol-containing inhalant and the at least one agent within the at least one flow channel.

2. The inhaler of claim 1, wherein the at least one inhalant reservoir includes at least one aerosol canister having a canister body and a valve stem that extends from the canister body, and
   wherein the housing includes at least one reservoir support configured to support the at least one aerosol canister with the valve stem being received by at least one port.

3. The inhaler of claim 1, wherein the at least one actuator comprises:
   at least one aerosol canister content release mechanism.

4. The inhaler of claim 1, wherein the one or more parameters associated with a subject comprises:
   at least one of:
      one or more physical parameters associated with the subject; or
      one or more location parameters associated with the subject.

5. The inhaler of claim 1, further comprising the at least one electronic device configured to be worn by the subject and configured to provide the real-time information associated with the one or more parameters, the at least one electronic device including the transdermal sensor.

6. The inhaler of claim 1, wherein the one or more parameters includes the blood alcohol concentration detected by the transdermal sensor, and wherein the at least one control unit is configured to at least one of access or create an ethanol-containing inhalant and agent delivery regimen associated with the subject in response to the blood alcohol concentration detected by the transdermal sensor.

7. The inhaler of claim 1, wherein the one or more parameters includes the ethanol emission detected by the transdermal sensor, and wherein the at least one control unit is configured to at least one of access or create an ethanol-containing inhalant and agent delivery regimen associated with the subject in response to the ethanol emission detected by the transdermal sensor.

8. The inhaler of claim 1, wherein the one or more parameters associated with a subject includes at least a motion parameter associated with the subject indicative of movement of the subject travelling in a vehicle, and wherein the at least one control unit is further configured to control operation of the at least one actuator to prevent dispensing of the at least one ethanol-containing inhalant and the at least one agent based at least partially on the motion parameter indicative of movement of the subject travelling in the vehicle.

9. The inhaler of claim 1, wherein the at least one control unit configured to at least one of access or create an ethanol-containing inhalant and agent delivery regimen associated with the subject in response to the one or more parameters comprises:
   at least one control unit configured to select an ethanol-containing inhalant and agent delivery regimen in response to a real-time input from a transdermal sensor engaged with a skin surface of the subject, the input from the transdermal sensor being indicative of at least one of a blood sugar level, a blood alcohol concentration, or an ethanol emission level of the subject.

10. The inhaler of claim 1, wherein the at least one control unit configured to control operation of the at least one actuator to facilitate at least partial release of the at least one ethanol-containing inhalant and the at least one agent comprises:

at least one control unit configured to control operation of the at least one actuator to prevent dispensation of the ethanol-containing inhalant and the at least one agent at one or more impermissible times.

11. The inhaler of claim 1, wherein the at least one control unit configured to control operation of the at least one actuator to facilitate at least partial release of the at least one ethanol-containing inhalant and the at least one agent comprises:
at least one control unit configured to control operation of the at least one actuator to prevent dispensation of the ethanol-containing inhalant and the at least one agent at one or more impermissible locations.

12. The inhaler of claim 1, further comprising:
the at least one inhalant reservoir.

13. The inhaler of claim 12, wherein the at least one inhalant reservoir comprises:
an aerosol canister having a canister body and a valve stem.

14. The inhaler of claim 12, wherein the at least one inhalant reservoir contains at least one tracer.

15. The inhaler of claim 1, further comprising the at least one electronic device configured to be worn by the subject, the at least one electronic device including the transdermal sensor.

16. The inhaler of claim 1, wherein the at least one control unit configured to control operation of the at least one actuator to facilitate at least partial release of the at least one ethanol-containing inhalant and the at least one agent comprises:
at least one control unit configured to select one or more flavorants in response to one or more food selections.

17. The inhaler of claim 1, wherein the at least one agent comprises a nicotine agent.

18. The inhaler of claim 1, wherein the at least one agent comprises a caffeine agent.

19. The inhaler of claim 1, wherein the at least one agent comprises a tertrahydrocannabinal agent.

20. The inhaler of claim 1, wherein the one or more parameters associated with a subject includes at least an age parameter, and wherein the at least one control unit is further configured to control operation of the at least one actuator based at least partially on the age parameter and the at least one agent level within the at least one ethanol-containing inhalant during flow of the at least one ethanol-containing inhalant and the at least one agent.

21. The inhaler of claim 1, wherein the one or more parameters associated with a subject includes at least a position associated with a workplace of the subject, and wherein the at least one control unit is further configured to control operation of the at least one actuator to prevent dispensing of the at least one ethanol-containing inhalant and the at least one agent based at least partially on the position associated with a workplace of the subject.

22. The inhaler of claim 1, wherein the ethanol-containing inhalant and agent delivery regimen includes a first non-zero agent dispensation rate and a second non-zero agent dispensation rate.

23. A system comprising:
circuitry configured to accept one or more parameters associated with a subject, including at least a motion parameter associated with the subject indicative of movement of the subject travelling in a vehicle;
circuitry configured to at least one of access or create an ethanol and agent delivery regimen in response to the one or more parameters;
circuitry configured to dispense an ethanol-containing inhalant and at least one agent from an inhaler according to the ethanol and agent delivery regimen associated with the subject;
circuitry configured to sense at least one agent level within the ethanol-containing inhalant during flow of the ethanol-containing inhalant and the at least one agent; and
circuitry configured to control dispensation of the at least one agent to provide a desired release profile into the ethanol-containing inhalant based at least partially on the at least one agent level within the at least one ethanol-containing inhalant during flow of the at least one ethanol-containing inhalant and the at least one agent, and to control dispensation to prevent dispensing of the at least one agent into the ethanol-containing inhalant based at least partially on the motion parameter indicative of movement of the subject travelling in the vehicle.

24. The system of claim 23, wherein the circuitry configured to accept one or more parameters associated with a subject comprises:
at least one of:
circuitry configured to accept one or more location parameters; or
circuitry configured to receive information associated with the one or more parameters from an electronic device associated with the subject.

25. The system of claim 23, wherein the circuitry configured to at least one of access or create an ethanol and agent delivery regimen in response to the one or more parameters comprises:
at least one of:
circuitry configured to determine one or more quantities of the ethanol-containing inhalant to dispense; or
circuitry configured to determine one or more quantities of the ethanol-containing inhalant to dispense at one or more times.

26. The system of claim 23, wherein the circuitry configured to at least one of access or create an ethanol-containing inhalant and agent delivery regimen in response to the one or more parameters comprises:
circuitry configured to select at least one preexisting ethanol-containing inhalant and agent delivery regimen in response to the one or more parameters.

27. The system of claim 23, wherein the circuitry configured to dispense an ethanol-containing inhalant from an inhaler according to the ethanol-containing inhalant and agent delivery regimen associated with the subject comprises:
at least one of:
circuitry configured to prevent dispensation of the ethanol-containing inhalant at one or more permissible times; or
circuitry configured to prevent dispensation of the ethanol-containing inhalant at one or more permissible locations.

28. The system of claim 23, wherein the circuitry configured to dispense an ethanol-containing inhalant from an inhaler according to the ethanol-containing inhalant and agent delivery regimen associated with the subject comprises:
circuitry configured to dispense one or more determined quantities of the ethanol-containing inhalant.

29. The system of claim 23, further comprising:
circuitry configured to select one or more agents; and
circuitry configured to dispense the one or more agents.

30. A system comprising:
a non-transitory signal-bearing medium bearing one or more instructions that, when executed by one or more processing components, direct performance of operations that include at least:
accepting one or more parameters associated with a subject, including at least a motion parameter associated with the subject indicative of movement of the subject travelling in a vehicle;
at least one of accessing or creating an ethanol and agent delivery regimen in response to the one or more parameters;
dispensing an ethanol-containing inhalant and at least one agent from an inhaler according to the ethanol and agent delivery regimen associated with the subject;
sensing at least one agent level within the ethanol-containing inhalant during flow of the ethanol-containing inhalant and the at least one agent; and
controlling dispensation of the at least one agent to provide a desired release profile into the ethanol-containing inhalant based at least partially on the at least one agent level within the at least one ethanol-containing inhalant during flow of the at least one ethanol-containing inhalant and the at least one agent, and to prevent dispensation of the at least one ethanol-containing inhalant and the at least one agent based at least partially on the motion parameter indicative of movement of the subject travelling in the vehicle.

31. The system of claim 30, further comprising:
one or more instructions that direct performance of an operation that includes at least selecting one or more agents; and
one or more instructions that direct performance of an operation that includes at least dispensing the one or more agents.

\* \* \* \* \*